(12) United States Patent
Schwede et al.

(10) Patent No.: US 7,977,325 B2
(45) Date of Patent: Jul. 12, 2011

(54) 3-AMINO-PYRAZOLO[3,4B]PYRIDINES AS INHIBITORS OF PROTEIN TYROSINE KINASES, THEIR PRODUCTION AND USE AS PHARMACEUTICAL AGENTS

(75) Inventors: Wolfgang Schwede, Glienicke (DE); Hermann Kuenzer, Berlin (DE); Antonius Ter Laak, Berlin (DE); Benjamin Bader, Berlin (DE); Roman Hillig, Hamburg (DE); Ursula Moenning, Woltersdorf (DE); Arndt Schmitz, Berlin (DE); Dieter Zopf, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 1432 days.

(21) Appl. No.: 11/302,307

(22) Filed: Dec. 14, 2005

(65) Prior Publication Data
US 2009/0030010 A1    Jan. 29, 2009

Related U.S. Application Data

(60) Provisional application No. 60/636,690, filed on Dec. 17, 2004.

(30) Foreign Application Priority Data

Dec. 14, 2004 (DE) .................. 10 2004 061 288

(51) Int. Cl.
*A61K 31/497* (2006.01)
*A61K 31/44* (2006.01)
*C07D 401/00* (2006.01)
*C07D 515/02* (2006.01)

(52) U.S. Cl. ............ 514/183; 514/303; 514/253.04; 544/362; 546/119

(58) Field of Classification Search .......... None
See application file for complete search history.

(56) References Cited

U.S. PATENT DOCUMENTS

| 4,182,887 | A | * | 1/1980 | Roch et al. | 546/119 |
|---|---|---|---|---|---|
| 4,224,322 | A | * | 9/1980 | Roch et al. | 514/228.5 |
| 4,260,621 | A | * | 4/1981 | Roch et al. | 514/303 |
| 4,366,231 | A | | 12/1982 | Mayer et al. | |
| 5,478,830 | A | | 12/1995 | Higley et al. | |
| 6,046,216 | A | | 4/2000 | Piazza et al. | |
| 6,562,811 | B1 | * | 5/2003 | Murata et al. | 514/222.5 |
| 2004/0014784 | A1 | | 1/2004 | Jakobi et al. | |
| 2004/0255397 | A1 | * | 12/2004 | Fessmann et al. | 8/405 |

FOREIGN PATENT DOCUMENTS

| DE | 2160780 | 6/1973 |
|---|---|---|
| DE | 2238400 | 2/1974 |
| DE | 2355967 | 7/1975 |
| DE | 2643753 | 4/1978 |
| DE | 3001498 | 7/1981 |
| EP | 1308441 | 5/2003 |
| WO | WO 01/19828 | 3/2001 |
| WO | WO 03/008405 | * 1/2003 |
| WO | WO 03008405 | 1/2003 |

OTHER PUBLICATIONS

Jordan, V.C. Nature Reviews: Drug Discovery, 2, 2003, p. 205.*
Dorwald F. Zaragoza. Side Reviews in Organic Synthesis: A guide to successful synthesis design, Weinheim: WILEY-VCH, Verlag, GMBH & Co. KGaA, 2005. Preface.*
Wolff et al. Burger's Medicinal Chemistry and Drug Discovery—Fifth edition, New York: John Wiley & Sons, 1006, vol. 1 pp. 975-976.*
Kaupp., G. et al., European Journal of Organic Chemistry, 2003, pp. 1545-1551, No. 8.
Gamal, A., Zagazig Journal of Pharmaceutical Sciences, 1994, pp. 148-153, vol. 3, No. 2.
Kalme, Z. A. et al., Khimiya Geterotsiklicheskikh Soedinenii, 1992, pp. 1218-1222, No. 9.

(Continued)

*Primary Examiner* — Brandon J Fetterolf
*Assistant Examiner* — Anna Pagonakis
(74) *Attorney, Agent, or Firm* — Millen, White, Zelano & Branigan, P.C.

(57) ABSTRACT

This invention relates to compounds of general formula I

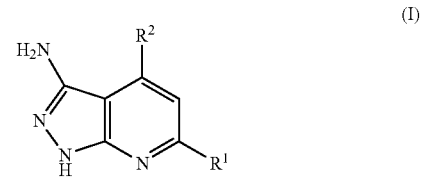

(I)

in which $R^1$ and $R^2$ are described in this application, the use of the compounds of general formula I as inhibitors of protein tyrosine kinases for treatment of various diseases as well as the compounds of general formulas II and III

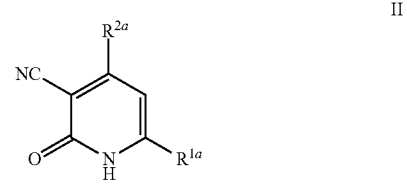

II

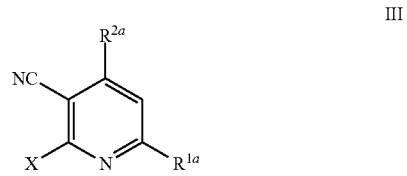

III as intermediate compounds for the production of compounds of general formula I, wherein X, $R^{1a}$ and $R^{2a}$ have the meaning that is described in general formulas II and III.

15 Claims, No Drawings

OTHER PUBLICATIONS

El-Dean, A. M. Kamal et al., Bulletin of the Faculty of Science, 1991, Assiut University, pp. 15-21, vol. 20, No. 1. or Ei-Dean, A. M. et al., Indian Journal of Chemistry, 1991, pp. 878-882, vol. 30B, No. 9.

Gamal et al., Journal of Saudi Chemical Society, 2001, pp. 183-187, vol. 5, No. 2.

Mohamed, A. et al., Phosphorus, Sulfur and Silicon, 2000, pp. 161-179, vol. 167.

Attaby, Fawzy A. et al., Phosphorus, Sulfur and Silicon, 1999, pp. 49-64, vol. 149.

Attaby, Fawzy A. et al., Phosphorus, Sulfur and Silicon, 1999, pp. 253-270, vol. 155.

Sanna, Eldin M. et al., Egyptian Journal of Pharmaceutical Sciences, 1998, pp. 197-209, vol. 39, No. 1-3.

Arustamova, I. S. et al., Chemistry of Heterocyclic Compounds, 1999, pp. 58-63, vol. 35, No. 1.

Lacan, M. and Tabakovic K., Chroatica Chemica Acta, 1975, pp. 127-133, vol. 47, No. 2.

Chandra, Sheker Reddy et al., Journal of Fluorine Chemistry, 1997, pp. 127-130, vol. 86, No. 2.

Abdel, Hafez et al., Collection of Czechoslovak Chemical Communications, 1993, pp. 1198-1202, vol. 58, No. 5.

Deeb, Ali, Collection of Czechoslovak Chemical Communications, 1991, pp. 1560-1563, vol. 56, No. 7.

Gohar, Abdel Kerim et al., Archiv der Pharmazie, 1987, Weinheim, Germany, pp. 823-829, vol. 320, No. 9.

Balicki, R. et al., Polish Journal of Chemistry, 1979, pp. 1515-1525, vol. 53, No. 7-8.

Pejcic, Marijan et al., Acta Pharmaceutica Jugoslavia, 1977, pp. 143-146, vol. 27, No. 3.

Bomika, Z. et al., Khimiya Geterotsiklicheskikh Soedinenii, 1976, pp. 1085-1088, No. 8.

Yoshida, Kei et al., Yakugaku Zasshi, 1976, pp. 33-36, vol. 96, No. 1.

F. E. Goda et al., Bioorganic & Medicinal Chemistry, 2004, pp. 1845-1852, vol. 12, No. 8.

B. Narsaiah et al., Journal of Fluorine Chemistry, 2001, pp. 183-187, vol. 109.

Database Registry, Jul. 10, 2002, XP002373925, Database accession No. RN:438020-37-2, 6-cyclopropyl-4-(4-methoxyphenyl)-1H-Pyrazolo[3,4-b]pyridin-3-amine, Supplier: Ambinter, Summary.

Murata et al., "Discovery of novel and selective IKK-? Serine-threonine protein kinase inhibitors. Part 1" Bioorganic & Medicinal Chemistry Letters, vol. 13, No. 5, 2003, pp. 913-918, XP002373853.

Database Chemcats, Jan. 18, 2005, Interchim Intermediates: XP002373926, Database accession No. 2005:1815941, Chemcats, 4-cyclopropyl-6-(trifluoromethyl)-1H-Pyrazolo[3,4,-b]pyridin-3-amine CAS Registry No. (RN): 832739-88-5, Summary.

* cited by examiner

3-AMINO-PYRAZOLO[3,4B]PYRIDINES AS INHIBITORS OF PROTEIN TYROSINE KINASES, THEIR PRODUCTION AND USE AS PHARMACEUTICAL AGENTS

This application claims the benefit of the filing date of U.S. Provisional Application Ser. No. 60/636,690 filed Dec. 17, 2004 which is incorporated by reference herein.

The invention relates to compounds of general formula (I), production and use as inhibitors of protein tyrosine kinases, in particular Eph (erythropoetin-producing hepatoma amplified sequence) receptors for treating various diseases.

Protein tyrosine kinases catalyze the phosphorylation of specific tyrosine radicals in various proteins. Such phosphorylation reactions play a role in a number of cellular processes that are involved in the regulation of growth and the differentiation of cells. Protein tyrosine kinases are divided into receptor- and non-receptor tyrosine kinases. The family of receptor tyrosine kinases (RTKs) consists of 58 kinases (Manning, G. et al. 2002, Science 298, 1912-1934). RTKs have an extracellular ligand binding domain, a transmembrane domain and an intracellular domain, which generally contains tyrosine kinase activity. RTKs mediate the signal relay of extracellular stimulators such as, e.g., growth factors. The ligand bond results in the dimerization of RTKs and the reciprocal auto-phosphorylation of their intracellular domains. Based on the cell type, specific intracellular binding proteins are thus recruited (i.a., non-receptor tyrosine kinases), via which a signal processing is carried out in the cells (Schlessinger, J. 2000, Cell 103, 211-225). The latter include receptor families of growth factors such as EGF (epidermal growth factor), VEGF (vascular endothelial growth factor), FGF (fibroblast growth factor), PDGF (platelet derived growth factor) and NGF (nerve growth factor), as well as the insulin receptors and the large family of ephrin receptors, etc.

The ephrin (Eph) receptors make up the largest family within the RTKs. They are divided according to their sequential affinity and their ligand specificity into the group of EphA receptors (9 members) and EphB receptors (6 members) (Kullander, K. and Klein, R. 2002, Nat. Rev. Mol. Cell. Biol. 3, 475-486; Cheng, N. et al. 2002, Cyt. and Growth Factor Rev. 13, 75-85). Eph receptors are activated by membrane-fixed ligands of the EphrinA or EphrinB family. EphrinAs are anchored via glycolipids (GPI) in the cell membrane, while EphrinBs have a transmembrane region and an intracellular domain. The interaction between ephrins and the Eph receptors results in a bi-directional signal transfer in the ephrin-expressing cells and in the cells that carry the Eph receptor. Ephrins and Eph receptors play a role in a number of morphogenetic processes in embryonic development and in the adult organism. They are involved in embryonic pattern formation, in the development of the vascular system (Gerety, S. S. et al., 1999, Mol. Cell. 4, 403-414) and in creating neuronal circuits (Flanagan, J. G. and Vanderhaeghen, P., 1998, Annu. Rev. Neurosci. 21, 306-354). In the adult organism, they are involved in the neovascularization process, e.g., in tumor development and in endometriosis, as well as in the morphogenesis of the intestinal epithelium (Battle, E. et al. 2002, Cell 111:251-63). On the cellular plane, they mediate migration, adhesion and juxtacrine cell contacts. Elevated expression of Eph receptors, such as, e.g., EphB2 and EphB4, was also observed in various tumor tissues, such as, e.g., breast tumors and tumors of the intestine (Nakamoto, M. and Bergemann, A. D. 2002, Mic. Res. Tech. 59, 58-67). Knock-out mice of EphB2, EphB3 and EphB4 show defects in the formation of the vascular system. The embryonic mortality of the EphB4-I-mice in embryonic stage d14 shows the special role of EphB4 in this process (Gerety, S. S. et al. 1999, Mol. Cell. 4, 403-414). A modulation of these receptors, e.g., by the inhibition of their kinase activity, results, for example, in that the tumor growth and/or the tumor metastasizing is suppressed either by a direct antitumoral action or by an indirect antiangiogenic action.

Non-receptor tyrosine kinases are present intracellularly in soluble form and are involved in the processing of extracellular signals (e.g., of growth factors, cytokines, antibodies, adhesion molecules) within the cell. They include, i.a., the families of Src (sarcoma) kinases, the Tec (tyrosine kinases expressed in hepatocellular-carcinoma) kinases, the Abl (Abelson) kinases and the Brk (breast-tumor kinase) kinases, as well as the focal adhesion kinase (FAK).

A modified activity of these protein tyrosine kinases can result in the most varied physiological disorders in the human organism and thus cause, e.g., inflammatory, neurological and oncological diseases.

Pyrazolopyridines are described as antimicrobial substances (e.g., Attaby et al., Phosphorus, Sulfur and Silicon and the Related Elements (1999), 149, 49-64; ibid. (1999), 155, 253-270).

In U.S. Pat. No. 5,478,830, pyrazolopyridines are disclosed.

DE 30 01 498 A1 (Agfa-Gevaert AG) discloses pyrazoles that can be used for photographic materials.

Pyrazolopyridines that have an antiphlogistic and in particular antithrombotic action are described in DE 26 43 753 A1 (Dr. Karl Thomae GmbH). The disclosed substituents are always linked via a nitrogen atom to the pyridine in 6-position.

F. E. Goda et al. 2004, Bioorganic & Medicinal Chemistry, 12(8), pp. 1845-1852, discloses pyrazolopyridines that have an antimicrobial action.

B. Narsaiah et al. 2001, Journal of Fluorine Chemistry, 109, 183-7 describes various pyrazolopyridines that are substituted with $CF_3$.

WO 01/19828 A2 discloses a pyrazolopyridine that is substituted with a diaminopyrazolyl group and a methyl group. The substances that are described in this patent can be used as hair dyes.

In WO 01/19828 (BASF AG), the bases for the most varied kinase inhibitors are disclosed. The description contains pyrazolopyridines (structure 95, page 101). In the examples, however, no pyrazolopyridines are disclosed, and the production of the pyrazolopyridines claimed therein is not described.

In other prior art, reference is made to suitable spots in the text. No Eph-receptor inhibitors are described under the receptor tyrosine kinase inhibitors, however.

The object of this invention is to provide compounds that inhibit protein tyrosine kinases, in particular Eph receptors.

FIRST EMBODIMENT OF THE INVENTION

In a first embodiment of this invention, it was now found that compounds of general formula (I)

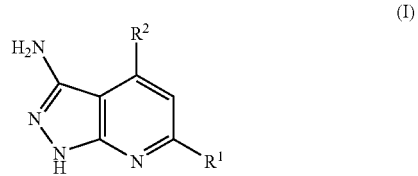

in which
- $R^1$ stands for $C_1$-$C_6$-alkyl, $C_2$-$C_6$-alkenyl, $C_2$-$C_6$-alkinyl, $C_3$-$C_{10}$-cycloalkyl, $C_3$-$C_{10}$-heterocycloalkyl, aryl or heteroaryl that optionally is substituted in one or more places, in the same way or differently, with K, whereby $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring,
- K stands for halogen, hydroxy or the group —O—$R^3$, or for $C_3$-$C_{10}$-cycloalkyl, $C_3$-$C_{10}$-heterocycloalkyl, aryl or heteroaryl that optionally is substituted in one or more places, in the same way or differently, with L, whereby the $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring,
- L stands for $C_1$-$C_6$-alkyl or for the group —$COR^4$ or —$NR^5R^6$,
- $R^2$ stands for $C_1$-$C_6$-alkyl, aryl or heteroaryl that optionally is substituted in one or more places, in the same way or differently, with M,
- $R^3$ stands for $C_1$-$C_6$-alkyl, aryl or —$(CH_2)_n$-aryl that optionally is substituted in one or more places, in the same way or differently, with the group —$NR^5R^6$,
- $R^4$ stands for hydrogen, hydroxy, $C_1$-$C_6$-alkyl or $C_1$-$C_6$-alkoxy,
- M stands for cyano, halogen, hydroxy, nitro or for $C_1$-$C_6$-alkyl, $C_2$-$C_6$-alkenyl, or $C_2$-$C_6$-alkinyl that optionally is substituted in one or more places, in the same way or differently, with amino, cyano, halogen, hydroxy, or $C_1$-$C_6$-alkoxy, or for the group —O—$R^3$ or —$COR^4$,
- $R^5$ and $R^6$, independently of one another, stand for hydrogen, $C_1$-$C_6$-alkyl or for the group —$COR^4$, and
- n stands for 1 to 4, as well as their solvates, hydrates, stereoisomers, diastereomers, enantiomers and salts, with the stipulation that if
- $R^1$ stands for methyl, then $R^2$ cannot simultaneously stand for methyl, —$CH_2$—O—$CH_3$, phenyl, chlorophenyl, or benzofuranyl or furanyl that is substituted with hydroxy and/or methoxy, or if
- $R^1$ stands for —$CH_2$—O—$CH_3$, then $R^2$ cannot simultaneously stand for methyl, or if
- $R^1$ stands for —CH=CH-phenyl, then $R^2$ cannot simultaneously stand for phenyl, or if
- $R^1$ stands for —CH=CH-chlorophenyl, then $R^2$ cannot simultaneously stand for phenyl or chlorophenyl, or if
- $R^1$ stands for —CH=CH-methoxyphenyl, then $R^2$ cannot simultaneously stand for phenyl or methoxyphenyl, or if
- $R^1$ stands for phenyl, then $R^2$ cannot simultaneously stand for —$CF_3$ or phenyl, or if
- $R^1$ stands for chlorophenyl, then $R^2$ cannot simultaneously stand for chlorophenyl, or if
- $R^1$ stands for hydroxyphenyl, then $R^2$ cannot simultaneously stand for heterocycloalkyl or for —COO-tert-butyl-substituted heterocycloalkyl, or if
- $R^1$ stands for benzyloxyphenyl, then $R^2$ cannot simultaneously stand for —COO-tert-butyl-substituted heterocycloalkyl, inhibit protein tyrosine kinases, in particular Eph receptors.

Compounds of the above-mentioned general formula I, in which
- $R^1$ stands for $C_1$-$C_6$ alkyl, $C_3$-$C_{10}$-cycloalkyl, aryl or heteroaryl that optionally is substituted in one or more places, in the same way or differently, with K,
- K stands for halogen, hydroxy or morpholinyl, piperazinyl, piperidinyl or phenoxy that optionally is substituted in one or more places, in the same way or differently, with L,
- L stands for $C_1$-$C_6$-alkyl or —COO—$C_1$-$C_6$ alkyl,
- $R^2$ stands for $C_1$-$C_6$ alkyl, aryl or heteroaryl that optionally is substituted in one or more places, in the same way or differently, with M,
- M stands for cyano, halogen, hydroxy, nitro or for $C_1$-$C_6$-alkyl, $C_2$-$C_6$-alkenyl, or $C_2$-$C_6$-alkinyl that optionally is substituted in one or more places, in the same way or differently, with amino, cyano, halogen, hydroxy, or $C_1$-$C_6$-alkoxy, or for the group —O—$C_1$-$C_6$-alkyl, —O—$(CH_2)_n$—N($C_1$-$C_6$-alkyl)$_2$, —CO—$C_1$-$C_6$-alkyl, —O-phenyl or —O—$(CH_2)_n$-phenyl, and
- n stands for 1 to 4, as well as their solvates, hydrates, stereoisomers, diastereomers, enantiomers and salts, are preferred.

Compounds of the above-mentioned general formula I, in which
- $R^1$ stands for tert-butyl, cyclopropyl, cyclohexyl, cyclohexanone, 1,4-dioxa-spiro[4.5]dec-8-yl, phenyl, 1,3-benzodioxolyl or pyridinyl that optionally is substituted in one or more places, in the same way or differently, with K,
- K stands for halogen, hydroxy or morpholinyl, piperazinyl, piperidinyl, methoxy or phenoxy that optionally is substituted in one or more places, in the same way or differently, with L,
- L stands for methyl or —COO-tert-butyl,
- $R^2$ stands for isopropyl, phenyl, quinolinyl, imidazolyl, indolyl or pyridinyl that optionally is substituted in one or more places, in the same way or differently, with M, and
- M stands for cyano, halogen, hydroxy, nitro, methyl, —$CF_3$ or for methoxy or for the group —CO-methyl, —O—$(CH_2)_3$—N(methyl)$_2$, phenoxy or benzyloxy, as well as their solvates, hydrates, stereoisomers, diastereomers, enantiomers and salts, are especially preferred.

In addition, compounds of the above-mentioned general formula I, in which
- $R^1$ stands for $C_1$-$C_6$-alkyl, $C_2$-$C_6$-alkenyl, $C_2$-$C_6$-alkinyl, $C_3$-$C_{10}$-cycloalkyl, $C_3$-$C_{10}$-heterocycloalkyl, aryl or heteroaryl that optionally is substituted in one or more places, in the same way or differently, with K, whereby the $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring,
- K stands for halogen, hydroxy or the group —O—$R^3$ or —$NR^5R^6$ or for $C_3$-$C_{10}$-cycloalkyl, $C_3$-$C_{10}$-heterocycloalkyl, aryl or heteroaryl that optionally is substituted in one or more places, in the same way or differently, with L, whereby the $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, L stands for $C_1$-$C_6$-alkyl or the group —$COR^4$ or —$NR^5R^6$, $R^2$ stands for $C_1$-$C_6$-alkyl, aryl or heteroaryl that optionally is substituted in one or more places, in the same way or differently, with M, $R^3$ stands for $C_1$-$C_6$-alkyl, aryl or —$(CH_2)_n$-aryl that optionally is substituted in one or more places, in the same way or differently, with the group —$NR^5R^6$, $R^4$ stands for hydrogen, hydroxy, $C_1$-$C_6$-alkyl or $C_1$-$C_6$-alkoxy, M stands for cyano, halogen, hydroxy, nitro or for $C_1$-$C_6$-alkyl, $C_2$-$C_6$-alkenyl or $C_2$-$C_6$-alkinyl that optionally is substituted in one or more places, in the same way or differently, with amino, cyano, halogen, hydroxy, or $C_1$-$C_6$-alkoxy, or for the group —O—$C_1$-$C_6$-alkyl, —O—$(CH_2)_n$—$NR^5R^6$ or —$COR^4$, $R^5$ and $R^6$, independently of one another, stand for hydrogen, $C_1$-$C_6$-alkyl or for the group —$COR^4$, and n stands for 1 to 4, as well as their solvates, hydrates, stereoisomers, diastereomers, enantiomers and salts, are preferred.

In addition, those compounds of the above-mentioned general formula I, in which $R^1$ stands for $C_1$-$C_6$ alkyl, $C_3$-$C_{10}$-cycloalkyl, aryl or heteroaryl that optionally is substituted in one or more places, in the same way or differently, with K, K stands for halogen, hydroxy or morpholinyl, piperazinyl, piperidinyl or phenyoxy that optionally is substituted in one or more places, in the same way or differently, with L, L stands for $C_1$-$C_6$-alkyl or —COO—$C_1$-$C_6$ alkyl, $R^2$ stands for $C_1$-$C_6$ alkyl, aryl or heteroaryl that optionally is substituted in one or more places, in the same way or differently, with M, M stands for cyano, halogen, hydroxy, nitro or for $C_1$-$C_6$-alkyl, $C_2$-$C_6$-alkenyl, or $C_2$-$C_6$-alkinyl that optionally is substituted in one or more places, in the same way or differently, with amino, cyano, halogen, hydroxy, or $C_1$-$C_6$-alkoxy, or for the group —O—$C_1$-$C_6$-alkyl, —O—$(CH_2)_n$—$N(C_1$-$C_6$-alkyl$)_2$ or —CO—$C_1$-$C_6$-alkyl, and n stands for 1 to 4, as well as their solvates, hydrates, stereoisomers, diastereomers, enantiomers, and salts, are preferred.

Those compounds of the above-mentioned general formula, in which $R^1$ stands for $C_1$-$C_6$-alkyl, $C_3$-$C_{10}$-cycloalkyl, cyclohexanone, 1,4-dioxa-spiro[4.5]dec-8-yl, phenyl, 1,3-benzodioxolyl or pyridinyl that optionally is substituted in one or more places, in the same way or differently, with K, K stands for halogen, hydroxy or morpholinyl, piperazinyl, piperidinyl, methoxy or phenoxy that optionally is substituted in one or more places, in the same way or differently, with L, L stands for $C_1$-$C_6$-alkyl or —COO—$C_1$-$C_6$ alkyl, $R^2$ stands for $C_1$-$C_6$-alkyl, phenyl or quinolinyl, imidazolyl, indolyl or pyridinyl that optionally is substituted in one or more places, in the same way or differently, with M, M stands for cyano, halogen, hydroxy, nitro or for $C_1$-$C_6$-alkyl that optionally is substituted in one or more places, in the same way or differently, with amino, cyano, halogen, hydroxy, or $C_1$-$C_6$-alkoxy, or for the group —O—$C_1$-$C_6$-alkyl, —O—$(CH_2)_n$—$N(C_1$-$C_6$-alkyl$)_2$ or —CO—$C_1$-$C_6$-alkyl, and n stands for 1 to 4, as well as their solvates, hydrates, stereoisomers, diastereomers, enantiomers and salts, are especially preferred.

Those compounds of general formula I, in which $R^1$ stands for tert-butyl, cyclopropyl, cyclohexyl, cyclohexanone, 1,4-dioxa-spiro[4.5]dec-8-yl, phenyl, 1,3-benzodioxolyl or pyridinyl that optionally is substituted in one or more places, in the same way or differently, with K, K stands for halogen, hydroxy or morpholinyl, piperazinyl, piperidinyl, methoxy or phenoxy that optionally is substituted in one or more places, in the same way or differently, with L, L stands for methyl or —COO-tert-butyl, $R^2$ stands for isopropyl, phenyl, quinolinyl, imidazolyl, indolyl or pyridinyl that optionally is substituted in one or more places, in the same way or differently, with M, and M stands for cyano, halogen, hydroxy, nitro, methyl, —$CF_3$ or for methoxy or for the group —CO-methyl, —O—$(CH_2)_3$—$N(methyl)_2$, phenoxy or benzyloxy, as well as their solvates, hydrates, stereoisomers, diastereomers, enantiomers and salts, are very highly preferred.

The intermediate products that are preferably used for the production of the compounds of general formula I according to the invention in accordance with this first embodiment of the invention are the following compounds of general formulas II and III

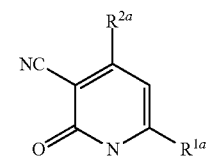

II

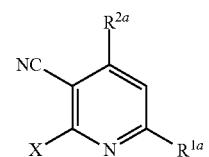

III in which

X stands for halogen or —O—$SO_2$—$C_mF_{2m+1}$, m stands for 1 to 4, $R^{1a}$ stands for $C_1$-$C_6$-alkyl, $C_1$-$C_6$-alkenyl, $C_2$-$C_6$-alkinyl, $C_3$-$C_{10}$-cycloalkyl, $C_3$-$C_{10}$-heterocycloalkyl, aryl or heteroaryl that optionally is substituted in one or more places, in the same way or differently, with $K^a$, whereby the $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, $K^a$ stands for halogen, hydroxy, the group —O—$R^{3a}$, —$COR^{4a}$ or —$NR^{5a}R^6$a, or for $C_3$-$C_{10}$-cycloalkyl, $C_3$-$C_{10}$-heterocycloalkyl, aryl or heteroaryl that optionally is substituted in one or more places, in the same way or differently, with $L^a$, whereby the $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, $L^a$ stands for $C_1$-$C_6$-alkyl or the group —$COR^{4a}$ or —$NR^{5a}R^{6a}$, $R^{2a}$ stands for $C_1$-$C_6$-alkyl, aryl or heteroaryl that optionally is substituted in one or more places, in the same way or differently, with $M^a$, $R^{3a}$ stands for trimethylsilyl (TMS), tert-butyl-dimethylsilyl (TBDMS), tert-butyl-diphenylsilyl (TBDPS), triethylsilyl (TES), $C_1$-$C_2$-alkyl, $C_3$-$C_6$-allyl, benzyl or for the group —$COR^{4a}$ or for $C_1$-$C_6$-alkyl, aryl or —$(CH_2)_n$-aryl that optionally is substituted in one or more places, in the same way or differently, with the group —$NR^{5a}R^{6a}$, $R^{4a}$ stands for hydrogen, $C_1$-$C_6$-alkyl or $C_1$-$C_6$-alkoxy, $M^a$ stands for cyano, halogen, hydroxy, nitro or for $C_1$-$C_6$-alkyl, $C_2$-$C_6$-alkenyl, or $C_2$-$C_6$-alkinyl that optionally is substituted in one or more places, in the same way or differently, with amino, cyano, halogen, hydroxy, or $C_1$-$C_6$-alkoxy, or for the group —O—$R^{3a}$ or —$COR^{4a}$, $R^{5a}$ and $R^{6a}$, independently of one another, stand for hydrogen, $C_1$-$C_6$-alkyl or for the group $COR^{4a}$, and $n^a$ stands for 1 to 4, as well as their solvates, hydrates, stereoisomers, diastereomers, enantiomers and salts.

Alkyl is defined in each case as a straight-chain or branched alkyl radical, such as, for example, methyl, ethyl, propyl, isopropyl, butyl, isobutyl, sec-butyl, tert-butyl, pentyl, isopentyl, hexyl, heptyl, octyl, nonyl and decyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy or decyloxy.

The alkenyl substituents are in each case straight-chain or branched, whereby, for example, the following radicals are meant: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl, or allyl.

Alkinyl is defined in each case as a straight-chain or branched alkinyl radical that contains 2-6, preferably 2-4, C atoms. For example, the following radicals can be mentioned: acetylene, propin-1-yl, propin-3-yl, but-1-in-1-yl, but-1-in-4-yl, but-2-in-1-yl, but-1-in-3-yl, etc.

Heterocyclyl or $C_3$-$C_{10}$-heterocycloalkyl stands for an alkyl ring that comprises 3-10 carbon atoms and is interrupted by at least one of the following atoms nitrogen, oxygen and/or sulfur in the ring, and the $C_3$-$C_{10}$-heterocycloalkyl optionally can be interrupted by one or more —(CO)—, —SO— or —$SO_2$— groups that are the same or different in the ring, and optionally one or more double bonds can be contained in the ring. Only those combinations are meant, however, that are useful from the viewpoint of one skilled in the art, in particular in reference to ring strain.

As heterocyclyls, there can be mentioned, e.g.: oxiranyl, oxethanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl, etc.

Cycloalkyls are defined as monocyclic $C_3$-$C_{10}$ alkyl rings, such as cyclopropyl, cyclobutyl, cyclopentyl, cyclohexyl or cycloheptyl, but also bicyclic rings or tricyclic rings, such as, for example, adamantanyl or 1,4-dioxa-spiro[4,5]dec-8-yl. The cycloalkyl rings can be unsubstituted or substituted in one or more places.

An aryl radical in each case has 6-12 carbon atoms, such as, for example, naphthyl, biphenyl and in particular phenyl.

The heteroaryl radical in each case comprises 3-16 ring atoms and instead of carbon contains one or more of the heteroatoms that are the same or different from the group oxygen, nitrogen or sulfur, can be monocyclic, bicyclic or tricyclic and in addition in each case can be benzocondensed. Only those combinations are meant, however, that are useful from the viewpoint of one skilled in the art, in particular in reference to ring strain.

The heteroaryl rings can be unsubstituted or substituted in one or more places.

For example, there can be mentioned: thienyl, furanyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl as well as benzo derivatives thereof, such as, e.g., 1,3-benzodioxolyl, benzofuranyl, benzothienyl, benzoxazolyl, benzimidazolyl, indazolyl, indolyl, isoindolyl, oxepinyl, azocinyl, indolizinyl, indolyl, isoindolyl, indazolyl, benzimidazolyl, purinyl, or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, etc.

Halogen is defined in each case as fluorine, chlorine, bromine or iodine.

ADDITIONAL EMBODIMENT OF THE INVENTION

In an additional embodiment of this invention that achieves the object, there are, according to a 1$^{st}$ aspect, compounds of general formula (I),

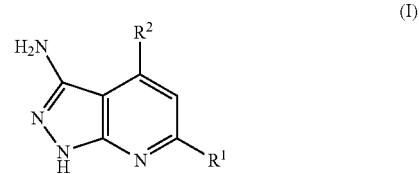

in which $R^1$ stands for $C_1$-$C_6$-alkyl, $C_2$-$C_6$-alkenyl, $C_2$-$C_6$-alkinyl, $C_3$-$C_{10}$-cycloalkyl, $C_3$-$C_{10}$-heterocycloalkyl, aryl or heteroaryl that optionally is substituted in one or more places, in the same way or differently, with K, whereby the $C_3$-$C_{10}$-heterocycloalkyl and/or the heteroaryl itself is interrupted by at least one of the following atoms nitrogen, oxygen and/or sulfur in the ring, and the $C_3$-$C_{10}$-heterocycloalkyl and/or heteroaryl can be linked only via a carbon ring atom with the pyrazolopyridine, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, or stands for a $C_3$-$C_{10}$-cycloalkyl, aryl, $C_3$-$C_{10}$-heterocycloalkyl or heteroaryl that is substituted with the group —O—$(CH_2)_n$—O—, whereby the terminal oxygen atoms of the —O—$(CH_2)_n$—O— group are linked to the same or a directly adjacent $C_3$-$C_{10}$-cycloalkyl ring-, aryl ring-, $C_3$-$C_{10}$-heterocycloalkyl ring- or heteroaryl ring-carbon atom, K stands for halogen, hydroxy or the group —$OR^3$, —$COR^4$ or —$NR^5R^6$, or for $C_3$-$C_{10}$-cycloalkyl, $C_3$-$C_{10}$-heterocycloalkyl, aryl or heteroaryl that optionally is substituted in one or more places, in the same way or differently, with L, whereby the $C_3$-$C_{10}$-heterocycloalkyl and/or the heteroaryl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, L stands for $C_1$-$C_6$-alkyl or the group —$COR^4$, —$OR^3$ or —$NR^5R^6$, $R^2$ stands for $C_1$-$C_6$ alkyl, $C_3$-$C_{10}$-cycloalkyl, aryl or heteroaryl that optionally is substituted in one or more places, in the same way or differently, with M, $R^3$ stands for $C_1$-$C_6$-alkyl, aryl or —$(CH_2)_n$-aryl that optionally is substituted in one or more places, in the same way or differently, with the group —$NR^5R^6$, $R^4$ stands for hydrogen, hydroxy, $C_1$-$C_6$-alkyl or $C_1$-$C_6$-alkoxy, M stands for amino, cyano, halogen, hydroxy, or nitro or for $C_1$-$C_6$-alkyl, $C_2$-$C_6$-alkenyl, or $C_2$-$C_6$-alkinyl that optionally is substituted in one or more places, in the same way or differently, with amino, cyano, halogen, hydroxy, nitro, or $C_1$-$C_6$-alkoxy, or for the group —$OR^3$, —$COR^4$, or —CO—N—$R^7$, $R^5$ and $R^6$, independently of one another, stand for hydrogen, $C_1$-$C_6$-alkyl or for the group —$COR^4$, and $R^7$ stands for hydrogen, or $NH_2$, n stands for 1 to 4, with the stipulation that if $R^1$ stands for methyl, then $R^2$ cannot simultaneously stand for methyl, —$CH_2$—O—$CH_3$, phenyl, chlorophenyl, benzofuranyl that is substituted with hydroxy and/or methoxy, —$CF_3$ or furanyl, or if $R^1$ stands for —$CH_2$—O—$CH_3$, then $R^2$ cannot simultaneously stand for methyl, or if $R^1$ stands for —CH=CH-phenyl, then $R^2$ cannot simultaneously stand for phenyl, or if $R^1$ stands for —CH=CH-chlorophenyl, then $R^2$ cannot simultaneously stand for phenyl or chlorophenyl, or if $R^1$ stands for —CH=CH-methoxyphenyl, then $R^2$ cannot simultaneously stand for phenyl or methoxyphenyl, or if $R^1$ stands for phenyl, then $R^2$ cannot simultaneously stand for —$CF_3$, methyl, methoxyphenyl or phenyl, or if $R^1$ stands for methoxyphenyl, then $R^2$ cannot simultaneously stand for —$CF_3$, or if $R^1$ stands for methylphenyl, then $R^2$ cannot simultaneously stand for —$CF_3$, or if $R^1$ stands for chlorophenyl, then $R^2$ cannot simultaneously stand for chlorophenyl or —$CF_3$, or if $R^1$ stands for dichlorophenyl, then $R^2$ cannot simultaneously stand for trimethoxyphenyl, or if $R^1$ stands for bromophenyl, then $R^2$ cannot simultaneously stand for trimethoxyphenyl, or if $R^1$ stands for alkyl, alkenyl, aryl, aralkyl, cycloalkyl, or for an alkyl that is substituted with phenyl or p-methoxyphenyl, then $R^2$ cannot simultaneously also stand for alkyl, alkenyl, aryl, aralkyl, cyano, a heterocyclic radical or cycloalkyl, or if $R^1$ stands for a lower alkyl radical, alkoxy or aryloxy, then $R^2$ simultaneously cannot stand for a lower alkyl radical, or if $R^1$ stands for hydroxyphenyl, then $R^2$ cannot simultaneously stand for heterocyclyl or a —COO-tert-butyl-substituted heterocycloalkyl, or if $R^1$ stands for benzyloxyphenyl, then $R^2$ cannot simultaneously stand for a —COO-tert-butyl-substituted heterocycloalkyl, as well as their solvates, hydrates, stereoisomers, diastereomers, enantiomers and salts.

In an alternate embodiment, $R^1$=methyl, then $R^2$ is not=methyl or ethyl, or if $R^2$=methyl, then $R^1$ is not=methyl or ethyl, or if $R^1$=chlorophenyl, then $R^2$ is not=chlorophenyl or methylchlorophenyl, or if $R^2$=chlorophenyl, then $R^1$ is not=—$CH_2$-phenyl, or if $R^1$=methyl, then $R^2$ is not=chlorophenyl, furanyl, methylchlorophenyl or methylfuranyl, or if $R^2$=chlorophenyl or furanyl, then $R^1$ is not=methyl or ethyl, or if $R^1$=—CH=CH-phenyl, then $R^1$ is not=phenyl, or methylphenyl, or if $R^2$=phenyl, then $R^1$ is not=—$C_{1-3}$-alkyl-phenyl, $C_{2-3}$-alkenyl-phenyl, $C_{2-3}$-alkinyl-phenyl, or —CH=CH-methylphenyl, or if $R^1$=—CH=CH-methoxyphenyl, then $R^2$ is not=phenyl, methylphenyl, methoxyphenyl, ethoxyphenyl, hydroxyphenyl, or methoxyphenyl with an additional methyl substituent, or if $R^2$=phenyl or methoxyphenyl, then $R^1$ is not=—$C_{1-3}$-alkyl-methoxyphenyl, $C_{2-3}$-alkenyl-methoxyphenyl, or $C_{2-3}$-alkinyl-methoxyphenyl, or if $R^1$=—CH=CH-chlorophenyl, then $R^2$ is not=phenyl, methylphenyl, chlorophenyl, or methylchlorophenyl, or if $R^2$=phenyl or chlorophenyl, then $R^1$ is not=—$C_{1-3}$-alkyl-chlorophenyl, $C_{2-3}$-alkenyl-chlorophenyl, $C_{2-3}$-alkinyl-chlorophenyl, or —CH=CH-methylphenyl, or if $R^1$=methyl, then $R^2$ is not=—$CH_2$—O—$CH_3$, —$CH_2$—$CH_2$—O—$CH_3$, or —$CH_2$—O—$CH_2$—$CH_3$, $R^2$=—$CH_2$—O—$CH_3$, then $R^1$ is not=methyl or ethyl, or if $R^1$=phenyl, then $R^2$ is not=—$CF_3$ or $C_{1-2}$-alkyl that is optionally substituted with halogen, preferably with 3 F groups, or if $R^2$=—$CF_3$, then $R^1$ is not=phenyl or —$CH_2$-phenyl, or if $R^1$=methylphenyl, then $R^2$ is not=—$CF_3$ or $C_{1-2}$-alkyl optionally substituted with halogen, preferably with 3 F groups, or if $R^2$=—$CF_3$, then $R^1$ is not=phenyl, methylphenyl, ethylphenyl, or —$CH_2$-methylphenyl, or if $R^1$=methoxyphenyl, then $R^2$ is not=—$CF_3$ or $C_{1-2}$-alkyl optionally substituted with halogen, preferably with 3 F groups, or if $R^2$=—$CF_3$, then $R^1$ is not=methoxyphenyl, ethoxyphenyl, or hydroxyphenyl, or if $R^1$=chlorophenyl, then $R^2$ is not=—$CF_3$ or $C_{1-2}$-alkyl optionally substituted with halogen, preferably with 3 F groups, or if $R^2$=—$CF_3$, then $R^1$ is not=chlorophenyl, or if $R^1$=phenyl, then $R^2$ is not=phenyl or methylphenyl, or if R=phenyl, then $R^1$ is not=—$CH_2$-phenyl, or if $R^1$=methyl, then $R^2$ is not=benzofuranyl that is substituted with hydroxy and/or methoxy or ethoxy, or benzofuranyl that is substituted with hydroxy and/or methoxy and an additional methyl, or if $R^2$=benzofuranyl that is substituted with hydroxy and/or methoxy, then $R^1$ is not=methyl or ethyl, or if $R^2$=methyl, then $R^2$ is not=—$CF_3$ or $C_{1-2}$-alkyl optionally substituted with halogen, preferably with 3 F groups, or if $R^2$=—$CF_3$, then $R^1$ is not=methyl or ethyl, or if $R^1$=—$CH_2$—O—$CH_3$, then $R^2$ is not=methyl or ethyl, or if $R^2$=methyl, then $R^1$ is not=—$CH_2$—O—$CH_3$, —$CH_2$—$CH_2$—O—$CH_3$, —$CH_2$—O—$CH_2$—$CH_3$, —CH=CH—O—$CH_3$, —$CH_2$—O—CH=$CH_2$, —C≡C—O—$CH_3$, or —$CH_2$—O—C≡C, or if $R^1$=methyl, then $R^2$ is not=phenyl or methylphenyl, or if $R^2$=phenyl, then $R^1$ is not=methyl or ethyl, or if $R^1$=dichlorophenyl, then $R^2$ is not=trimethoxyphenyl, or a dimethoxyphenyl group that additionally is substituted with a hydroxy or ethoxy group, or a trimethoxyphenyl that is substituted with a methyl group, or if $R^1$=bromophenyl, then $R^2$ is not=trimethoxyphenyl or a dimethoxyphenyl group that additionally is substituted with a hydroxy or ethoxy group, or trimethoxyphenyl that is substituted with a methyl group, or if $R^1$=hydroxyphenyl, then $R^2$ is not=piperidine or methylpiperidine, or if $R^1$=phenyl, then $R^2$ is not=methoxyphenyl, ethoxyphenyl, or hydroxyphenyl, or if $R^2$=methoxyphenyl, then $R^1$ is not=phenyl or —$CH_2$-phenyl, or if R=methyl, then $R^1$ is not=—$CH_2$-phenyl, or if $R^1$=phenyl, then $R^2$ is not=methyl or ethyl, or if $R^1$ stands for an unsubstituted alkyl, alkenyl, aryl, aralkyl or cycloalkyl group, then $R^2$ is not an unsubstituted alkyl, alkenyl, aryl, aralkyl or cycloalkyl group, or if $R^1$ stands for diaminopyrazolyl-, then $R^2$- is not methyl or ethyl, or if $R^1$ stands for hydrogen, an optionally substituted alkyl, aralkyl-, cycloalkyl-, or aryl radical, for example, a methyl, ethyl or propyl group that is substituted with a phenyl, methylphenyl, p-nitrophenyl, -methylnitrophenyl, p-methoxyphenyl, p-ethoxyphenyl, or p-hydroxyphenyl ring then $R^2$ is not hydrogen, an optionally substituted alkyl-, aralkyl-, cyclo-alkyl-, aryl- or heterocyclic radical or a cyano group, or if $R^1$ stands for a lower alkyl radical (for example, methyl or ethyl), an alkoxy or aryloxy group or a primary, secondary or tertiary amino group, then $R^2$ is not a lower alkyl radical (for example, a methyl or ethyl group) or a phenyl, —$CH_2$-phenyl or methylphenyl, as well as their solvates, hydrates, stereoisomers, diastereomers, enantiomers and salts.

The above-described disclaimer was introduced based on the prior art below.

A pyrazolopyridine with $R^1$=methyl and $R^2$=methyl is described by, for example, Kaupp., G. et al. 2003, European Journal of Organic Chemistry, (8) pp. 1545-1551, Gamal, A., 1994, Zagazig Journal of Pharmaceutical Sciences, 3(2) 148-53, Kalme, Z. A. et al., 1992, Khimiya Geterotsiklicheskikh Soedinenii, (9), 1218-22, El-Dean, A. M. Kamal et al., 1991, Bulletin of the Faculty of Science, Assiut University, 20(1), 15-21 or by El-Dean, A. M. et al, 1991, Indian Journal of Chemistry, 30B (9), 878-82.

A pyrazolopyridine with $R^1$=chlorophenyl and $R^2$=chlorophenyl is known by Gamal et al., 2001, Journal of Saudi Chemical Society, 5(2), pp. 183-187.

Mohamed, A. et al., 2000, Phosphorus, Sulfur and Silicon, 167, 161-179 describes pyrazolopyridines in which $R^1$=methyl and at the same time $R^2$=chlorophenyl, and $R^1$=methyl and at the same time $R^2$=furanyl. Attaby, Fawzy A. et al., 1999, Phosphorus, Sulfur and Silicon, 149, 49-64 show that these substances have antimicrobial properties.

Attaby, Fawzy A. et al., 1999, Phosphorus, Sulfur and Silicon, 155, 253-270 disclose, for example, pyrazolopyridines with antimicrobial action in which $R^1$=—CH=CH-phenyl and at the same time $R^2$=phenyl, $R^1$=—CH=CH-methoxyphenyl and at the same time $R^2$=phenyl or methoxyphenyl, $R^1$=—CH=CH-chlorophenyl and at the same time $R^2$=phenyl or chlorophenyl. Sanna, Eldin M. et al., 1998, Egyptian Journal of Pharmaceutical Sciences, 39, (1-3), 197-209 describe the same compounds and show that these substances have antibacterial properties.

Arustamova, I. S. et al., 1999, Chemistry of Heterocyclic Compounds, 35(1), 58-63 describes pyrazolopyridines in which $R^1$=methyl and at the same time $R^2$=—$CH_2$—O—$CH_3$.

Lacan, M. and Tabakovic, K. (1975) Chroatica Chemica Acta 47 (2), 127-133 disclose pyrazolopyridines in which $R^1$ stands for methyl while at the same time $R^2$ also stands for methyl.

Chandra, Sheker Reddy et al., 1997, Journal of Fluorine Chemistry, 86(2) 127-130 describes pyrazolopyridines in which $R^1$=methyl and at the same time $R^2$=methyl, $R^1$=phenyl and at the same time $R^2$=—$CF_3$, $R^2$=methylphenyl and at the same time $R^2$=—$CF_3$, $R^1$=methoxyphenyl and at the same time $R^2$=—$CF_3$, as well as R=chlorophenyl and at the same time $R^2$=—$CF_3$.

Abdel, Hafez et al., 1993, Collection of Czechoslovak Chemical Communications, 58(5), 1198-202; Deeb, Ali, 1991, Collection of Czechoslovak Chemical Communications, 56(7), 1560-3 disclose a pyrazolopyridine with $R^1$=phenyl and at the same time $R^2$=phenyl.

Gohar, Abdel Kerim et al., 1987, Archiv der Pharmazie (Weinheim, Germany), 320(9), 823-9 disclose pyrazolopyridines in which $R^2$=methyl and at the same time $R^2$=benzofuranyl that is substituted with hydroxy and/or methoxy.

Balicki, R. et al., 1979, Polish Journal of Chemistry, 53(7-8), 1515-25 describes a pyrazolopyridine in which $R^1$=methyl and at the same time $R^2$=—$CF_3$.

Pejcic, Marijan et al., 1977, Acta Pharmaceutica Jugoslavia, 27(3), 143-6 disclose pyrazolopyridines with antibacterial properties, in which $R^1$=methyl and at the same time $R^2$=—$CH_2$—O—$CH_3$, and $R^1$=—$CH_2$—O—$CH_3$ and at the same time $R^2$=methyl.

Bomika, Z. et al., 1976, Khimiya Geterotsiklicheskikh Soedinenii, (8), 1085-8 describes a pyrazolopyridine in which $R^1$=phenyl and at the same time $R^2$=phenyl, $R^1$=methyl and at the same time $R^2$=phenyl.

Yoshida, Kei et al., 1976, Yakugaku Zasshi, 96(1), 33-6 describes a pyrazolopyridine in which $R^1$=methyl and at the same time $R^2$=—$CH_2$—O—$CH_3$.

DE 30 01 498 A1 (Agfa-Gevaert AG) discloses pyrazoles that can be used for photographic materials. The patent discloses pyrazolopyridines in which $R^1$ stands for an unsubstituted alkyl, alkenyl, aryl, aralkyl or cycloalkyl group, and $R^2$ simultaneously stands for an unsubstituted alkyl, alkenyl, aryl, aralkyl or cycloalkyl group.

Described in DE 26 43 753 A1 (Dr. Karl Thomae GmbH) are pyrazolopyridines that have an antiphlogistic and in particular antithrombotic action. The disclosed substituents are always linked via a nitrogen atom to the pyridine (of the pyrazolopyridine) at 6-position.

F. E. Goda et al. 2004, Bioorganic & Medicinal Chemistry, 12(8), pp. 1845-1852 discloses pyrazolopyridines that have an antimicrobial action. In this case, $R^1$ stands for dichlorophenyl, and $R^2$ simultaneously stands for trimethoxyphenyl (compound 5b) or $R^1$ stands for bromophenyl, and $R^2$ then simultaneously stands for trimethoxyphenyl (compound 5c). Compounds 3a to 5a in Table 1 on page 1846 relate to precursors of pyrazolopyridines, but not pyrazolopyridines themselves.

Registry Number 774531-14-5 discloses a pyrazolopyridine in which $R^1$=hydroxyphenyl and at the same time $R^2$ is a piperidine. Registry Number 692775-16-9 discloses a pyrazolopyridine in which $R^1$=phenyl and at the same time $R^2$ is a methoxyphenyl. Registry Number 201224-90-0 discloses a pyrazolopyridine in which $R^1$=methoxyphenyl and at the same time $R^1$ is a —$CF_3$.

B. Narsaiah et al. 2001, Journal of Fluorine Chemistry, 109, 183-7 describes different $CF_3$-substituted pyrazolopyridines. In this case, $R^2$ stands for —$CF_3$ while $R^1$ either stands for phenyl, methylphenyl or chlorophenyl.

WO 01/19828 A2 discloses a pyrazolopyridine that is substituted with a diaminopyrazolyl- (at $R^1$-position) and a methyl group (at $R^1$-position). The diaminopyrazolyl is linked via the nitrogen atom to the pyridine (of the pyrazolopyridine) at 6-position. The substances that are described in this patent can be used as hair dyes.

German laid-open specification DE2160780 discloses pyridinopyrazoles for use as diazo components in which $R^1$ stands for phenyl or methyl and at the same time $R^2$ stands for phenyl or methyl.

German laid-open specification DE2238400 pyrazolopyridines as dyes in which $R^1$ stands for hydrogen, an optionally substituted alkyl-, aralkyl-, cycloalkyl-, or aryl radical, and $R^2$ stands for hydrogen, an optionally substituted alkyl-, aralkyl-, cyclo-alkyl-, aryl- or heterocyclic radical or a cyano group. Which substitutions may be suitable is not defined in the application. In the examples, for $R^1$, there is only one ethyl group that is substituted with a phenyl ring, a p-nitrophenyl and a p-methoxyphenyl. For $R^2$, there are no examples with substitutions. Also, for $R^2$ defined as a heterocyclic radical, there are no definitions and also no examples.

German laid-open specification DE2355967 discloses polycyclic dyes in whose production pyrazolopyridines are used in which $R^1$ stands for a lower alkyl radical (in the examples, methyl is mentioned), an alkoxy or aryloxy group or a primary, secondary or tertiary amino group, and $R^2$ simultaneously stands for a lower alkyl radical (in the examples, methyl and phenyl are mentioned for $R^2$).

None of the above-mentioned publications and patents disclose Eph-receptor inhibitors.

According to this embodiment, compounds of general formula I in a $2^{nd}$ aspect, according to claim 1, in which $R^1$ stands for $C_1$-$C_6$ alkyl or $C_3$-$C_{10}$-cycloalkyl that optionally is substituted in one or more places, in the same way or differently, with K, whereby the $C_3$-$C_{10}$-cycloalkyl optionally is interrupted by one or more —(CO)—, —SO— or —$SO_2$— groups in the ring, and optionally one or more double bonds can be contained in the ring, or for aryl, $C_3$-$C_{10}$-heterocycloalkyl or heteroaryl that optionally is substituted in one or more places, in the same way or differently, with K, whereby the $C_3$-$C_{10}$-heterocycloalkyl and/or the heteroaryl itself is interrupted by at least one nitrogen/oxygen and/or sulfur, and the $C_3$-$C_{10}$-heterocycloalkyl and/or heteroaryl can be linked only via a carbon ring atom with the pyrazolopyridine, or for a $C_3$-$C_{10}$-cycloalkyl, aryl, $C_3$-$C_{10}$-heterocycloalkyl or heteroaryl that is substituted with the group —O—$(CH_2)_n$—O—, whereby the terminal oxygen atoms of the —O—$(CH_2)_n$—O— group are linked with the same or a directly adjacent $C_3$-$C_{10}$-cycloalkyl ring-, aryl ring-, $C_3$-$C_{10}$-heterocycloalkyl ring- or heteroaryl ring-carbon atom, K stands for halogen, hydroxy or the group —$OR^3$, —$COR^4$ or for $C_3$-$C_{10}$-cycloalkyl, $C_3$-$C_{10}$-heterocycloalkyl, aryl or heteroaryl that optionally is substituted in one or more places, in the same way or differently, with L, whereby the $C_3$-$C_{10}$-heterocycloalkyl and/or the heteroaryl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, $R^2$ stands for $C_1$-$C_6$-alkyl, $C_3$-$C_{10}$-cycloalkyl, aryl or heteroaryl that optionally is substituted in one or more places, in the same way or differently, with M, whereby the heteroaryl is interrupted by at least one nitrogen, oxygen and/or sulfur, $R^3$ stands for $C_1$-$C_6$-alkyl, aryl or —$(CH_2)_n$-aryl, M stands for amino, cyano, halogen, hydroxy, nitro or for $C_1$-$C_6$-alkyl that optionally is substituted in one or more places, in the same way or differently, with amino, cyano, halogen, hydroxy, nitro, or $C_1$-$C_6$-alkoxy, or for the group —O—$C_1$-$C_6$-alkyl, —O—$(CH_2)_n$—$NR^5R^6$, —$COR^4$—O-phenyl, —O—$(CH_2)_n$-phenyl or —CO—N—$R^7$, as well as their solvates, hydrates, stereoisomers, diastereomers, enantiomers and salts, are also subjects of the invention.

According to this embodiment, compounds of general formula I in a $3^{rd}$ aspect, according to the $2^{nd}$ aspect, in which $R^1$ stands for $C_1$-$C_6$ alkyl or $C_3$-$C_{10}$-cycloalkyl that optionally is substituted in one or more places, in the same way or differently, with K, whereby the $C_3$-$C_{10}$-cycloalkyl optionally is interrupted by one or more —(CO)—, —SO— or —$SO_2$ groups in the ring, and optionally one or more double bonds can be contained in the ring, or $R^1$ stands for aryl or heteroaryl that optionally is substituted in one or more places, in the same way or differently, with K, whereby the heteroaryl itself is interrupted by at least one nitrogen, oxygen and/or sulfur, and the heteroaryl can be linked only via a carbon ring atom with the pyrazolopyridine, or $R^1$ stands for a $C_3$-$C_{10}$-cycloalkyl, aryl or heteroaryl that is substituted with the group —O—$(CH_2)_n$—O—, whereby the terminal oxygen atoms of the —O—$(CH_2)_n$—O— group are linked with the same or a directly adjacent $C_3$-$C_{10}$-cycloalkyl ring-, aryl ring- or heteroaryl ring-carbon atom, K stands for halogen, hydroxy or the group —$OR^3$, —$COR^4$ or for $C_3$-$C_{10}$-cycloalkyl, or $C_3$-$C_{10}$-heterocycloalkyl that optionally is substituted in one or more places, in the same way or differently, with L, whereby the $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, L stands for $C_1$-$C_6$-alkyl or the group —$COR^4$, —$OR^3$, $R^3$ stands for $C_1$-$C_6$-alkyl or aryl, M stands for amino, cyano, halogen, hydroxy, or nitro or for $C_1$-$C_6$-alkyl that optionally is substituted in one or more places, in the same way or differently, with amino, cyano, halogen, hydroxy, nitro, or $C_1$-$C_6$-alkoxy, or for the group —O—$C_1$-$C_6$-alkyl, —O—$(CH_2)_n$—$NR^5R^6$, —CO—$C_1$-$C_6$-alkyl, —O-phenyl, —O—$(CH_2)_n$-phenyl or —CO—N—$R^7$, as well as their solvates, hydrates, stereoisomers, diastereomers, enantiomers and salts, are another subject of this invention.

According to this embodiment, compounds of general formula I in a 4th aspect, according to the 3rd aspect, in which R$^1$ stands for $C_1$-$C_6$ alkyl, $C_3$-$C_{10}$-cycloalkyl that optionally is substituted in one or more places, in the same way or differently, with K, whereby the $C_3$-$C_{10}$-cycloalkyl optionally is interrupted by one or more —(CO)— groups in the ring, or for aryl or heteroaryl that optionally is substituted in one or more places, in the same way or differently, with K, whereby the heteroaryl itself is interrupted by at least one nitrogen, and the heteroaryl can be linked only via a carbon ring atom with the pyrazolopyridine, or for a $C_3$-$C_{10}$-cycloalkyl, aryl or heteroaryl that is substituted with the group —O—$(CH_2)_n$—O—, whereby the terminal oxygen atoms of the —O—$(CH_2)_n$—O— group are linked to the same or a directly adjacent $C_3$-$C_{10}$-cycloalkyl ring-, aryl ring- or heteroaryl ring-carbon atom, K stands for halogen, hydroxy or for the group —OR$^3$, or $C_3$-$C_{10}$-heterocycloalkyl that optionally is substituted in one or more places, in the same way or differently, with L, whereby the $C_3$-$C_{10}$-heterocycloalkyl itself is interrupted by at least one of the following atoms nitrogen and/or oxygen in the ring, L stands for $C_1$-$C_6$-alkyl or —COO—$C_1$-$C_6$-alkyl, R$^2$ stands for $C_1$-$C_6$ alkyl, $C_3$-$C_6$-cycloalkyl, aryl or heteroaryl that optionally is substituted in one or more places, in the same way or differently, with M, whereby the heteroaryl is interrupted by at least one nitrogen, M stands for amino, cyano, halogen, hydroxy, nitro or for $C_1$-$C_6$-alkyl that optionally is substituted in one or more places, in the same way or differently, with amino, cyano, halogen, hydroxy, nitro or $C_1$-$C_6$-alkoxy, or for the group —O—$C_1$-$C_6$-alkyl, —O—$(CH_2)_n$—N($C_1$-$C_6$-alkyl)$_2$, —CO—$C_1$-$C_6$-alkyl, phenoxy, benzyloxy or —CO—N—NH$_2$, as well as their solvates, hydrates, stereoisomers, diastereomers, enantiomers and salts, are also another subject of this invention.

According to this embodiment, compounds of general formula I in a 5th aspect, according to one of aspects 1 to 4, in which M stands for amino, cyano, halogen, hydroxy, or nitro or for $C_1$-$C_6$-alkyl that optionally is substituted in one or more places, in the same way or differently, with amino, cyano, halogen, hydroxy, nitro or $C_1$-$C_6$-alkoxy, or for the group —O—$C_1$-$C_6$-alkyl, —O—$(CH_2)_n$—N($C_1$-$C_6$-alkyl)$_2$ or —CO—$C_1$-$C_6$-alkyl, as well as their solvates, hydrates, stereoisomers, diastereomers, enantiomers and salts, are another subject of this invention.

According to this embodiment, compounds of general formula I in a 6th aspect, according to the 4th aspect, in which R$^1$ stands for $C_1$-$C_6$-alkyl, $C_3$-$C_6$-cycloalkyl, cyclohexanone, 1,4-dioxa-spiro[4.5]dec-8-yl, phenyl, 1,3-benzodioxolyl or pyridinyl that optionally is substituted in one or more places, in the same way or differently, with K, K stands for halogen, hydroxy, $C_1$-$C_6$-alkoxy or morpholinyl, piperazinyl, piperidinyl, or phenoxy that optionally is substituted in one or more places, in the same way or differently, with L, R$^2$ stands for $C_1$-$C_6$-alkyl, phenyl or quinolinyl, imidazolyl, indolyl or pyridinyl that optionally is substituted in one or more places, in the same way or differently, with M, M stands for amino, cyano, halogen, hydroxy, nitro, $C_1$-$C_6$-alkyl, —CF$_3$, or for $C_1$-$C_3$-alkoxy, or for the group —CO—$C_1$-$C_6$-alkyl, —O—$(CH_2)_n$—N($C_1$-$C_6$-alkyl)$_2$, phenoxy or benzyloxy, as well as their solvates, hydrates, stereoisomers, diastereomers, enantiomers and salts, are another subject of this invention.

According to this embodiment, compounds of general formula I in a 7th aspect, according to the 6th aspect, in which R$^1$ stands for $C_3$-$C_6$ alkyl, cyclopropyl, cyclohexyl, cyclohexanone, 1,4-dioxa-spiro[4.5]dec-8-yl, phenyl, 1,3-benzodioxolyl or pyridinyl that optionally is substituted in one or more places, in the same way or differently, with K, K stands for halogen, hydroxy, or methoxy, or morpholinyl, piperazinyl, piperidinyl or phenoxy that optionally is substituted in one or more places, in the same way or differently, with L, L stands for $C_1$-$C_3$-alkyl or —COO—$C_3$-$C_5$-alkyl, R$^2$ stands for isopropyl, phenyl, quinolinyl, imidazolyl, indolyl or pyridinyl that optionally is substituted in one or more places, in the same way or differently, with M, and M stands for cyano, halogen, hydroxy, nitro, methyl, —CF$_3$ or for methoxy or for the group —CO—$C_1$-$C_3$-alkyl or —O—$(CH_2)_3$—N(methyl)$_2$, as well as their solvates, hydrates, stereoisomers, diastereomers, enantiomers and salts, are another subject of this invention.

According to this embodiment, compounds of general formula (I), in an 8th aspect, according to the 7th aspect, in which R$^1$ stands for tert-butyl, cyclopropyl, cyclohexyl, cyclohexanone, 1,4-dioxa-spiro[4.5]dec-8-yl, phenyl, 1,3-benzodioxolyl or pyridinyl that optionally is substituted in one or more places, in the same way or differently, with K, L stands for methyl or —COO-tert-butyl, R$^2$ stands for isopropyl, phenyl, quinolinyl, imidazolyl, indolyl or pyridinyl that optionally is substituted in one or more places, in the same way or differently, with M, and M stands for cyano, halogen, hydroxy, nitro, methyl, —CF$_3$ or for methoxy or for the group —CO-methyl or —O—$(CH_2)_3$—N(methyl)$_2$, as well as their solvates, hydrates, stereoisomers, diastereomers, enantiomers and salts, are another subject of this invention.

According to this embodiment, compounds of general formula (I), according to one of aspects 1 to 8, in which R$^1$ stands for $C_1$-$C_6$-alkyl, $C_2$-$C_6$-alkenyl, $C_2$-$C_6$-alkinyl, $C_3$-$C_{10}$-cycloalkyl, $C_3$-$C_{10}$-heterocycloalkyl, aryl or heteroaryl that optionally is substituted in one or more places, in the same way or differently, with K, whereby the $C_3$-$C_{10}$-heterocycloalkyl and/or the heteroaryl itself is interrupted by at least one of the following atoms nitrogen, oxygen and/or sulfur in the ring, and the $C_3$-$C_{10}$-heterocycloalkyl and/or heteroaryl can be linked only via a carbon ring atom with the pyrazolopyridine, and $C_3$-$C_{10}$-cycloalkyl and/or $C_3$-$C_{10}$-heterocycloalkyl optionally can be interrupted by one or more —(CO)—, —SO— or —SO$_2$— groups that are the same or different in the ring, and optionally one or more double bonds can be contained in the ring, or for a $C_3$-$C_{10}$-cycloalkyl, aryl, $C_3$-$C_{10}$-heterocycloalkyl or heteroaryl that can be substituted with the group —O—$(CH_2)_n$—O—, whereby the terminal oxygen atoms of the —O—$(CH_2)_n$—O— group are linked with the same or a directly adjacent $C_3$-$C_{10}$-cycloalkyl ring-, aryl ring-, $C_3$-$C_{10}$-heterocycloalkyl ring- or heteroaryl ring-carbon atom, are a subject of the invention.

According to this embodiment, compounds of general formula (I), according to one of aspects 1 to 8, in which $R^1$ stands for $C_1$-$C_6$ alkyl or $C_3$-$C_{10}$-cycloalkyl that optionally is substituted in one or more places, in the same way or differently, with K, whereby the $C_3$-$C_{10}$-cycloalkyl optionally is interrupted by one or more —(CO)—, —SO— or —$SO_2$— groups in the ring and optionally one or more double bonds can be contained in the ring, or for aryl, $C_3$-$C_{10}$-heterocycloalkyl or heteroaryl that optionally is substituted in one or more places, in the same way or differently, with K, whereby the $C_3$-$C_{10}$-heterocycloalkyl and/or the heteroaryl itself is interrupted by at least one nitrogen, oxygen and/or sulfur, and the $C_3$-$C_{10}$-heterocycloalkyl and/or heteroaryl can be linked only via a carbon ring atom with the pyrazolopyridine, or for a $C_3$-$C_{10}$-cycloalkyl, aryl, $C_3$-$C_{10}$-heterocycloalkyl or heteroaryl that is substituted with the group —O—$(CH_2)_n$—O—, whereby the terminal oxygen atoms of the —O—$(CH_2)_n$—O— group are linked with the same or a directly adjacent $C_3$-$C_{10}$-cycloalkyl ring-, aryl ring-, $C_3$-$C_{10}$-heterocycloalkyl ring- or heteroaryl ring-carbon atom, are another subject of the invention.

According to this embodiment, compounds of general formula (I), according to one of aspects 1 to 8, in which $R^1$ stands for $C_1$-$C_6$ alkyl, $C_3$-$C_{10}$-cycloalkyl that optionally is substituted in one or more places, in the same way or differently, with K, whereby the $C_3$-$C_{10}$-cycloalkyl optionally is interrupted by one or more —(CO)—, —SO— or —$SO_2$— groups in the ring, and optionally one or more double bonds can be contained in the ring, or for aryl or heteroaryl that optionally is substituted in one or more places, in the same way or differently, with K, whereby the heteroaryl itself is interrupted by at least one nitrogen, oxygen and/or sulfur, and the heteroaryl can be linked only via a carbon ring atom with the pyrazolopyridine, or for a $C_3$-$C_{10}$-cycloalkyl, aryl or heteroaryl that is substituted with the group —O—$(CH_2)_n$—O—, whereby the terminal oxygen atoms of the —O—$(CH_2)_n$—O— group are linked with the same or a directly adjacent $C_3$-$C_{10}$-cycloalkyl ring-, aryl ring- or heteroaryl ring-carbon atom, are another subject of the invention.

In another subject of the invention according to this embodiment, compounds of general formula (I), according to one of aspects 1 to 8, in which $R^1$ stands for $C_1$-$C_6$ alkyl, $C_3$-$C_{10}$-cycloalkyl that optionally is substituted in one or more places, in the same way or differently, with K, whereby the $C_3$-$C_{10}$-cycloalkyl optionally is interrupted by one or more —(CO)— groups in the ring, or for aryl or heteroaryl that optionally is substituted in one or more places, in the same way or differently, with K, whereby the heteroaryl itself is interrupted by at least one nitrogen, and the heteroaryl can be linked only via a carbon ring atom with the pyrazolopyridine, or for a $C_3$-$C_{10}$-cycloalkyl, aryl or heteroaryl that is substituted with the group —O—$(CH_2)_n$—O—, whereby the terminal oxygen atoms of the —O—$(CH_2)_n$—O— group are linked with the same or a directly adjacent $C_3$-$C_{10}$-cycloalkyl ring-, aryl ring- or heteroaryl ring-carbon atom.

According to this embodiment, compounds of general formula (I), according to one of aspects 1 to 8, in which $R^1$ stands for $C_1$-$C_6$-alkyl, $C_3$-$C_6$-cycloalkyl, cyclohexanone, 1,4-dioxa-spiro[4.5]dec-8-yl, phenyl, 1,3-benzodioxolyl or pyridinyl that optionally is substituted in one or more places, in the same way or differently, with K, are a preferred subject of the invention.

According to this embodiment, compounds of general formula (I), according to one of aspects 1 to 8, in which $R^1$ stands for $C_3$-$C_6$ alkyl, cyclopropyl, cyclohexyl, cyclohexanone, 1,4-dioxa-spiro[4.5]dec-8-yl, phenyl, 1,3-benzodioxolyl or pyridinyl that optionally is substituted in one or more places, in the same way or differently, with K, are a preferred subject of the invention.

According to this embodiment, compounds of general formula (I), according to one of aspects 1 to 8, in which $R^1$ stands for tert-butyl, cyclopropyl, cyclohexyl, cyclohexanone, 1,4-dioxa-spiro[4.5]dec-8-yl, phenyl, 1,3-benzodioxolyl or pyridinyl that optionally is substituted in one or more places, in the same way or differently, with K, are a preferred subject of the invention.

According to this embodiment, compounds of general formula (I), according to one of aspects 1 to 8, in which $R^1$ stands for $C_1$-$C_6$-alkyl that optionally is substituted in one or more places, in the same way or differently, with K, and especially preferably tert-butyl, are an especially preferred subject of the invention.

According to this embodiment, compounds of general formula (I), according to one of aspects 1 to 8, in which $R^1$ stands for $C_3$-$C_6$-cycloalkyl that optionally is substituted in one or more places, in the same way or differently, with K, and especially preferably cyclopropyl and/or cyclohexyl, are an especially preferred subject of the invention.

According to this embodiment, compounds of general formula (I), according to one of aspects 1 to 8, in which $R^1$ stands for $C_3$-$C_{10}$-cycloalkyl that optionally is substituted in one or more places, in the same way or differently, with K, which is interrupted by one or more —(CO)— groups in the ring, are an especially preferred subject of the invention. $R^1$ is then especially preferred for cyclohexanone.

According to this embodiment, compounds of general formula (I), according to one of aspects 1 to 8, in which $R^1$ stands for a $C_3$-$C_{10}$-cycloalkyl, aryl or heteroaryl that is substituted with the group —O—$(CH_2)_n$—O—, whereby the terminal oxygen atoms of the —O—$(CH_2)_n$—O— group are linked with the same or a directly adjacent $C_3$-$C_{10}$-cycloalkyl ring-, aryl ring- or heteroaryl ring-carbon atom, are an especially preferred subject of the invention. $R^1$ then especially preferably stands for 1,4-dioxa-spiro[4.5]dec-8-yl and/or 1,3-benzodioxolyl.

According to this embodiment, compounds of general formula (I), according to one of aspects 1 to 8, in which $R^1$ stands for aryl or heteroaryl that optionally is substituted in one or more places, in the same way or differently, with K, whereby the heteroaryl itself is interrupted by at least one nitrogen, and the heteroaryl can be linked only via a carbon ring atom with the pyrazolopyridine, are an especially preferred subject of the invention. $R^1$ then especially preferably stands for phenyl and/or pyridinyl.

According to this embodiment, compounds of general formula (I), according to one of aspects 1 to 8, in which $R^1$ stands for a $C_3$-$C_{10}$-heterocycloalkyl and/or heteroaryl, whereby the $C_3$-$C_{10}$-heterocycloalkyl and/or heteroaryl is linked only via a carbon ring atom with the pyrazolopyridine, are another subject of the invention.

According to this embodiment, compounds of general formula (I), according to one of aspects 1 to 8, in which $R^1$ is substituted in one or more places, in the same way or differently, with K, are an especially preferred subject of the invention. According to this embodiment, compounds of general formula (I), according to one of aspects 1 to 8, in which $R^1$ is substituted in one place with K, are an especially preferred subject of the invention.

According to this embodiment, compounds of general formula (I), according to one of aspects 1 to 8, in which K stands for halogen, hydroxy or the group —$OR^3$, —$COR^4$ or —$NR^5R^6$, or for $C_3$-$C_{10}$-cycloalkyl, $C_3$-$C_{10}$-heterocycloalkyl, aryl or heteroaryl that optionally is substituted in one or more places, in the same way or differently, with L, whereby the $C_3$-$C_{10}$-heterocycloalkyl and/or the heteroaryl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, are a subject of the invention.

According to this embodiment, compounds of general formula (I), according to one of aspects 1 to 8, in which K stands for halogen, hydroxy or the group —$OR^3$, —$COR^4$ or $C_3$-$C_{10}$-cycloalkyl, $C_3$-$C_{10}$-heterocycloalkyl, aryl or heteroaryl that optionally is substituted in one or more places, in the same way or differently, with L, whereby the $C_3$-$C_{10}$-heterocycloalkyl and/or the heteroaryl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, are another subject of this invention.

According to this embodiment, compounds of general formula (I), according to one of aspects 1 to 8, in which K stands for halogen, hydroxy or the group —$OR^3$, —$COR^4$ or for $C_3$-$C_{10}$-cycloalkyl, or $C_3$-$C_{10}$-heterocycloalkyl that optionally is substituted in one or more places, in the same way or differently, with L, whereby the $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, are another subject of this invention.

According to this embodiment, compounds of general formula (I), according to one of aspects 1 to 8, in which K stands for halogen, hydroxy or for the group —$OR^3$, or for $C_3$-$C_{10}$-heterocycloalkyl that optionally is substituted in one or more places, in the same way or differently, with L, whereby the $C_3$-$C_{10}$-heterocycloalkyl itself is interrupted by at least one of the following atoms nitrogen and/or oxygen in the ring, are a preferred subject of the invention.

According to this embodiment, compounds of general formula (I), according to one of aspects 1 to 8, in which K stands for halogen, hydroxy, $C_1$-$C_6$-alkoxy or morpholinyl, piperazinyl, piperidinyl, or phenoxy that optionally is substituted in one or more places, in the same way or differently, with L, are a preferred subject of the invention.

According to this embodiment, compounds of general formula (I), according to one of aspects 1 to 8, in which K stands for halogen, hydroxy, methoxy or morpholinyl, piperazinyl, piperidinyl or phenoxy that optionally is substituted in one or more places, in the same way or differently, with L, are a preferred subject of the invention.

According to this embodiment, compounds of general formula (I), according to one of aspects 1 to 8, in which L stands for $C_1$-$C_6$-alkyl or the group —$COR^4$, —$OR^3$ or —$NR^5R^6$, are a subject of the invention. According to this embodiment, compounds of general formula (I), according to one of aspects 1 to 8, in which L stands for $C_1$-$C_6$-alkyl or the group —$COR^4$ or —$OR^3$, are another subject of the invention.

According to this embodiment, compounds of general formula (I), according to one of aspects 1 to 8, in which L stands for $C_1$-$C_6$-alkyl or —COO—$C_1$-$C_6$ alkyl, are another subject of this invention. According to this embodiment, compounds of general formula (I), according to one of aspects 1 to 8, in which L stands for $C_1$-$C_3$-alkyl or —COO—$C_3$-$C_5$-alkyl, are a preferred subject of the invention. According to this embodiment, compounds of general formula (I), according to one of aspects 1 to 8, in which L stands for methyl or —COO-tert-butyl, are another preferred subject of the invention.

According to this embodiment, compounds of general formula (I), according to one of aspects 1 to 8, in which $R^2$ stands for $C_1$-$C_6$-alkyl, $C_3$-$C_{10}$-cycloalkyl, aryl or heteroaryl that optionally is substituted in one or more places, in the same way or differently, with M, are a subject of the invention.

According to this embodiment, compounds of general formula (I), according to one of aspects 1 to 8, in which $R^2$ stands for $C_1$-$C_6$-alkyl, $C_3$-$C_{10}$-cycloalkyl, aryl or heteroaryl that optionally is substituted in one or more places, in the same way or differently, with M, whereby the heteroaryl is interrupted by at least one nitrogen, oxygen and/or sulfur, are another subject of this invention.

According to this embodiment, compounds of general formula (I), according to one of aspects 1 to 8, in which $R^2$ stands for $C_1$-$C_6$ alkyl, $C_3$-$C_6$-cycloalkyl, aryl or heteroaryl that optionally is substituted in one or more places, in the same way or differently, with M, whereby the heteroaryl is interrupted by at least one nitrogen, are another subject of this invention.

According to this embodiment, compounds of general formula (I), according to one of aspects 1 to 8, in which $R^2$ stands for $C_1$-$C_6$-alkyl, phenyl or quinolinyl, imidazolyl, indolyl or pyridinyl that optionally is substituted in one or more places, in the same way or differently, with M, are a preferred subject of this invention.

According to this embodiment, compounds of general formula (I), according to one of aspects 1 to 8, in which $R^2$ stands for isopropyl, phenyl, quinolinyl, imidazolyl, indolyl or pyridinyl that optionally is substituted in one or more places, in the same way or differently, with M, are another preferred subject of this invention.

According to this embodiment, compounds of general formula (I), according to one of aspects 1 to 8, in which $R^2$ stands for isopropyl, phenyl, quinolinyl, imidazolyl, indolyl or pyridinyl that optionally is substituted in one or more places, in the same way or differently, with M, are another preferred subject of this invention.

According to this embodiment, compounds of general formula (I), according to one of aspects 1 to 8, in which $R^3$ stands for $C_1$-$C_6$-alkyl, aryl or —$(CH_2)_n$-aryl that optionally is substituted in one or more places, in the same way or differently, with the group —$NR^5R^6$ are a subject of the invention. According to this embodiment, compounds of general formula (I), according to one of aspects 1 to 8, in which $R^3$ stands for $C_1$-$C_6$-alkyl, aryl or —$(CH_2)_n$-aryl, are another subject of this invention. According to this embodiment, compounds of general formula (I), according to one of aspects 1 to 8, in which $R^3$ stands for $C_1$-$C_6$-alkyl or aryl, are another subject of this invention. According to this embodiment, compounds of general formula (I), according to one of aspects 1 to 8, in which $R^3$ stands for $C_1$-$C_6$-alkyl or phenyl, are a preferred subject of this invention. According to this embodiment, compounds of general formula (I), according to one of aspects 1 to 8, in which $R^3$ stands for $C_1$-$C_3$-alkyl or phenyl, are another preferred subject of this invention. According to this embodiment, compounds of general formula (I), according to one of aspects 1 to 8, in which $R^3$ stands for $C_1$-$C_3$-alkyl, are another preferred subject of this invention.

According to this embodiment, compounds of general formula (I), according to one of aspects 1 to 8, in which $R^4$ stands for hydrogen, hydroxy, $C_1$-$C_6$-alkyl or $C_1$-$C_6$-alkoxy, are a subject of the invention. According to this embodiment, compounds of general formula (I), according to one of aspects 1 to 8, in which $R^4$ stands for hydrogen, hydroxy, $C_1$-$C_3$-alkyl or $C_1$-$C_3$-alkoxy, are another subject of this invention.

According to this embodiment, compounds of general formula (I), according to one of aspects 1 to 8, in which M stands for amino, cyano, halogen, hydroxy, nitro or for $C_1$-$C_6$-alkyl, $C_2$-$C_6$-alkenyl, $C_2$-$C_6$-alkinyl that optionally is substituted in one or more places, in the same way or differently, with amino, cyano, halogen, hydroxy, nitro, $C_1$-$C_6$-alkoxy or for the group —$OR^3$, —$COR^4$, or —CO—N—$R^7$, are a subject of the invention.

According to this embodiment, compounds of general formula (I), according to one of aspects 1 to 8, in which M stands for amino, cyano, halogen, hydroxy, nitro or for $C_1$-$C_6$-alkyl that optionally is substituted in one or more places, in the same way or differently, with amino, cyano, halogen, hydroxy, nitro, or $C_1$-$C_6$-alkoxy or for the group —O—$C_1$-$C_6$-alkyl, —O—$(CH_2)_n$—$NR^5R^6$, —$COR^4$, —O-phenyl, —O—$(CH_2)_n$-phenyl or —CO—N—$R^7$, are another subject of this invention. Compounds of general formula (I), according to one of aspects 1 to 8, in which M stands for amino, cyano, halogen, hydroxy, nitro or for $C_1$-$C_6$-alkyl that optionally is substituted in one or more places, in the same way or differently, with amino, cyano, halogen, hydroxy, nitro, or $C_1$-$C_6$-alkoxy, or for the group —O—$C_1$-$C_6$-alkyl, —O—$(CH_2)_n$—$NR^5R^6$, —$COR^4$ or —CO—N—$R^7$, are another preferred subject of this invention.

According to this embodiment, compounds of general formula (I), according to one of aspects 1 to 8, in which M stands for amino, cyano, halogen, hydroxy, nitro or for $C_1$-$C_6$-alkyl that optionally is substituted in one or more places, in the same way or differently, with amino, cyano, halogen, hydroxy, nitro, $C_1$-$C_6$-alkoxy or for the group —O—$C_1$-$C_6$-alkyl, —O—$(CH_2)_n$—$NR^5R^6$, —CO—$C_1$-$C_6$-alkyl, —O-phenyl, O—$(CH_2)_n$-phenyl or —CO—N—$R^7$, are another subject of this invention. According to this embodiment, compounds of general formula (I), according to one of aspects 1 to 8, in which M stands for amino, cyano, halogen, hydroxy, nitro or for $C_1$-$C_6$-alkyl that optionally is substituted in one or more places, in the same way or differently, with amino, cyano, halogen, hydroxy, nitro, or $C_1$-$C_6$-alkoxy or for the group —O—$C_1$-$C_6$-alkyl, —O—$(CH_2)_n$—$NR^5R^6$, —CO—$C_1$-$C_6$-alkyl or —CO—N—$R^7$ are another preferred subject of this invention.

According to this embodiment, compounds of general formula (I), according to one of aspects 1 to 8, in which M stands for amino, cyano, halogen, hydroxy, or nitro or for $C_1$-$C_6$-alkyl that optionally is substituted in one or more places, in the same way or differently, with amino, cyano, halogen, hydroxy, nitro or $C_1$-$C_6$-alkoxy, or for the group —O—$C_1$-$C_6$-alkyl, —O—$(CH_2)_n$—$N(C_1$-$C_6$-alkyl)$_2$, —CO—$C_1$-$C_6$-alkyl, phenoxy, benzyloxy or —CO—N—$NH_2$, are another subject of this invention. According to this embodiment, compounds of general formula (I), according to one of aspects 1 to 8, in which M stands for amino, cyano, halogen, hydroxy, or nitro or for $C_1$-$C_6$-alkyl that optionally is substituted in one or more places, in the same way or differently, with amino, cyano, halogen, hydroxy, nitro or $C_1$-$C_6$-alkoxy, or for the group —O—$C_1$-$C_6$-alkyl, —O—$(CH_2)_n$—$N(C_1$-$C_6$-alkyl)$_2$, —CO—$C_1$-$C_6$-alkyl or —CO—N—$NH_2$, preferably without —CO—N—$NH_2$, are another preferred subject of this invention.

According to this embodiment, compounds of general formula (I), according to one of aspects 1 to 8, in which M also stands for amino, cyano, halogen, hydroxy, nitro, $C_1$-$C_6$-alkyl, —$CF_3$, or for $C_1$-$C_3$-alkoxy or for the group —CO—$C_1$-$C_6$-alkyl, —O—$(CH_2)_n$—$N(C_1$-$C_6$-alkyl)$_2$, phenoxy or benzyloxy, are another preferred subject of this invention. According to this embodiment, compounds of general formula (I), according to one of aspects 1 to 8, in which M stands for amino, cyano, halogen, hydroxy, nitro, $C_1$-$C_6$-alkyl, —$CF_3$, or for $C_1$-$C_3$-alkoxy, or for the group —CO—$C_1$-$C_6$-alkyl or —O—$(CH_2)_n$—$N(C_1$-$C_6$-alkyl)$_2$, are another preferred subject of this invention.

According to this embodiment, compounds of general formula (I), according to one of aspects 1 to 8, in which M stands for cyano, halogen, hydroxy, nitro, methyl, —$CF_3$ or for methoxy or for the group —CO—$C_1$-$C_3$-alkyl or —O—$(CH_2)_3$—N(methyl)$_2$ are another preferred subject of this invention.

According to this embodiment, compounds of general formula (I), according to one of aspects 1 to 8, in which M also stands for cyano, halogen, hydroxy, nitro, methyl, —$CF_3$ or for methoxy or for the group —CO-methyl or —O—$(CH_2)_3$—N(methyl) are another preferred subject of this invention.

According to this embodiment, compounds of general formula (I), according to one of aspects 1 to 8, in which $R^2$ according to general formula (I) is substituted in one or more places, in the same way or differently, with M, are another subject of this invention. Compounds of general formula (I), according to one of aspects 1 to 8, in which $R^2$ is an aryl or heteroaryl, and the aryl or heteroaryl is substituted in one or more places, in the same way or differently, with M, are another subject of this invention. Compounds of general formula (I), according to one of aspects 1 to 8, in which $R^2$ is an aryl or heteroaryl, and the aryl or heteroaryl is substituted in one or more places, in the same way or differently, and at least one time in meta-position with M, are another subject of this invention. Compounds of general formula (I), according to one of aspects 1 to 8, in which $R^2$ is an aryl, and the aryl is substituted in one or more places, in the same way or differently, and at least one time in meta-position with M, are another preferred subject of this invention. Compounds of general formula (I), according to one of aspects 1 to 8, in which $R^2$ is a phenyl and is substituted in one or more places, in the same way or differently, and at least one time in meta-position with M, are another preferred subject of this invention. Compounds of general formula (I), according to one of aspects 1 to 8, in which $R^2$ is substituted in several places, in the same way or differently, and at least one time in meta-position with M, are another subject of this invention. Compounds of general formula (I), according to one of aspects 1 to 8, in which $R^2$ is substituted in several places, in the same way or differently, and twice in meta-position with M, are another preferred subject of this invention. Compounds of general formula (I), according to one of aspects 1 to 8, in which $R^2$ is the same and is substituted twice in meta-position with M, are another preferred subject of this invention. Compounds of general formula (I), according to one of aspects 1 to 8, in which $R^2$ is substituted one time in meta-position with M, are another preferred subject of this invention.

Compounds of general formula (I), according to one of aspects 1 to 8, in which $R^5$ and $R^6$, independently of one another, stand for hydrogen, $C_1$-$C_6$-alkyl or for the group —$COR^4$, are a subject of the invention. Compounds of general formula (I), according to one of aspects 1 to 8, in which $R^5$ and $R^6$, independently of one another, stand for hydrogen or $C_1$-$C_6$-alkyl, are another subject of this invention.

$R^7$ according to general formula (I), according to one of aspects 1 to 8, stands for hydrogen or $NH_2$.

According to this embodiment, compounds of general formula (I), according to one of aspects 1 to 8, in which n stands for 1 to 4, are a subject of the invention. According to this embodiment, compounds of general formula (I), according to one of aspects 1 to 8, in which n means 1 to 3, are another subject of this invention. According to this embodiment, compounds of general formula (I), according to one of aspects 1 to 8, in which n means 1 to 2, are another subject of this invention. According to this embodiment, compounds of general formula (I), according to one of aspects 1 to 8, in which n means 1, are another subject of this invention Another subject of this invention according to this embodiment is the use of the compounds of general formula I in a 9th aspect, according to one of aspects 1 to 8, whereby if
- $R^1$ stands for alkyl, alkenyl, aryl, aralkyl, cycloalkyl, or for a phenyl substituted alkyl or p-methoxyphenyl, then $R^1$ can simultaneously also stand for alkyl, alkenyl, aryl, aralkyl, cyano, a heterocyclic radical or cycloalkyl, or if
- $R^1$ stands for a lower alkyl radical, alkoxy or aryloxy, then $R^1$ can simultaneously also stand for a lower alkyl radical, for the production of a pharmaceutical agent.

Another preferred subject of this invention according to this embodiment is the use of the compounds of general formula I in a 10th aspect, according to one of aspects 1 to 8, for the production of a pharmaceutical agent.

Another subject of this invention according to this embodiment is the use of the compounds of general formula I in an 11th aspect, according to one of aspects 1 to 8, whereby if
- $R^1$ stands for methyl, then $R^2$ can simultaneously also stand for methyl, —$CH_2$—O—$CH_3$, phenyl, chlorophenyl, hydroxy- and/or methoxy-substituted benzofuranyl, —$CF_3$ or furanyl, or if
- $R^1$ stands for —$CH_2$—O—$CH_3$, then $R^2$ can simultaneously also stand for methyl, or if
- $R^1$ stands for —CH═CH-phenyl, then $R^2$ can simultaneously also stand for phenyl, or if
- $R^1$ stands for —CH═CH-chlorophenyl, then $R^2$ can simultaneously also stand for phenyl or chlorophenyl, or if
- $R^1$ stands for —CH═CH-methoxyphenyl, then $R^2$ can simultaneously also stand for phenyl or methoxyphenyl, or if
- $R^1$ stands for phenyl, then $R^1$ can simultaneously also stand for —$CF_3$, methyl, methoxyphenyl or phenyl, or if
- $R^1$ stands for methoxyphenyl, then $R^1$ can simultaneously also stand for —$CF_3$, or if
- $R^1$ stands for methylphenyl, then $R^1$ can simultaneously also stand for —$CF_3$, or if
- $R^1$ stands for chlorophenyl, then $R^2$ can simultaneously also stand for chlorophenyl or —$CF_3$, or if
- $R^1$ stands for dichlorophenyl, then $R^2$ can simultaneously also stand for trimethoxyphenyl, or if
- $R^1$ stands for bromophenyl, then $R^2$ can simultaneously also stand for trimethoxyphenyl, or if
- $R^1$ stands for alkyl, alkenyl, aryl, aralkyl, cycloalkyl, or for a phenyl -substituted alkyl or p-methoxyphenyl, then $R^2$ can simultaneously also stand for alkyl, alkenyl, aryl, aralkyl, cyano, a heterocyclic radical or cycloalkyl, or if
- $R^1$ stands for a lower alkyl radical, alkoxy, aryloxy or a primary, secondary or tertiary amino group, then $R^2$ can simultaneously also stand for a lower alkyl radical, or if
- $R^1$ stands for hydroxyphenyl, then $R^2$ can simultaneously also stand for heterocyclyl or —COO-tert-butyl-substituted heterocycloalkyl, or if
- $R^1$ stands for benzyloxyphenyl, then $R^2$ can simultaneously also stand for —COO-tert-butyl-substituted heterocycloalkyl, or if
- $R^1$ stands for a $C_3$-$C_{10}$-heterocycloalkyl or a heteroaryl, then the $C_3$-$C_{10}$-heterocycloalkyl and/or the heteroaryl can be linked via a carbon ring atom to the pyrazolopyridine, for the production of a pharmaceutical agent for treating diseases in which angiogenesis, lymphangiogenesis or vasculogenesis plays a role, vascular diseases, diseases that are caused by a hyperproliferation of body cells, as well as chronic or acute neurodegenerative diseases.

Another preferred subject of this invention according to this embodiment is the use of the compounds of general formula I in a 12th aspect, according to the 11th aspect, for the production of a pharmaceutical agent for treating diseases in which angiogenesis, lymphangiogenesis or vasculogenesis plays a role, diseases that are caused by a hyperproliferation of body cells, as well as chronic or acute neurodegenerative diseases.

Another preferred subject of this invention according to this embodiment is the use of the compounds of general formula I in a 13th aspect, according to one of aspects 1 to 8, for the production of a pharmaceutical agent for treating diseases in which angiogenesis, lymphangiogenesis or vasculogenesis plays a role, vascular diseases, diseases that are caused by a hyperproliferation of body cells, as well as chronic or acute neurogenerative diseases.

Another subject of this invention according to this embodiment is the use of the compounds of general formula I in a 14th aspect, according to one of aspects 1 to 8, for diagnostic purposes in vitro or in vivo for identifying receptors in tissues by means of autoradiography or PET.

The intermediate products that are preferably used for the production of the compounds of general formula (I) according to the invention in a 15th aspect, according to one of aspects 1 to 8, according to this embodiment of the invention, are the following compounds:

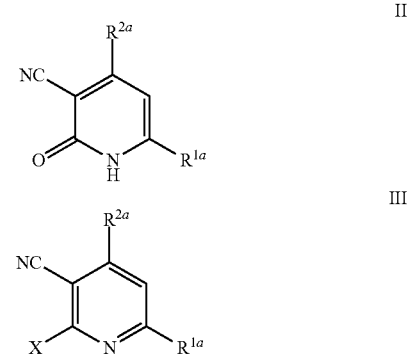

in which
X stands for halogen or —O—$SO_2$—$C_mF_{2m+1}$, preferably for perfluoroalkylsulfonyl,
m stands for 1 to 4, and
$R^{1a}$ and $R^{2a}$ have the same meaning as $R^1$ and $R^2$, according to one of aspects 1 to 8, whereby K, however, also can stand for group —$COR^4$, and $R^3$ also can stand for the group trimethylsilyl (TMS), tert-butyl-dimethylsilyl (TBDMS), tert-butyl-diphenylsilyl (TBDPS), triethylsilyl (TES), $C_1$-$C_2$-alkyl, $C_3$-$C_6$-allyl, benzyl or for the group —$COR^{4a}$,
as well as their solvates, hydrates, stereoisomers, diastereomers, enantiomers and salts as intermediate products for the production of compounds of general formula (I).

Another subject of the invention according to this embodiment is the use of the compounds of general formulas (II) and/or (III) in a $16^{th}$ aspect, according to the $15^{th}$ aspect, as intermediate products for the production of compounds of general formula (I).

According to this embodiment, pharmaceutical agents in a $17^{th}$ aspect, which contain at least one compound of general formula I according to one of aspects 1 to 8, whereby if
  $R^1$ stands for alkyl, alkenyl, aryl, aralkyl, or cycloalkyl, or for a phenyl; substituted alkyl or p-methoxyphenyl, then $R^2$ can also simultaneously stand for alkyl, alkenyl, aryl, aralkyl, cyano, a heterocyclic radical or cycloalkyl,
  $R^1$ stands for a lower alkyl radical, alkoxy, aryloxy, or a primary, secondary or tertiary amino group, then $R^2$ can also simultaneously stand for a lower alkyl radical,
are another subject of the invention.

According to this embodiment, pharmaceutical agents in aspect 18 that contain at least one compound of general formula I according to one of aspects 1 to 8 are another preferred subject of the invention.

According to this embodiment, compounds according to aspects 1 to 8 or pharmaceutical agents according to aspects 17 or 18 with suitable formulation substances and vehicles in aspect 19 are another preferred subject of the invention.

Alkyl is defined in each case as a straight-chain or branched alkyl radical, such as, for example, methyl, ethyl, propyl, isopropyl, butyl, isobutyl, sec-butyl, tert-butyl, pentyl, isopentyl, hexyl, heptyl, octyl, nonyl and decyl.

The alkyl group of $R^1$ has the meaning that is mentioned in the paragraph above, but $C_1$-$C_6$-alkyl groups are preferred. Preferred for the alkyl group $R^1$ are $C_1$-$C_5$-alkyl groups, still more preferred are $C_3$-$C_5$-alkyl groups, and especially preferred is a $C_4$-alkyl group, in particular a tert-butyl group. Alkyl group $R^2$ has the meaning that is mentioned in the paragraph above, but $C_1$-$C_6$-alkyl groups are preferred, $C_2$-$C_4$-alkyl groups are especially preferred, and a $C_3$-alkyl group, in particular an isopropyl group, is quite especially preferred. Alkyl groups $R^3$, $R^4$, $R^5$, $R^6$, L and M have the meaning that is mentioned in the paragraph above, but $C_1$-$C_6$-alkyl groups are preferred, $C_1$-$C_3$-alkyl groups are especially preferred, and a methyl group is quite especially preferred.

Alkoxy is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy or decyloxy.

The alkoxy groups K, $R^4$ and M have the meaning that is mentioned in the paragraph above, but $C_1$-$C_6$-alkoxy groups are preferred, $C_1$-$C_3$-alkoxy groups are especially preferred, and a methoxy group is especially preferred.

The alkenyl substituents are in each case straight-chain or branched, whereby, for example, the following radicals are meant: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl, or allyl.

Alkinyl is defined in each case as a straight-chain or branched alkinyl radical that contains 2-6, preferably 2-4, C atoms. For example, the following radicals can be mentioned: acetylene, propin-1-yl, propin-3-yl, but-1-in-1-yl, but-1-in-4-yl, but-2-in-1-yl, but-1-in-3-yl, etc.

Heterocyclyl or $C_3$-$C_{10}$-heterocycloalkyl stands for an alkyl ring that comprises 3-10 carbon atoms, preferably for an alkyl ring that comprises 3 to 10 carbon atoms, and especially preferably for an alkyl ring that comprises 5 to 6 carbon atoms, and said alkyl ring is interrupted by at least one of the following atoms nitrogen, oxygen and/or sulfur in the ring, and optionally can be interrupted by one or more —(CO)—, —SO— or —SO$_2$— groups that are the same or different in the ring, and optionally one or more double bonds can be contained in the ring. Only those combinations are meant, however, that are useful from the viewpoint of one skilled in the art, in particular in reference to ring strain.

As heterocyclyls, there can be mentioned, e.g.: oxiranyl, oxethanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl, etc.

Cycloalkyls are defined as monocyclic $C_3$-$C_{10}$ alkyl rings, such as cyclopropyl, cyclobutyl, cyclopentyl, cyclohexyl or cycloheptyl, but also bicyclic rings or tricyclic rings, such as, for example, adamantanyl, and in the first embodiment of this invention. The cycloalkyl rings can be unsubstituted or substituted in one or more places. Cycloalkyls, according to this embodiment of the invention, contain $C_3$-$C_{10}$ hydrocarbon atoms; cycloalkyls with $C_3$-$C_6$-hydrocarbon atoms are preferred.

An aryl radical in each case has 6-12 carbon atoms, such as, for example, naphthyl, biphenyl and in particular phenyl. The radical can be monocyclic or bicyclic, for example naphthyl, biphenyl and in particular phenyl.

The heteroaryl radical in each case comprises 3-16 ring atoms, preferably 5 to 10 ring atoms, and especially preferably 5 to 7 ring atoms, and instead of carbon contains one or more of the heteroatoms that are the same or different from the group oxygen, nitrogen or sulfur, can be monocyclic, bicyclic or tricyclic, and in addition in each case can be benzocondensed. Only those combinations are meant, however, that are useful from the viewpoint of one skilled in the art, in particular in reference to ring strain.

The heteroaryl rings can be unsubstituted or substituted in one or more places.

For example, there can be mentioned: thienyl, furanyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl as well as benzo derivatives thereof, such as, e.g., benzofuranyl, benzothienyl, benzoxazolyl, benzimidazolyl, indazolyl, indolyl, isoindolyl, oxepinyl, azocinyl, indolizinyl, indolyl, isoindolyl, indazolyl, benzimidazolyl, purinyl, or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, etc.

Halogen is defined in each case as fluorine, chlorine, bromine or iodine. A fluorine, chlorine or bromine atom is preferred. The fluorine atom and the chlorine atom are especially preferred.

As used in this application, for example in connection with the definition of "$C_1$-$C_6$-alkyl", "$C_1$-$C_6$" refers to an alkyl group with a finite number of 1 to 6 carbon atoms, i.e., 1, 2, 3, 4, 5, or 6 carbon atoms. In addition, the definition of "$C_1$-$C_6$" is interpreted such that any possible partial area, such as, for example, $C_1$-$C_6$, $C_2$-$C_6$, $C_3$-$C_6$, $C_4$-$C_6$, $C_5$-$C_6$, $C_1$-$C_2$, $C_1$-$C_3$, $C_1$-$C_4$, $C_1$-$C_5$, $C_1$-$C_6$, is co-contained.

Analogously thereto, "$C_2$-$C_6$," for example in connection with the definition of "$C_2$-$C_6$-alkenyl" and "$C_2$-$C_6$-alkinyl," refers to an alkenyl group or an alkinyl group with a finite number of 2 to 10 carbon atoms, i.e., 2, 3, 4, 5 or 6 carbon atoms. The definition of "$C_2$-$C_6$" is interpreted such that any possible partial area, such as, for example $C_2$-$C_6$, $C_3$-$C_6$, $C_4$-$C_6$, $C_5$-$C_6$, $C_2$-$C_3$, $C_2$-$C_4$, $C_2$-$C_8$, $C_2$-$C_6$, preferably $C_2$-$C_4$, is co-contained.

In addition, "$C_1$-$C_6$," for example in connection with the definition of "$C_1$-$C_6$-alkoxy," refers to an alkoxy group with a finite number of 1 to 6 carbon atoms, i.e., 1, 2, 3, 4, 5 or 6 carbon atoms. The definition of "$C_1$-$C_6$" is interpreted such that any possible partial area, such as, for example, $C_1$-$C_6$, $C_2$-$C_8$, $C_3$-$C_4$, $C_1$-$C_2$, $C_1$-$C_3$, $C_1$-$C_4$, $C_1$-$C_5$, $C_1$-$C_6$, is co-contained in the definition.

All area information of the application not explicitly cited here is defined analogously to the areas "$C_1$-$C_6$," "$C_2$-$C_6$," and "$C_1$-$C_6$" that are mentioned above by way of example.

The above-cited definitions relate to the compounds of general formula (I). The definitions are not such that they can be used for interpretation of the excluded (disclaimed) prior art. If, for example, a cycloalkyl is mentioned in the prior art that is cited here, cycloalkyl is not defined such that substituted cycloalkyl could also be co-contained (as mentioned in this application in the case of the definitions on page 32, lines 13 to 18, in particular line 16). The definition of this cycloalkyl depends solely on the original document of the prior art made available to the public.

The Following Information Relates Equally To The Two Embodiments Of The Invention Isomers are defined as chemical compounds of the same summation formula but of different chemical structure. In general, constitutional isomers and stereoisomers are distinguished.

Constitutional isomers have the same summation formula, but are distinguished by the way in which their atoms or atom groups are linked. These include functional isomers, position isomers, tautomers or valence isomers.

Stereoisomers basically have the same structure (constitution)—and thus also the same summation formula—but are distinguished by the spatial arrangement of the atoms. In general, configuration isomers and conformation isomers are distinguished. Configuration isomers are stereoisomers that can be converted into one another only by bond breaking. These include enantiomers, diastereomers and E/Z (cis/trans) isomers. Enantiomers are stereoisomers that behave toward one another like image and mirror image and do not have any plane of symmetry. All stereoisomers that are not enantiomers are referred to as diastereomers. E/Z (cis/trans) isomers on double bonds are a special case. Conformation isomers are stereoisomers that can be converted into one another by the rotation of single bonds.

To differentiate the types of isomerism from one another, see also the IUPAC Rules, Section E (Pure Appl. Chem. 45, 11-30, 1976).

The compounds of general formula I according to the invention also contain the possible tautomeric forms and comprise the E or Z isomers, or, if a chiral center is present, also the racemates and enantiomers. Double-bond isomers are also defined among the latter.

The compounds according to the invention can also be present in the form of solvates, in particular of hydrates, whereby the compounds according to the invention consequently contain polar solvents, in particular water, as structural elements of the crystal lattice of the compounds according to the invention. The proportion of polar solvent, in particular water, can be present in a stoichiometric or else unstoichiometric ratio. In the case of stoichiometric solvates, hydrates, we also speak of hemi- (semi), mono-, sesqui-, di-, tri-, tetra-, penta-, etc., solvates or hydrates.

If an acid group is included, the physiologically compatible salts of organic and inorganic bases are suitable as salts, such as, for example, the readily soluble alkali and alkaline-earth salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-aminomethane, aminopropanediol, Sovak base, or 1-amino-2,3,4-butanetriol.

If a basic group is included, the physiologically compatible salts of organic and inorganic acids, such as hydrochloric acid, sulfuric acid, phosphoric acid, citric acid, tartaric acid, i.a., are suitable.

Functional groups can optionally be protected by protective groups during the reaction sequence. Such protective groups can be, i.a., esters, amides, ketals/acetals, nitro groups, carbamates, alkyl ethers, allyl ethers, benzyl ethers or silyl ethers. As components of silyl ethers, i.a., the following compounds, such as, e.g., trimethylsilyl (TMS), tert-butyl-dimethylsilyl (TBDMS), tert-butyl-diphenylsilyl (TBDPS), triethylsilyl (TES), etc., can occur. Their production is described in the experimental part.

The compounds of general formula I according to the invention inhibit protein tyrosine kinases, in particular Eph receptors, and this also accounts for their action in, for example, the treatment of diseases, in which angiogenesis, lymphangiogenesis or vasculogenesis plays a role, vascular diseases, diseases that are caused by hyperproliferation of body cells or chronic or acute neurodegenerative diseases. These compounds of general formula (I) of the two embodiments of the invention can accordingly be used for the production of a pharmaceutical agent. These compounds of general formula (I) of the two embodiments of the invention can also be used in particular for the production of a pharmaceutical agent for treating the above-cited diseases.

Treatments are performed preferably on humans but also on related mammal species such as, e.g., dogs and cats.

Angiogenic and/or vasculogenic diseases can be treated by the growth of the blood vessels being inhibited (antiangiogenic) or promoted (proangiogenic). Antiangiogenic uses are carried out, e.g., in the case of tumor angiogenesis, endometriosis, in diabetes-induced or other retinopathies or in age-related macular degeneration.

Proangiogenic uses are carried out in, e.g., myocardial infarction or acute neurodegenerative diseases by ischemias of the brain or neurotraumas.

Vascular diseases are defined as stenoses, arterioscleroses, restenoses or inflammatory diseases, such as rheumatic arthritis.

Hyperproliferative diseases are defined as solid tumors, non-solid tumors or non-carcinogenic cell hyperproliferation, whereby solid tumors are defined as, i.a., breast tumors, colon tumors, kidney tumors, lung tumors and/or brain tumors. Non-solid tumors are defined as, i.a., leukemias, and non-carcinogenic cell hyperproliferation is defined as psoriasis, eczema, and scleroderma in the skin or benign hypertrophy of the prostate.

Chronic neurodegenerative diseases are defined as, i.a., Huntington's disease, amyotrophic lateral sclerosis, Parkinson's disease, AIDS-induced dementia or Alzheimer's disease.

Use of the compounds of general formula I according to the two embodiments of the invention can also be used for diagnostic purposes in vitro or in vivo for identifying corresponding receptors in tissues by means of autoradiography and/or PET.

In particular, the substances can also be radiolabeled for diagnostic purposes.

To use the compounds according to the invention as pharmaceutical agents, the latter are brought into the form of a pharmaceutical preparation, which in addition to the active ingredient for enteral or parenteral application contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories or capsules, or in liquid form, for example as solutions, suspensions or emulsions. They optionally contain, moreover, adjuvants, such as preservatives, stabilizers, wetting agents or emulsifiers, salts for changing the osmotic pressure, or buffers.

These pharmaceutical preparations are also subjects of this invention.

For parenteral application, in particular injection solutions or suspensions, in particular aqueous solutions of the active compounds in polyhydroxyethoxylated castor oil, are suitable.

As carrier systems, surface-active adjuvants, such as salts of bile acids or animal or plant phospholipids, but also mixtures thereof as well as liposomes or their components, can also be used.

For oral application, in particular tablets, coated tablets or capsules with talc and/or hydrocarbon vehicles or hydrocarbon binders, such as, for example, lactose, corn or potato starch, are suitable. The application can also be carried out in liquid form, such as, for example, as a juice, to which optionally a sweetener is added.

The enteral, parenteral and oral applications are also subjects of this invention.

The dosage of the active ingredients can vary depending on the method of administration, age and weight of the patient, type and severity of the disease to be treated and similar factors. The daily dose is 0.5-1,000 mg, whereby the dose can be given as an individual dose to be administered once or divided into two or more daily doses.

Pharmaceutical agents for treating the above-cited diseases that preferably contain at least one compound according to general formula (I), as well as pharmaceutical agents with suitable formulation substances and vehicles, are also subjects of the two embodiments of this invention.

If the production of the starting compounds is not described, the latter are known to one skilled in the art or can be produced analogously to known compounds or processes that are described here. It is also possible to perform all reactions described here in parallel reactors or by means of combinatory operating procedures.

According to commonly used methods, such as, for example, crystallization, chromatography or salt formation, the isomer mixtures can be separated into enantiomers or E/Z isomers.

The production of salts is carried out in the usual way by a solution of the compound of formula I being mixed with the equivalent amount of or an excess of a base or acid, which optionally is in solution, and the precipitate being separated, or the solution being worked up in the usual way.

Production of the Compounds of the Invention According to the Two Embodiments of the Invention

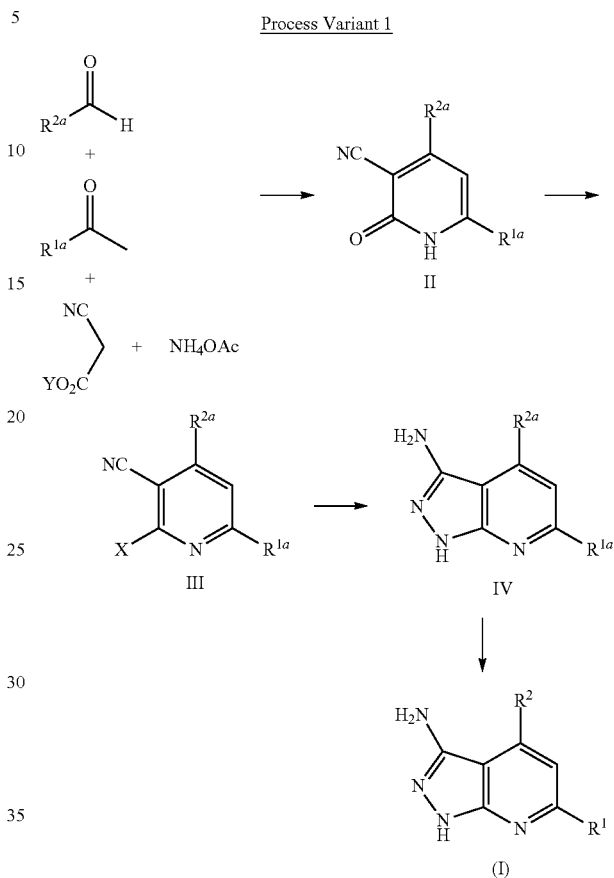

Y stands for a $C_1$-$C_6$-alkyl radical, and X stands for halogen or perfluoroalkylsulfonyl.

In the two embodiments, substituents $R^{1a}$ and $R^{2a}$ have the meaning that is described in general formulas II and III.

Substituents $R^1$ and $R^2$ have the meaning that is described in general formula I.

The production of the compounds of general formula I is carried out in the way shown in process variant I. By reaction of aldehyde $R^{2a}$—CHO with the methylketone $R^{1a}C(O)CH_3$, cyanoacetic acid ester as well as ammonium acetate, first the pyridones of general formula II are produced. Compounds of general formula II are then converted into the compounds of general formula III, in which X has the meaning of halogen or perfluoroalkylsulfonyl. The addition of hydrazine to compounds of general formula III ultimately results in compounds of general formula IV, from which then the compounds of general formula I can be produced optionally by further modifications of radicals $R^{1a}$ and $R^{2a}$. These modifications contain, e.g., the cleavage of protective groups, but also substitutions, additions, e.g., of carbonyl groups or nitrites, alkylations, reductive aminations, acetylations of OH— or NH— groups and other reactions. Radicals $R^{1a}$ and $R^{2a}$ can also already correspond to later radicals $R^1$ and $R^2$, however, such that then the compounds of general formula I are produced directly by adding hydrazine to compounds of general formula III.

EXAMPLE 1

Production of 6-tert-Butyl-4-p-tolyl-1H-pyrazolo[3,4b]pyridin-3-ylamine

EXAMPLE 1a

Production of 6-tert-Butyl-2-oxo-4-p-tolyl-1,2-dihydro-pyridine-3-carbonitrile

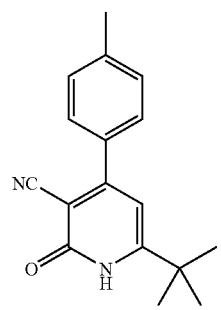

A solution of 5.13 g of ammonium acetate, 886 µl of cyanoacetic acid ethyl ester, 1.03 ml of 3,3-dimethyl-2-butanone and 1 g of 4-methylbenzaldehyde in 40 ml of ethanol is stirred for 6 hours at 80° C. Then, it is stirred for 5 more hours at 20° C. The precipitated product is filtered off. The filtrate is rewashed with ethanol and hexane. 630 mg of product is obtained.

$^1$H-NMR (CDCl$_3$): δ 1.44 (9H); 2.42 (3H); 6.30 (1H); 7.31 (2H); 7.52 (2H); 12.41 (1H) ppm.

EXAMPLE 1b

Production of 2-Bromo-6-tert-butyl-4-p-tolyl-nicotinonitrile

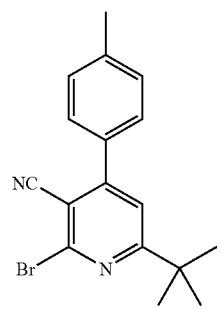

403 mg of phosphorus pentoxide and 460 mg of tetrabutylammonium bromide are added to a solution of 315 mg of the substance, described under Example 1a), in 3.5 ml of toluene. It is refluxed for one hour. After cooling, the reaction mixture is diluted with ethyl acetate. Then, it is poured into water, the phases are separated, and the aqueous phase is extracted again with ethyl acetate. The combined organic phases are washed with saturated sodium chloride solution. It is dried on sodium sulfate, and concentrated by evaporation in a vacuum. The crude product that is obtained is chromatographed on silica gel. 120 mg of product is obtained.

$^1$H-NMR (CDCl$_3$): δ=1.39 (9H); 2.43 (3H); 7.32 (3H); 7.47 (2H) ppm.

EXAMPLE 1c

Production of 6-tert-Butyl-4-p-tolyl-1H-pyrazolo[3,4b]pyridin-3-ylamine

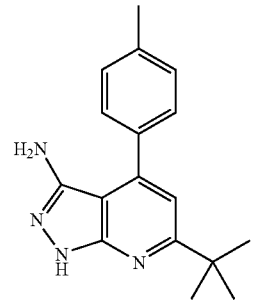

43 µl of hydrazine hydrate solution (80%) is added to a solution of 117 mg of the compound, described under Example 1b), in 2 ml of propanol. It is stirred at 100° C. for 3 more hours. Then, 22 µl of hydrazine hydrate solution (80%) is added again. It is stirred for another 1.5 hours at 100° C., and then the reaction mixture is cooled to 0° C. Then, it is allowed to stand for 3 hours at 0° C. The precipitated reaction product is suctioned off. It is rewashed with ice-cold propanol.

$^1$H-NMR (CDCl$_3$): δ=1.46 (9H); 2.44 (3H); 3.93 (2H); 7.01 (1H); 7.33 (2H); 7.48 (2H) ppm.

EXAMPLE 2

Production of 6-tert-Butyl-4-(1H-indol-3-yl)-1H-pyrazolo[3,4b]pyridin-3-ylamine

EXAMPLE 2a

Production of 6-tert-Butyl-4-(4-cyanophenyl)-2-oxo-1,2-dihydro-pyridine-3-carbonitrile

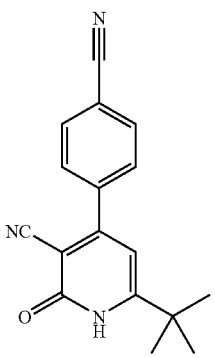

Analogously to Example 1a, 880 mg of product is obtained from 4.7 g of ammonium acetate, 812 µl of cyanoacetic acid ethyl ester, 945 µl of 3,3-dimethyl-2-butanone and 1 g of 4-cyanobenzaldehyde.

$^1$H-NMR (d6-DMSO): δ=1.31 (9H); 6.30 (1H); 7.84 (2H); 8.03 (2H); 11.30 (1H) ppm.

EXAMPLE 2b

Production of 2-Bromo-6-tert-butyl-4-(4-cyanophenyl)-nicotinonitrile

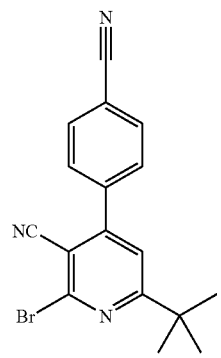

Analogously to Example 1b), 250 mg of product is obtained from 300 mg of the substance, described under Example 2a), in 5 ml of toluene with 370 mg of phosphorus pentoxide and 418 mg of tetrabutylammonium bromide.

$^1$H-NMR (CDCl$_3$): δ=1.40 (9H); 7.33 (1H); 7.68 (2H); 7.83 (2H) ppm.

EXAMPLE 2c

Production of 4-(3-Amino-6-tert-butyl-1H-pyrazolo[3,4b]pyridin-4-yl)-benzonitrile

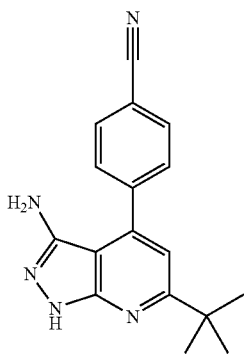

Analogously to Example 1c), 98 mg of product is produced from 200 mg of the compound that is described under Example 2b) with 71 μl of hydrazine hydrate solution (80%) in propanol.

$^1$H-NMR (d6-DMSO): δ=1.39 (9H); 4.56 (2H); 7.00 (1H); 7.80 (2H); 8.00 (2H); 12.29 (1H) ppm.

EXAMPLE 3

Production of 6-tert-Butyl-4-(1H-indol-3-yl)-1H-pyrazolo[3,4b]pyridin-3-ylamine

EXAMPLE 3a

Production of 6-tert-Butyl-4-(4-cyanophenyl)-2-oxo-1,2-dihydro-pyridine-3-carbonitrile

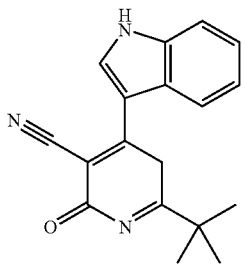

Analogously to Example 1a), 240 mg of product is obtained from 4.25 g of ammonium acetate, 733 μl of cyanoacetic acid ethyl ester, 852 μl of 3,3-dimethyl-2-butanone and 1 g of 3-indole carbaldehyde.

$^1$H-NMR (d6-DMSO): δ=1.32 (9H); 6.50 (1H); 7.20 (2H); 7.53 (1H); 7.72 (2H); 8.09 (1H); 11.98 (2H) ppm.

EXAMPLE 3b

Production of 6-tert-Butyl-3-cyano-4-(1H-indol-3-yl)-2-trifluoromethane-sulfonyl pyridine

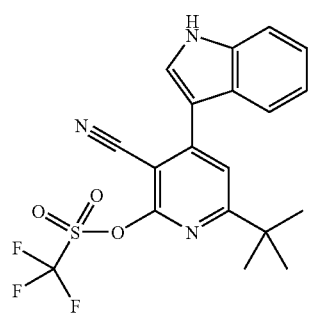

206 μl of trifluoromethanesulfonic acid anhydride is added in drops to a solution of 200 mg of the compound, described under Example 3a), in 4 ml of pyridine at 0° C. It is allowed to stir for 3 more hours at 0° C., and then another 100 μof trifluoroacetic acid anhydride is added. It is stirred for another 1.5 hours at 0° C. Then, the reaction mixture is poured into saturated sodium bicarbonate solution. It is extracted with ethyl acetate, the organic phase is washed with saturated sodium chloride solution, dried on sodium sulfate, and concentrated by evaporation in a vacuum. After column chromatography on silica gel, 116 mg of product is obtained.

$^1$H-NMR (d6-DMSO): δ=1.34 (9H); 6.50 (1H); 7.20 (2H); 7.54 (1HH); 7.75 (1H); 8.08 (1H); 12.00 (2H) ppm.

EXAMPLE 3c

Production of 6-tert-Butyl-4-(1H-indol-3-yl)-1H-pyrazolo[3,4b]pyridin-3-ylamine

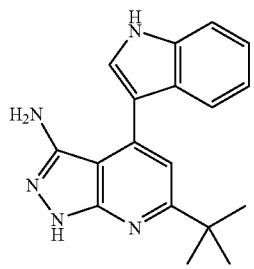

Analogously to Example 1c), 75 mg of product is produced from 190 mg of the compound that is described under Example 3b) with 55 µl of hydrazine hydrate solution (80%) in propanol.

$^1$H-NMR (d6-DMSO): δ=1.40 (9H); 4.55 (2H); 7.04 (1H); 7.80 (2H); 8.01 (2H); 12.39 (1H) ppm.

EXAMPLE 4

Production of 6-tert-Butyl-4-(4-phenoxyphenyl)-1H-pyrazolo[3,4b]-pyridin-3-ylamine

EXAMPLE 4a

Production of 6-tert-Butyl-2-oxo-4-(4-phenoxyphenyl)-1,2-dihydro-pyridine-3-carbonitrile

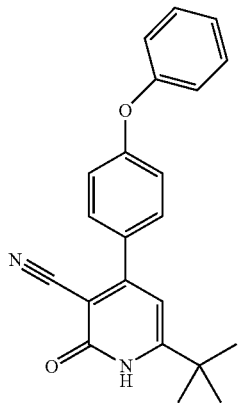

Analogously to Example 1a), 510 mg of product is obtained from 3.11 g of ammonium acetate, 540 µl of cyanoacetic acid ethyl ester, 624 µl of 3,3-dimethyl-2-butanone and 883 µl of 4-phenoxybenzaldehyde.

$^1$H-NMR: (d6-DMSO): δ=1.30 (9H); 6.27 (1H); 7.13 (4H); 7.20 (1H); 7.45 (2H); 7.70 (2H); 12.20 (1H) ppm.

EXAMPLE 4b

Production of 6-tert-Butyl-3-cyano-4-(4-phenoxyphenyl)-2-trifluoromethanesulfonyl pyridine

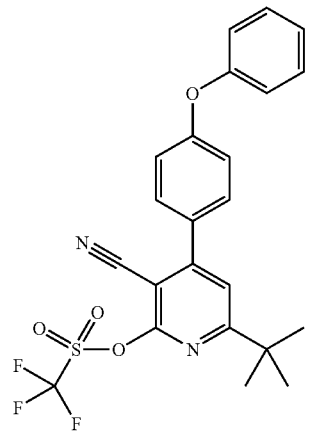

Analogously to Example 3b), 138 mg of product is obtained from 150 mg of the substance, described under Example 4a), and 162 µl of trifluoromethanesulfonic acid anhydride in pyridine.

$^1$H-NMR (CDCl$_3$): δ=1.39 (9H); 7.11 (4H); 7.24 (1H); 7.41 (3H); 7.59 (2H) ppm.

EXAMPLE 4c 6-tert-Butyl-4-(4-phenoxyphenyl)-1H-pyrazolo[3,4b]pyridin-3-ylamine

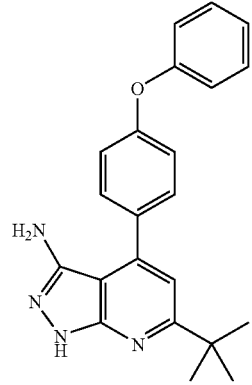

Analogously to Example 3, 32 mg of product is produced from 67 mg of the compound that is described under Example 11 with 35 µl of hydrazine hydrate solution (80%) in propanol.

$^1$H-NMR (d6-DMSO): δ=1.38 (9H); 4.54 (2H); 6.98 (1H); 7.15 (5H); 7.44 (2H); 7.62 (2H), 12.16 (1H) ppm.

EXAMPLE 5

Production of 6-tert-Butyl-4-(4-benzyloxyphenyl)-1H-pyrazolo[3,4b]pyridin-3-ylamine

EXAMPLE 5a

Production of 4-(4-Benzyloxyphenyl)-6-tert-butyl-2-oxo-1,2-dihydro-pyridine-3-carbonitrile

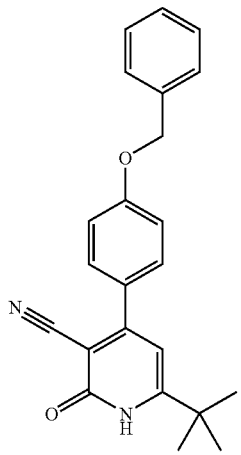

Analogously to Example 1a), 613 mg of product is obtained from 2.91 g of ammonium acetate, 500 µl of cyanoacetic acid ethyl ester, 585 µl of 3,3-dimethyl-2-butanone and 1 g of 4-benzyloxybenzaldehyde.

$^1$H-NMR (d6-DMSO): δ=1.30 (9H); 5.20 (2H); 6.22 (1H); 7.18 (2H); 7.30-7.50 (5H); 7.65 (1H); 12.18 (1H) ppm.

EXAMPLE 5b

Production of 6-tert-Butyl-3-cyano-4-(4-benzyloxyphenyl)-2-trifluoromethanesulfonyl pyridine

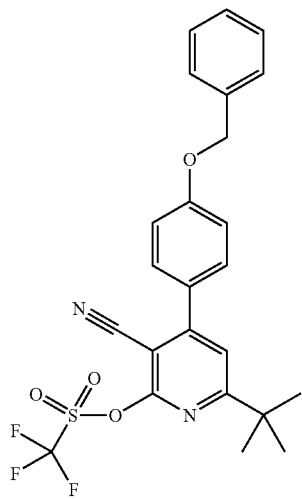

Analogously to Example 3b), 288 mg of product is obtained from 250 mg of the substance that is described under Example 5a) and 258 µl of trifluoromethanesulfonic acid anhydride in pyridine.

$^1$H-NMR (CDCl$_3$): δ=1.38 (9H); 5.16 (2H); 7.13 (2H); 7.32-7.50 (6H); 7.59 (2H) ppm.

EXAMPLE 5c

Production of 6-tert-Butyl-4-(4-benzyloxyphenyl)-1H-pyrazolo[3,4b]-pyridin-3-ylamine

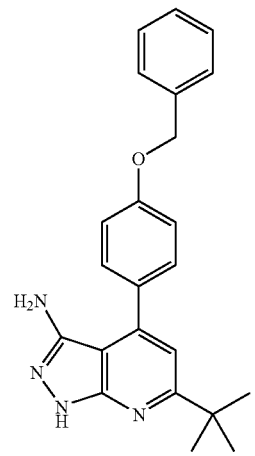

Analogously to Example 1c), 159 mg of product is produced from 284 mg of the compound that is described under Example 5b) with 70 µl of hydrazine hydrate solution (80%) in propanol.

$^1$H-NMR (d6-DMSO): δ=1.38 (9H); 4.50 (2H); 5.19 (2H); 6.93 (1H); 7.19 (2H); 7.30-7.58 (7H); 12.12 (1H) ppm.

EXAMPLE 6

Production of 6-tert-Butyl-4-(3-methoxyphenyl)-1H-pyrazolo[3,4b]-pyridin-3-ylamine

EXAMPLE 6a

Production of 6-tert-Butyl-4-(3-methoxyphenyl)-2-oxo-1,2-dihydro-pyridine-3-carbonitrile

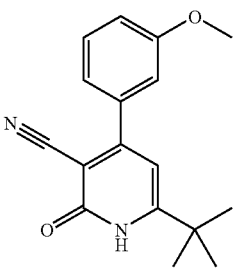

Analogously to Example 1a), 618 mg of product is obtained from 4.53 g of ammonium acetate, 782 µl of cyanoacetic acid ethyl ester, 910 µl of 3,3-dimethyl-2-butanone and 895 µl of 3-methoxybenzaldehyde.

$^1$H-NMR (CDCl$_3$): δ=1.45 (9H); 3.86 (3H); 6.31 (1H); 7.04 (1H); 7.16 (2H); 7.42 (1H); 12.40 (1H) ppm.

EXAMPLE 6b

Production of 6-tert-Butyl-3-cyano-4-(3-methoxyphenyl)-2-trifluoromethanesulfonyl pyridine

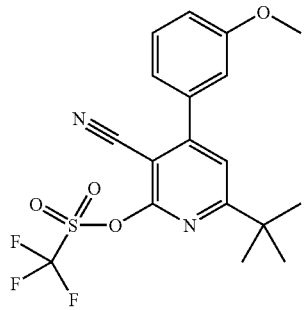

Analogously to Example 3b), 305 mg of product is obtained from 250 mg of the substance that is described under Example 6a) and 328 µl of trifluoromethanesulfonic acid anhydride in pyridine.
$^1$H-NMR (CDCl$_3$): δ=1.40 (9H); 3.89 (3H); 7.08-7.20 (3H); 7.48 (2H) ppm.

EXAMPLE 6c

Production of 6-tert-Butyl-4-(3-methoxyphenyl)-1H-pyrazolo[3,4b]pyridin-3-ylamine

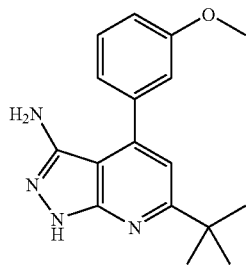

Analogously to Example 1c), 137 mg of product is produced from 299 mg of the compound that is described under Example 6b) with 88 µl of hydrazine hydrate solution (80%) in propanol.
$^1$H-NMR (CDCl$_3$): δ=1.45 (9H); 3.89 (3H); 3.97 (2H); 7.03 (2H); 7.14 (2H); 7.45 (1H); 10.40 (1H) ppm.

EXAMPLE 7

Production of 6-tert-Butyl-4-(3-cyanophenyl)-1H-pyrazolo[3,4b]-pyridin-3-ylamine

EXAMPLE 7a

Production of 6-tert-Butyl-4-(3-cyanophenyl)-2-oxo-1,2-dihydro-pyridine-3-carbonitrile

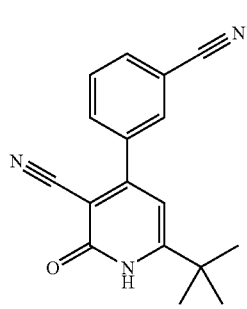

Analogously to Example 1a), 2.14 g of product is obtained from 14 g of ammonium acetate, 2.43 ml of cyanoacetic acid ethyl ester, 2.83 ml of 3,3-dimethyl-2-butanone and 3 g of 3-cyanobenzaldehyde.
$^1$H-NMR (CDCl$_3$): δ=1.46 (9H); 6.27 (1H); 7.67 (1H); 7.80-7.92 (3H); 12.42 (1H) ppm.

EXAMPLE 7b

Production of 6-tert-Butyl-3-cyano-4-(3-cyanophenyl)-2-trifluoromethane-sulfonyl pyridine

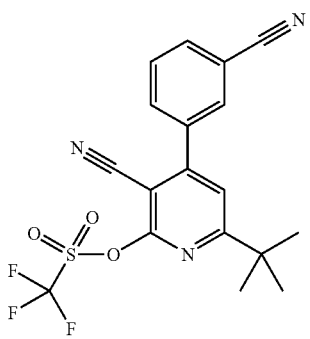

Analogously to Example 3b), 379 mg of product is obtained from 420 mg of the substance that is described under Example 7a) and 560 µL of trifluoromethanesulfonic acid anhydride in pyridine.
$^1$H-NMR (CDCl$_3$): δ=1.40 (9H); 7.45 (1H); 7.71 (1H); 7.88 (3H) ppm.

EXAMPLE 7c

Production of 6-tert-Butyl-4-(3-cyanophenyl)-1H-pyrazolo[3,4b]pyridin-3-ylamine

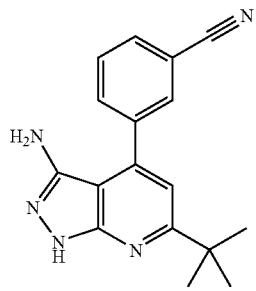

Analogously to Example 1c), 147 mg of product is produced from 369 mg of the compound that is described under Example 7b) with 165 µl of hydrazine hydrate solution (80%) in propanol.
$^1$H-NMR (d6-DMSO): δ=1.39 (9H); 4.57 (2H); 7.08 (1H); 7.72 (1H); 7.95 (2H); 8.11 (1H); 12.28 (1H) ppm.

EXAMPLE 8

Production of 1-[4-(3-Amino-6-tert-butyl-1H-pyrazolo[3,4b]pyridin-4-yl)-phenyl]-ethanone

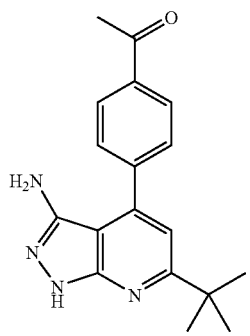

2.2 ml of a 1.6 molar solution of methyllithium in diethyl ether is added to a solution of 150 mg of the compound, described under Example 2c), in 5 ml of tetrahydrofuran at 0° C. It is allowed to stir for 2 more hours at 0° C. Then, the reaction mixture is poured into 2N hydrochloric acid. It is allowed to stir for 1 more hour at 25° C. and then neutralized with 5% sodium hydroxide solution. Then, it is extracted with ethyl acetate, and the aqueous phase is washed with saturated sodium chloride solution. It is dried on sodium sulfate. The crude product is purified by column chromatography on silica gel. 67 mg of product is obtained.

$^1$H-NMR (d6-DMSO): δ=1.38 (9H); 2.65 (3H); 4.47 (2H); 7.02 (1H); 7.74 (2H); 8.12 (2H); 12.21 (1H) ppm.

EXAMPLE 9

Production of 1-[3-(3-Amino-6-tert-butyl-1H-pyrazolo[3,4b]pyridin-4-yl)-phenyl]-ethanone

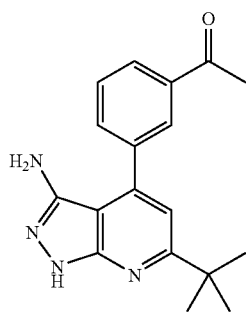

Analogously to Example 8, 82 mg of product is obtained from 169 mg of the compound that is described under Example 7c) and 1.2 ml of a 1.6 molar solution of methyllithium in diethyl ether.

$^1$H-NMR (CDCl$_3$): δ=1.46 (9H); 2.69 (3H); 3.80 (2H); 7.06 (1H); 7.65 (1H); 7.80 (1H); 8.09 (1H); 8.19 (1H); 9.57 (1H) ppm.

EXAMPLE 10

Production of 6-Cyclohexyl-4-p-tolyl-1H-pyrazolo[3,4b]pyridin-3-ylamine

EXAMPLE 10a

Production of 6-Cyclohexyl-2-oxo-4-p-tolyl-1,2-dihydropyridine-3-carbonitrile

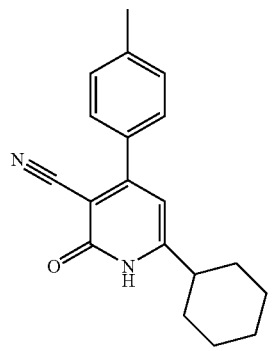

Analogously to Example 1a), 1.4 g of product is obtained from 5.13 g of ammonium acetate, 886 µl of cyanoacetic acid ethyl ester, 1.14 ml of cyclohexylmethyl ketone and 1 g of 4-methylbenzaldehyde.

$^1$H-NMR (CDCl$_3$): δ=1.30-1.70 (6H); 1.82-2.05 (4H); 2.42 (3H); 2.64 (1H); 6.25 (1H); 7.30 (2H); 7.54 (2H); 13.08 (1H) ppm.

EXAMPLE 10b

Production of 3-Cyano-6-cyclohexyl-4-p-tolyl)-2-trifluoromethane-sulfonyl pyridine

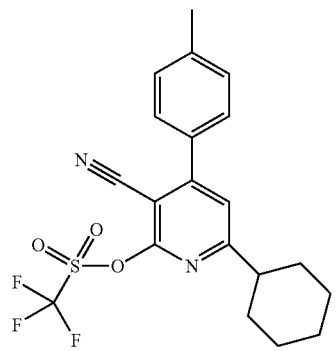

Analogously to Example 3b), 342 mg of product is obtained from 300 mg of the substance that is described under Example 10a) and 380 µl of trifluoromethanesulfonic acid anhydride in pyridine.

¹H-NMR (CDCl₃): δ=1.20-1.60 (5H); 1.75 (1H); 1.82-2.00 (4H); 2.44 (3H); 2.78 (1H); 7.30 (1H); 7.35 (2H); 7.51 (1H) ppm.

EXAMPLE 10c

Production of 6-Cyclohexyl-4-p-tolyl-1H-pyrazolo[3,4b]pyridin-3-ylamine

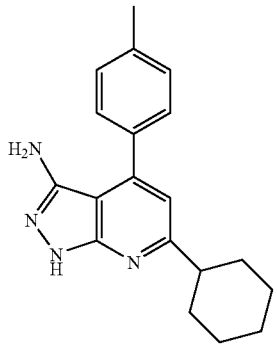

Analogously to Example 1c), 195 mg of product is produced from 342 mg of the compound that is described under Example 10b) with 147 µl of hydrazine hydrate solution (80%) in propanol.

¹H-NMR (CDCl₃): δ=1.22-1.60 (5H); 1.77 (1H); 1.88 (2H); 2.02 (2H); 2.47 (3H); 2.80 (1H); 3.92 (2H); 6.82 (1H); 7.32 (2H); 7.48 (2H); 9.80 (1H) ppm.

EXAMPLE 11

Production of 6-(1,4-Dioxa-spiro[4.5]dec-8-yl)-4-p-tolyl-1H-pyrazolo[3,4b]pyridin-3-ylamine

EXAMPLE 11a

Production of 1,4-Dioxa-spiro[4.5]decane-8-carboxylic acid ethyl ester

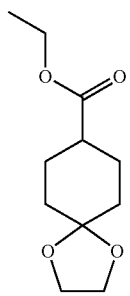

A mixture that consists of 7.35 g of 4-oxocyclohexylcarboxylic acid ethyl ester, 28 ml of trimethyl orthoformate, 64 ml of ethylene glycol and 100 mg of p-toluenesulfonic acid in 120 ml of dichloromethane is stirred for 12 hours at 25° C. Then, 2 ml of triethylamine is added. It is washed with saturated sodium bicarbonate solution and then with saturated sodium chloride solution, dried on sodium sulfate, and concentrated by evaporation in a vacuum. The crude product that is obtained is purified by column chromatography on silica gel. 9.22 g of product is obtained.

¹H-NMR (CDCl₃): δ=1.23 (3H); 1.55 (2H); 1.72-1.86 (4H); 1.94 (2H); 2.31 (1H); 3.93 (4H); 4.12 (2H) ppm.

EXAMPLE 11b

Production of (1,4-Dioxa-spiro[4.5]dec-8-yl)-methanol

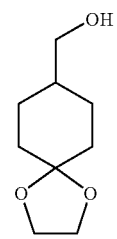

13.8 ml of a 1.2 molar solution of diisobutylamine in toluene is added to a solution of 1.18 g of the compound, described under Example 11a), in 20 ml of toluene at 0° C. It is allowed to stir for one more hour at 0° C., and then 6 ml of 2-propanol as well as 6 ml of water are added. It is allowed to stir for another hour, and then the precipitated salts are filtered off over Celite. After drying and concentration by evaporation, the crude product that is obtained is purified by column chromatography on silica gel. 880 mg of product is obtained.

¹H-NMR (CDCl₃): δ=1.15-1.40 (3H); 1.48-1.62 (3H); 1.78 (4H); 3.49 (2H); 3.95 (4H) ppm.

EXAMPLE 11c

Production of 1,4-Dioxa-spiro[4.5]decane-8-carbaldehyde

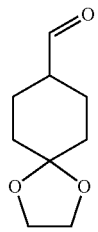

7.96 ml of dimethyl sulfoxide is added to a solution of 4.9 ml of oxalyl chloride in 30 ml of dichloromethane at −78° C. It is allowed to stir for 3 more minutes at −78° C., and then a solution of 6.96 g of the compound, described under Example 11c), in 70 ml of dichloromethane is added. It is stirred for 20 more minutes at −78° C. Then, 24 ml of triethylamine is added. The reaction mixture is allowed to heat over 20 minutes to 0° C. Then, it is poured into saturated sodium bicarbonate solution and extracted with dichloromethane. The organic phase is washed with saturated sodium chloride solution, dried on sodium sulfate, and concentrated by evaporation in a vacuum. 6.9 g of product, which is incorporated without purification into the next step, is obtained.

¹H-NMR (CDCl₃): δ=1.50-1.80 (6H); 1.95 (2H); 2.25 (1H); 3.98 (4H); 9.64 (1H) ppm.

EXAMPLE 11d

Production of 1-(1,4-Dioxa-spiro[4.5]dec-8-yl)-ethanol

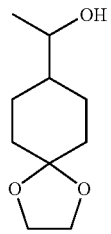

38 ml of a 1.6 molar solution of methyllithium diethyl ether is added to a solution of 6.88 g of the compound, described under Example 11c), in 100 ml of tetrahydrofuran at 0° C. It is allowed to stir for one more hour at 0° C., and then the reaction mixture is poured into the saturated ammonium chloride solution. Then, it is extracted with ethyl acetate. The organic phase is washed with saturated sodium chloride solution, dried on sodium sulfate, and concentrated by evaporation in a vacuum. After chromatography on silica gel, 6.02 g of product is obtained.

¹H-NMR (CDCl₃): δ=1.18 (3H); 1.25-1.45 (4H); 1.53 (2H); 1.70-1.92 (3H); 3.60 (1H); 3.93 (4H) ppm.

EXAMPLE 11e

Production of 1-(1,4-Dioxa-spiro[4.5]dec-8-yl)-ethanone

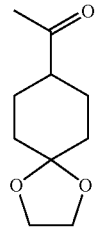

7.2 g of N-methylmorpholine-N-oxide, 565 mg of tetrapropylammonium peruthenate as well as some molecular sieve are added to a solution of 6 g of the compound, described under Example 1d), in 100 ml of dichloromethane. It is allowed to stir for 20 hours at 25° C. and then filtered over Celite. After chromatography on silica gel, 5.1 g of product is obtained.

¹H-NMR (CDCl₃): δ=1.50-1.98 (8H); 2.17 (3H); 2.34 (1H); 3.94 (4H) ppm.

EXAMPLE 11f

Production of 6-(1,4-Dioxa-spiro[4.5]dec-8-yl)-2-oxo-4-p-tolyl-1,2-dihydropyridine-3-carbonitrile

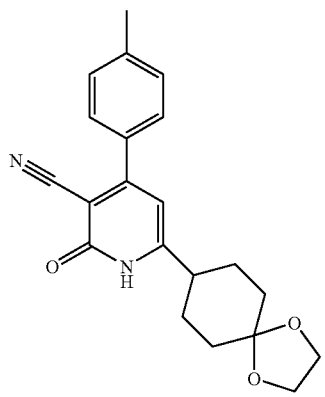

Analogously to Example 1a), 580 mg of product is obtained from 2.17 g of ammonium acetate, 375 µl of cyanoacetic acid ethyl ester, 650 mg of the compound that is described under Example 11e), and 415 µl of 4-methylbenzaldehyde.

¹H-NMR (CDCl₃): δ=1.70-1.95 (6H); 2.03 (2H); 2.42 (3H); 2.72 (1H); 3.96 (4H); 6.30 (1H); 7.30 (2H); 7.52 (2H) ppm.

EXAMPLE 11g

Production of 3-Cyano-6-(1,4-dioxa-spiro[4.5]dec-8-yl)-4-p-tolyl-2-trifluoromethanesulfonyl pyridine

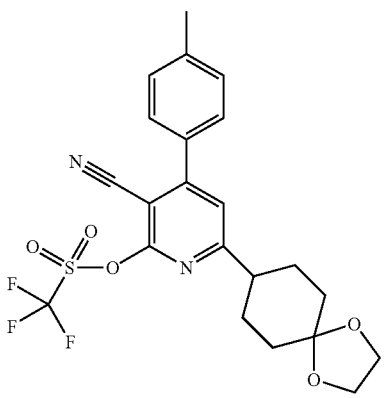

Analogously to Example 3b, 843 mg of product is obtained from 900 mg of the substance that is described under Example 1f) and 950 µl of trifluoromethanesulfonic acid anhydride in pyridine.

$^1$H-NMR (CDCl$_3$): δ=1.60-1.78 (2H); 1.80-2.08 (6H); 2.45 (3H); 2.83 (1H); 3.98 (3H); 7.35 (3H); 7.51 (2H) ppm.

EXAMPLE 11h

Production of 6-(1,4-Dioxa-spiro[4.5]dec-8-yl)-4-p-tolyl-1H-pyrazolo[3,4b]pyridin-3-ylamine

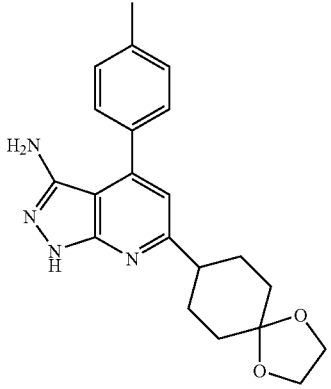

Analogously to Example 1c), 496 mg of product is produced from 838 mg of the compound that is described under Example 11g) with 317 µl of hydrazine hydrate solution (80%) in propanol.

$^1$H-NMR (CDCl$_3$): δ=1.60-2.10 (8H); 2.44 (3H); 3.36 (1H); 3.98 (6H); 6.86 (1H); 7.32 (2H); 7.46 (2H) ppm.

EXAMPLE 12

Production of 4-(3-Amino-4-p-tolyl-1H-pyrazolo[3,4b]pyridin-6-yl)-cyclohexanone

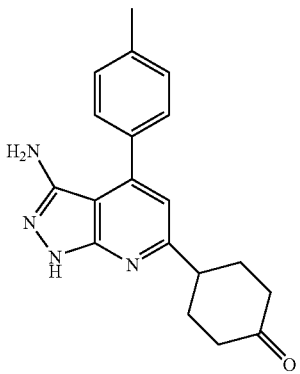

1.2 ml of 4N hydrochloric acid is added to a solution of 342 mg of the substance, described under Example 11h), in 20 ml of acetone. It is allowed to stir for 3.5 more hours at 25° C., and then 1 ml of triethylamine is added. Then, it is filtered, and the filtrate is concentrated by evaporation in a vacuum. The residue is dissolved in ethyl acetate. It is washed with saturated sodium chloride solution, dried on sodium sulfate, and concentrated by evaporation again in a vacuum. After recrystallization from a mixture that consists of dichloromethane/diisopropyl ether, 240 mg of product is obtained.

$^1$H-NMR (CDCl$_3$): δ=2.10-2.45 (4H); 2.46 (3H); 2.52-2.65 (4H); 3.32 (1H); 4.00 (2H); 6.88 (1H); 7.35 (2H); 7.49 (2H); 10.75 (1H) ppm.

EXAMPLE 13

Production of 4-[4-(3-Amino-4-p-tolyl-1H-pyrazolo[3,4b]pyridin-6-yl)-cyclohexyl]-piperazine-1-carboxylic acid tert-butyl ester

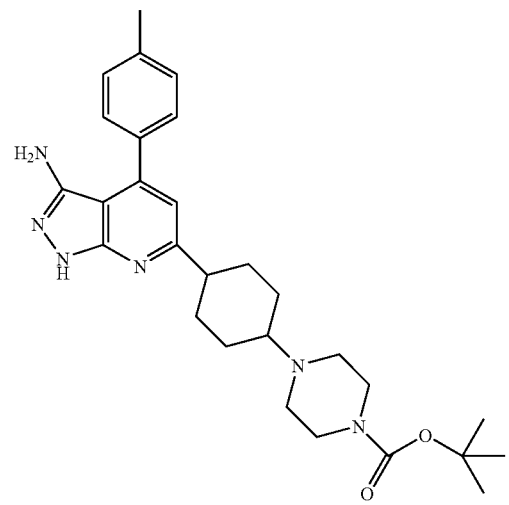

291 mg of 1-tert-butoxycarbonylpiperazine, 90 µl of glacial acetic acid as well as molecular sieve are added to a solution of 100 mg of the compound, described under Example 12, in 4 ml of dichloromethane. It is stirred for 30 minutes at 25° C., and then 40 mg of sodium acetoxy borohydride is added. It is stirred for 30 more minutes at 25° C. Then, another 40 mg of sodium acetoxy borohydride is added. It is allowed to stir for 3 more hours at 25° C. and then diluted with ethyl acetate. It is washed with saturated sodium bicarbonate and with saturated sodium chloride solution, dried on sodium sulfate, and concentrated by evaporation in a vacuum. The crude product is purified via column chromatography. 108 mg of product is obtained.

$^1$H-NMR (CDCl$_3$): δ=1.45 (9H); 1.60-2.35 (8H); 2.46 (3H); 2.81 (4H); 3.00 (1H); 3.40 (5H); 3.92 (2H); 6.88 (1H); 7.33 (2H); 7.47 (2H); 9.70 (1H) ppm.

EXAMPLE 14

Production of 6-(4-piperazin-1-yl-cyclohexyl)-4-p-tolyl-1H-pyrazolo[3,4b]pyridin-3-ylamine

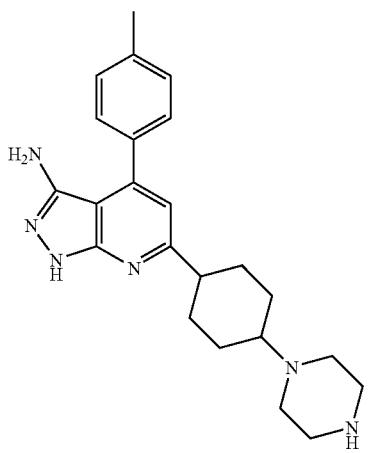

A solution of 50 mg of the compound, described under Example 13, in 1 ml of dichloromethane is mixed with 300 µl of a 2 molar HCl solution in diethyl ether. It is allowed to stir for one more hour at 25° C., and then 300 µl of a 2 molar HCl solution in diethyl ether is added again. It is stirred for another hour at 25° C. Then, it is concentrated by evaporation in a vacuum and purified by column chromatography. 29 mg of product is obtained.

$^1$H-NMR (d6-DMSO): δ=1.75-2.02 (8H); 2.41 (3H); 3.00-4.00 (12H); 7.20 (1H); 7.38 (2H); 7.60 (2H); 9.80 (2H) ppm.

EXAMPLE 15

Production of 6-[4-(4-Methyl-piperazin-1-yl)-cyclo-hexyl]-4-p-tolyl-1H-pyrazolo[3,4b]pyridin-3-ylamine

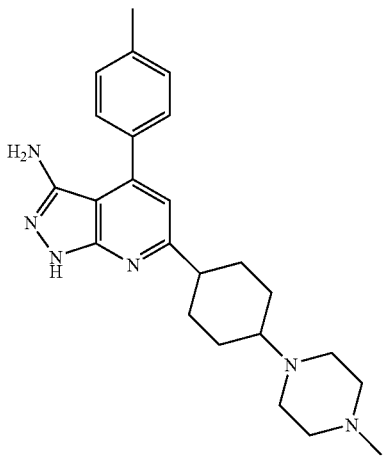

Analogously to Example 13, 41 mg of product is obtained from 48 mg of the compound that is described under Example 12, 85 µl of N-methylpiperazine, 43 µl of glacial acetic acid, and 40 mg of sodium triacetoxy borohydride.

$^1$H-NMR (d6-DMSO): δ=1.50-2.40 (8H); 2.22 (3H); 2.39 (3H); 2.91 (1H); 3.20-3.55 (9H); 4.48 (2H); 6.79 (1H); 7.37 (2H); 7.48 (2H) ppm.

EXAMPLE 16

Production of 6-(4-Piperidin-1-yl-cyclohexyl)-4-p-tolyl-1H-pyrazolo[3,4b]pyridin-3-ylamine

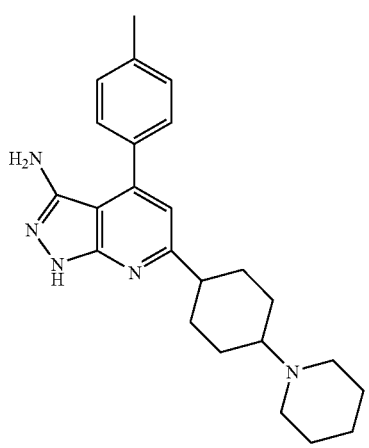

Analogously to Example 13, 52 mg of product is obtained from 70 mg of the compound that is described under Example 12, 110 µl of piperidine, 63 µl of glacial acetic acid and 50 mg of sodium triacetoxy borohydride.

$^1$H-NMR (CDCl$_3$): δ=1.40 (2H); 1.50-1.80 (7H); 1.90 (2H); 2.20-2.38 (5H); 2.40-2.60 (6H); 3.05 (1H); 3.92 (2H); 6.90 (1H); 7.32 (2H); 7.48 (2H) ppm.

EXAMPLE 17

Production of 6-(4-Morpholin-4-yl-cyclohexyl)-4-p-tolyl-1H-pyrazolo[3,4b]pyridin-3-ylamine

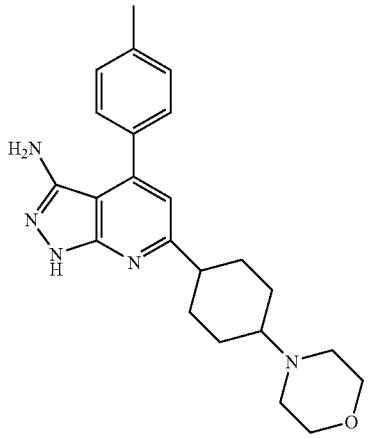

Analogously to Example 13, 48 mg of product is obtained from 70 mg of the compound that is described under Example 12, 100 µl of morpholine, 63 µl of glacial acetic acid, and 50 mg of sodium triacetoxy borohydride.

$^1$H-NMR (d6-DMSO): δ=1.50-1.70 (4H); 1.90-2.20 (6H); 2.30-2.50 (6H); 2.95 (1H); 3.58 (4H); 4.46 (2H); 6.79 (1H); 7.37 (2H); 7.49 (2H); 12.11 (1H) ppm.

EXAMPLE 18

Production of 6-(1,4-Dioxa-spiro[4.5]dec-8-yl)-4-(4-phenoxyphenyl)-1H-pyrazolo[3,4b]pyridin-3-ylamine

EXAMPLE 18a

Production of 6-(1,4-Dioxa-spiro[4.5]dec-8-yl)-2-oxo-4-(4-phenoxy-phenyl)-1,2-dihydro-pyridine-3-carbonitrile

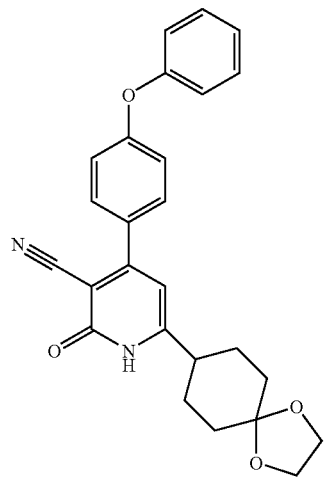

Analogously to Example 1a), 1.86 g of product is obtained from 5.28 g of ammonium acetate, 910 μl of cyanoacetic acid ethyl ester, 1.58 g of the compound that is described under Example 11e) and 1.5 ml of 4-phenoxybenzaldehyde.
$^1$H-NMR (CDCl$_3$): δ=1.70-1.95 (6H); 2.05 (2H); 2.70 (1H); 3.98 (4H); 6.30 (1H); 7.08 (4H); 7.19 (1H); 7.40 (2H); 7.60 (2H); 12.89 (1H) ppm.

EXAMPLE 18b

Production of 3-Cyano-6-(1,4-dioxa-spiro[4.5]dec-8-yl)-4-(4-phenoxy-phenyl)-2-trifluoromethanesulfonyl pyridine

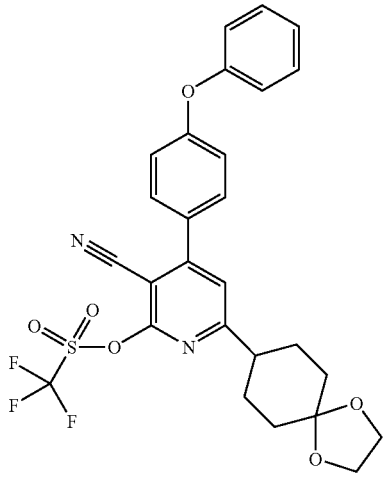

Analogously to Example 3b), 2.01 g of product is obtained from 1.86 g of the substance that is described under Example 18 and 1.61 ml of trifluoromethanesulfonic acid anhydride in pyridine.
$^1$H-NMR (CDCl$_3$): δ=1.60-2.10 (8H); 2.85 (1H); 3.98 (4H); 7.10 (4H); 7.21 (1H); 7.40 (2H); 7.58 (2H) ppm.

EXAMPLE 18c

Production of 6-(1,4-Dioxa-spiro[4.5]dec-8-yl)-4-(4-phenoxyphenyl)-1H-pyrazolo[3,4b]pyridin-3-ylamine

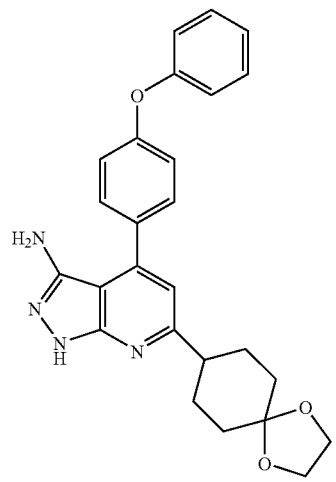

Analogously to Example 1c), 970 mg of product is produced from 1.36 mg of the compound that is described under Example 19 with 445 μl of hydrazine hydrate solution (80%) in propanol.
$^1$H-NMR (CDCl$_3$): δ=1.60-2.10 (8H); 2.88 (1H); 3.99 (4H); 6.88 (1H); 7.05-7.14 (5H); 7.40 (2H); 7.53 (2H); 10.00 (1H) ppm.

EXAMPLE 19

Production of 4-[3-Amino-4-(4-phenoxy-phenyl)-1H-pyrazolo[3,4b]-pyridin-6-yl]-cyclohexanone

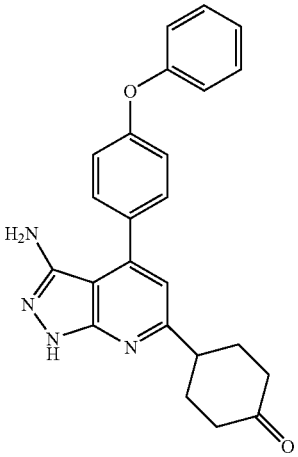

Analogously to Example 12, 890 mg of product is obtained from 1.19 g of the compound that is described under Example 18c) by reaction with 4N hydrochloric acid in acetone.
$^1$H-NMR (CDCl$_3$): δ=2.10-2.60 (8H); 3.30 (1H); 3.99 (2H); 6.88 (1H); 7.03-7.22 (5H); 7.40 (2H); 7.55 (2H); 10.08 (1H) ppm.

EXAMPLE 20

Production of 4-{4-[3-Amino-4-(4-phenoxy-phenyl)-1H-pyrazolo[3,4b]pyridin-6-yl]-cyclohexyl}-piperazine-1-carboxylic acid tert-butyl ester

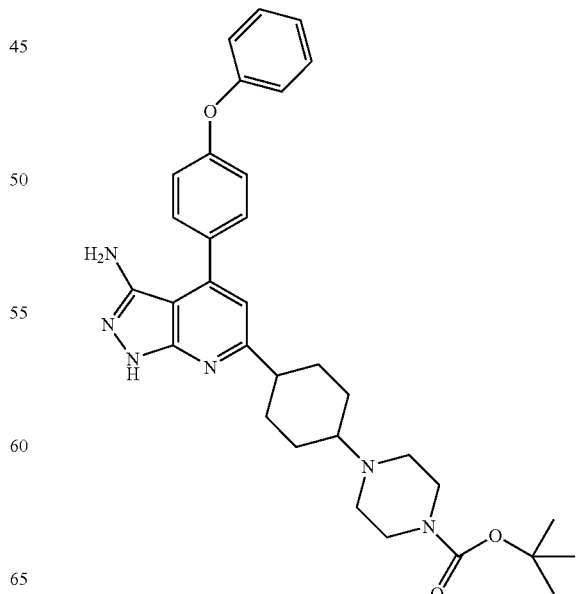

Analogously to Example 13, 142 mg of product is obtained by reaction of 170 mg of the substance that is described under Example 18c) with 400 mg of 1-tert-butoxycarbonylpiperazine, 125 μl of glacial acetic acid, and 100 mg of sodium acetoxy borohydride in dichloromethane.

$^1$H-NMR (d6-DMSO): δ=1.40 (9H); 1.50-1.70 (5H); 1.90 (2H); 2.10 (2H); 2.22 (2H); 2.40 (4H); 2.95 (1H); 4.52 (2H); 6.81 (1H); 7.10-7.25 (5H); 7.45 (2H); 7.60 (2H) ppm.

EXAMPLE 21

Production of 4-(4-Phenoxyphenyl)-6-(4-piperazin-1-yl-cyclohexyl)-1H-pyrazolo[3,4b]pyridin-3-ylamine

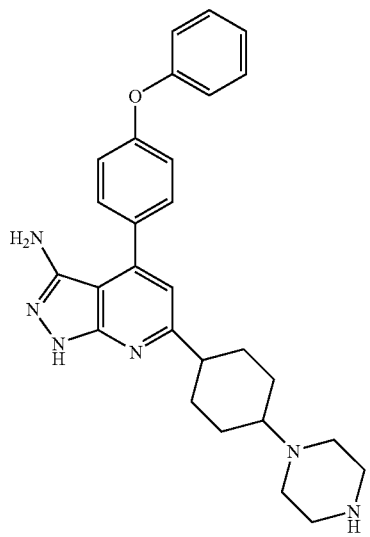

Analogously to Example 14, 9 mg of product is obtained by reaction of 20 mg of the substance that is described under Example 20 with 300 μl of HCl solution (2 molar in diethyl ether) in dichloromethane.

$^1$H-NMR (d6-DMSO): δ=1.75-2.00 (8H); 3.10-4.00 (12H); 7.05-7.20 (5H); 7.45 (2H); 7.68 (2H); 9.70 (1H); 11.20 (1H) ppm; 7.20 (1H); 7.38 (2H); 7.60 (2H); 9.80 (2H) ppm.

EXAMPLE 22

Production of 6-[4-(4-Methyl-piperazin-1-yl)-cyclohexyl]-4-(4-phenoxyphenyl)-1H-pyrazolo[3,4b]pyridin-3-ylamine

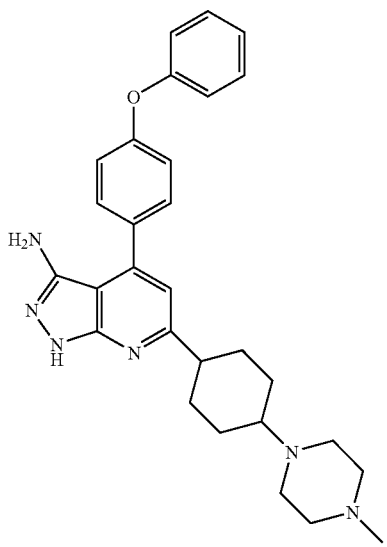

Analogously to Example 13, 32 mg of product is obtained from 37 mg of the compound that is described under Example 19), 52 μl of N-methylpiperazine, 27 μl of glacial acetic acid, and 25 mg of sodium triacetoxy borohydride.

$^1$H-NMR (CDCl$_3$): δ=1.60 (2H); 1.95 (2H); 2.20-2.35 (4H); 2.29 (3H); 2.40-2.65 (8H); 3.00 (1H); 3.92 (2H); 6.89 (1H); 7.05-7.22 (5H); 7.40 (2H); 7.55 (2H); 9.74 (1H) ppm.

EXAMPLE 23

Production of 4-(4-Phenoxy-phenyl)-6-(4-piperidin-1-yl-cyclohexyl)-1H-pyrazolo[3,4b]pyridin-3-ylamine

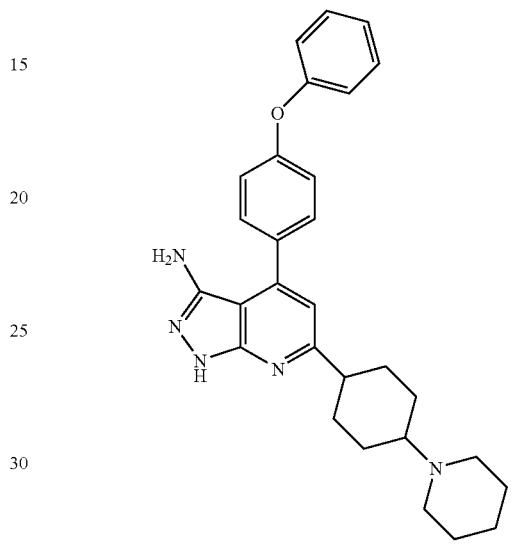

Analogously to Example 13, 58 mg of product is obtained from 100 mg of the compound that is described under Example 19), 125 μl of piperidine, 72 μl of glacial acetic acid, and 60 mg of sodium triacetoxy borohydride.

$^1$H-NMR (d6-DMSO): δ=1.10-2.00 (10H); 2.05-2.20 (4H); 2.40-2.60 (4H); 2.97 (1H); 4.52 (2H); 6.82 (1H); 7.05-7.25 (5H); 7.43 (2H); 7.60 (2H); 12.12 (1H) ppm.

EXAMPLE 24

Production of 6-(4-Morpholin-4-yl-cyclohexyl)-4-(4-phenoxyphenyl)-1H-pyrazolo[3,4b]pyridin-3-ylamine

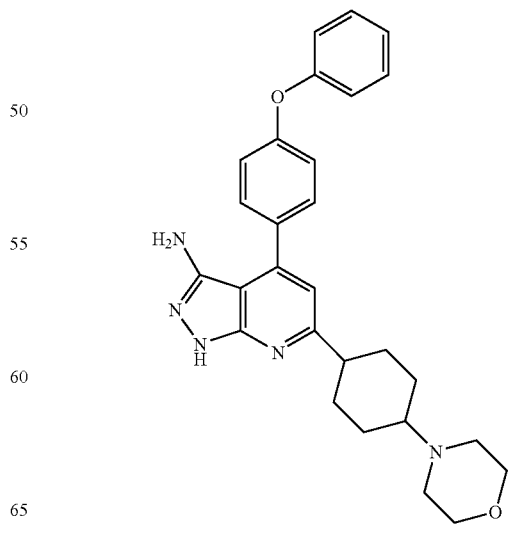

Analogously to Example 13, 52 mg of product is obtained from 90 mg of the compound that is described under Example 19, 100 µl of morpholine, 63 µl of glacial acetic acid and 50 mg of sodium triacetoxy borohydride.

$^1$H-NMR (d6-DMSO): δ=1.50-1.70 (4H); 1.80-2.20 (6H); 2.40 (4H); 2.98 (1H); 3.60 (4H); 4.52 (2H); 6.81 (1H); 7.10-7.25 (5H); 7.45 (2H); 7.60 (2H); 12.12 (1H) ppm.

EXAMPLE 25

Production of 6-(1,1-Dimethyl-2-piperidin-1-yl-ethyl)-4-p-tolyl-1H-pyrazolo[3,4b]pyridin-3-ylamine

EXAMPLE 25a

Production of 3-(tert-Butyldimethylsilyloxy)-2,2-dimethyl-propan-1-ol

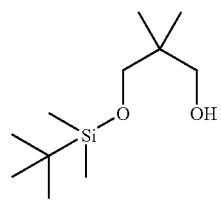

A solution of 10 g of 2,2-dimethyl-1,3-propanediol in 100 ml of tetrahydrofuran is added in drops to a suspension of 3.85 g of sodium hydride (60%) in 30 ml of tetrahydrofuran. It is allowed to stir for 45 more minutes, and then 14.5 g of tert-butyldimethylsilyl chloride is added. Then, it is stirred for one more hour at 25° C. Then, the reaction mixture is poured into saturated sodium bicarbonate solution. It is extracted with ethyl acetate, the organic phase is washed with saturated sodium chloride solution, dried on sodium sulfate, and concentrated by evaporation in a vacuum. The crude product is purified by column chromatography on silica gel. 18.4 g of product is obtained.

$^1$H-NMR (CDCl$_3$): δ=0.05 (6H); 0.90 (15H); 2.86 (1H); 3.49 (4H) ppm.

EXAMPLE 25b

Production of 3-(tert-Butyldimethylsilyloxy)-2,2-dimethyl-propan-1-al

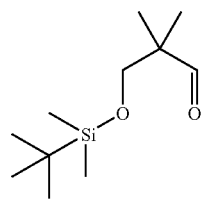

Analogously to Example 11c), 890 mg of crude product, which is incorporated without purification into the next step, is obtained from 1 g of the compound that is described under Example 25a), 910 µl of dimethyl sulfoxide, 555 µl of oxalyl chloride and 2.8 ml of triethylamine in dichloromethane.

$^1$H-NMR (CDCl$_3$): δ=0.03 (6H); 0.89 (9H); 1.02 (6H); 3.61 (2H); 9.57 (1H) ppm.

EXAMPLE 25c

Production of 4-(tert-Butyldimethylsilyloxy)-3,3-dimethyl-butan-2-ol

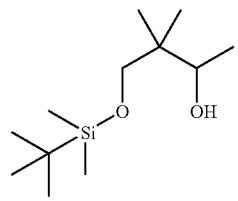

Analogously to Example 1d), 2.08 g of product is obtained from 2.6 g of the compound that is described under Example 25b) and 10.8 ml of a 1.6 molar solution of methyllithium in diethyl ether after column chromatography.

$^1$H-NMR (CDCl$_3$): δ=0.09 (6H); 0.80 (3H); 0.90 (12H); 1.10 (3H); 3.48 (2H); 3.70 (1H); 3.82 (11H) ppm.

EXAMPLE 25d

Production of 4-(tert-Butyldimethylsilyloxy)-3,3-dimethyl-butan-2-one

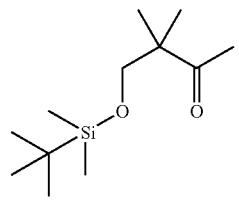

Analogously to Example 11e), 1.61 g of product is obtained from 2.1 g of the compound that is described under Example 25c), 2 g of N-methylmorpholine-N-oxide and 158 mg of tetrapropylammonium peruthenate in dichloromethane.

$^1$H-NMR (CDCl$_3$): δ=0.02 (6H); 0.87 (9H); 1.10 (6H); 2.17 (3H); 3.58 (2H) ppm.

EXAMPLE 25e

Production of 6-(2-Hydroxy-1,1-dimethylethyl)-2-oxo-4-p-tolyl-1,2-dihydro-pyridine-3-carbonitrile

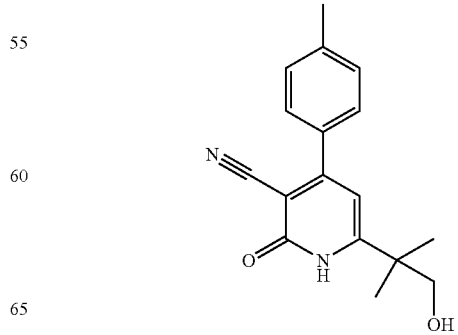

Analogously to Example 1a), 4.8 g of product is obtained from 16.6 g of ammonium acetate, 2.9 ml of cyanoacetic acid ethyl ester, 6.2 g of the compound that is described under Example 25d) and 3.2 ml of 4-methylbenzaldehyde.

$^1$H-NMR (d6-DMSO): δ 1.23 (6H); 2.39 (3H); 3.57 (2H); 6.27 (1H); 7.37 (2H); 7.53 (2H) ppm.

EXAMPLE 25f

Production of 6-(1,1-Dimethyl-2-oxo-ethyl)-2-oxo-4-p-tolyl-1,2-dihydro-pyridine-3-carbonitrile

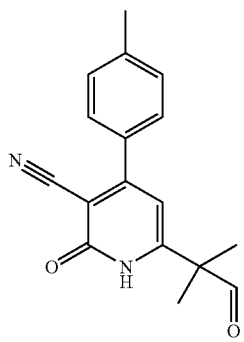

A solution of 680 mg of sulfur trioxide pyridine complex in 7 ml of dimethyl sulfoxide is added at 0° C. to a solution that consists of 400 mg of the compound that is described under Example 25e), 1.5 ml of dimethyl sulfoxide and 980 μl of triethylamine in 8 ml of dichloromethane. It is stirred for 3 more hours at 0° C. Then, water is added to the reaction mixture. It is extracted with dichloromethane, washed with saturated sodium chloride solution, dried on sodium sulfate, and concentrated by evaporation in a vacuum. After column chromatography on silica gel, 232 mg of product is obtained.

$^1$H-NMR (CDCl$_3$): δ=1.49 (6H); 2.40 (3H); 6.39 (1H); 7.28 (2H); 7.50 (2H); 9.65 (1H) ppm.

EXAMPLE 25g

Production of 6-(1,1-Dimethyl-2-piperidin-1-yl-ethyl)-2-oxo-4-p-tolyl-1,2-dihydro-pyridine-3-carbonitrile

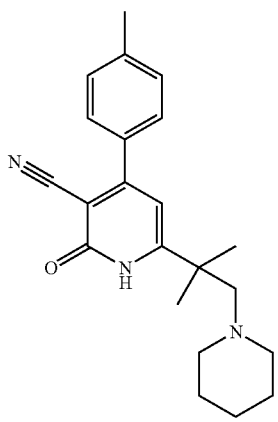

Analogously to Example 13, 118 mg of product is obtained from 184 mg of the compound that is described under Example 25f), 325 μl of piperidine and 192 mg of sodium triacetoxy borohydride.

$^1$H-NMR (CDCl$_3$): δ=1.38 (6H); 1.40-1.80 (6H); 2.41 (3H); 2.51 (2H); 2.60 (4H); 6.09 (1H); 7.30 (2H); 7.50 (2H) ppm.

EXAMPLE 25h

Production of 3-Cyano-6-(1,1-dimethyl-2-piperidin-1-yl-ethyl)-4-p-tolyl-2-trifluoromethanesulfonyl pyridine

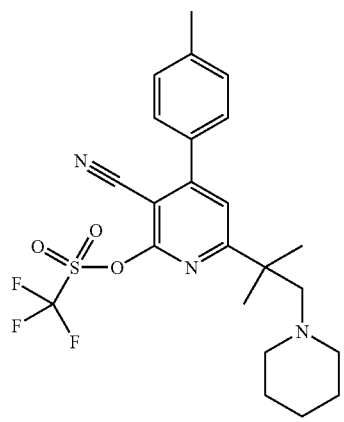

Analogously to Example 3b), 110 mg of product is obtained from 87 mg of the substance that is described under Example 25g) and 92 μl of trifluoromethanesulfonic acid anhydride in pyridine.

$^1$H-NMR (CDCl$_3$): δ=1.40 (6H); 1.60 (6H); 2.10-2.30 (4H); 2.47 (3H); 2.53 (2H); 7.37 (2H); 7.52 (3H) ppm.

EXAMPLE 25i

Production of 6-(1,1-Dimethyl-2-piperidin-1-yl-ethyl)-4-p-tolyl-1H-pyrazolo[3,4b]pyridine-3-ylamine

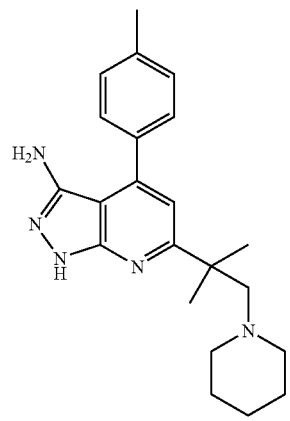

Analogously to Example 1c), 45 mg of product is produced from 106 mg of the compound that is described under Example 25h) with 41 μl of hydrazine hydrate solution (8.0%) in propanol.

$^1$H-NMR (CDCl$_3$): δ=1.40 (6H); 1.50-1.70 (6H); 2.20-2.35 (4H); 2.49 (3H); 2.60 (2H); 3.93 (2H); 7.07 (1H); 7.35 (2H); 7.48 (2H); 9.70 (1H) ppm.

EXAMPLE 26

Production of 6-(1,1-Dimethyl-2-morpholin-1-yl-ethyl)-4-p-tolyl-1H-pyrazolo[3,4b]pyridin-3-ylamine

EXAMPLE 26a

Production of 6-(1,1-Dimethyl-2-morpholin-4-yl-ethyl)-2-oxo-4-p-tolyl-1,2-dihydro-pyridine-3-carbonitrile

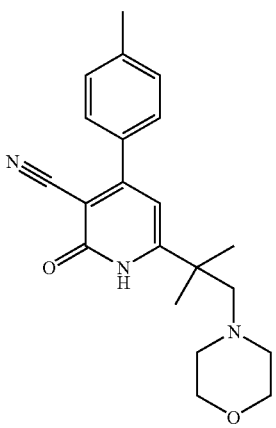

Analogously to Example 13, 139 mg of product is obtained from 181 mg of the compound that is described under Example 25f), 282 μl of morpholine and 180 mg of sodium triacetoxy borohydride.
$^1$H-NMR (CDCl$_3$): δ=1.30 (6H); 2.42 (3H); 2.70 (4H); 3.83 (4H); 6.13 (1H); 7.30 (2H); 7.51 (2H) ppm.

EXAMPLE 26b

Production of 3-Cyano-6-(1,1-dimethyl-2-morpholin-1-yl-ethyl)-4-p-tolyl-2-trifluoromethanesulfonyl pyridine

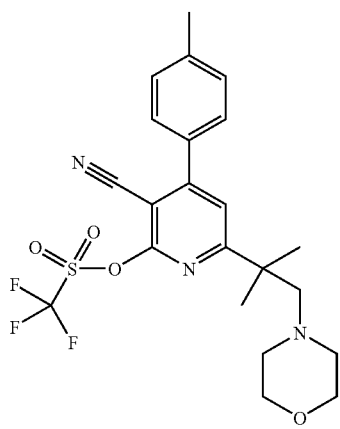

Analogously to Example 3b), 165 mg of product is obtained from 135 mg of the substance that is described under Example 26a) and 142 μl of trifluoromethanesulfonic acid anhydride in pyridine.
$^1$H-NMR (CDCl$_3$): δ=1.37 (6H); 2.30 (4H); 2.62 (3H); 3.50 (4H); 7.40-7.55 (5H) ppm.

EXAMPLE 26c

Production of 6-(1,1-Dimethyl-2-morpholin-1-yl-ethyl)-4-p-tolyl-1H-pyrazolo[3,4b]pyridin-3-ylamine

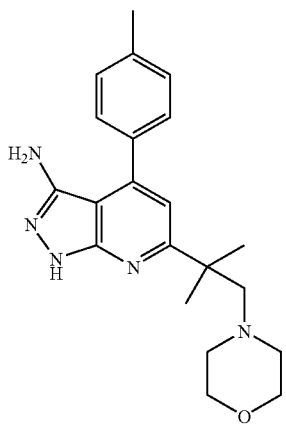

Analogously to Example 1c), 65 mg of product is produced from 165 mg of the compound that is described under Example 26b) with 70 μl of hydrazine hydrate solution (80%) in propanol.
$^1$H-NMR (d6-DMSO): δ=1.35 (6H); 2.20 (4H); 2.39 (3H); 2.62 (2H); 3.40 (4H); 4.47 (2H); 6.97 (1H); 7.38 (2H); 7.46 (2H) ppm.

EXAMPLE 27

Production of 6-[1,1-Dimethyl-2-(4-methyl-piperazin-1-yl)-ethyl]-4-p-tolyl-1H-pyrazolo[3,4b]pyridin-3-ylamine

EXAMPLE 27a

Production of 6-[1,1-Dimethyl-2-(4-methyl-piperazin-1-yl)-ethyl]-2-oxo-4-p-tolyl-1,2-dihydro-pyridine-3-carbonitrile

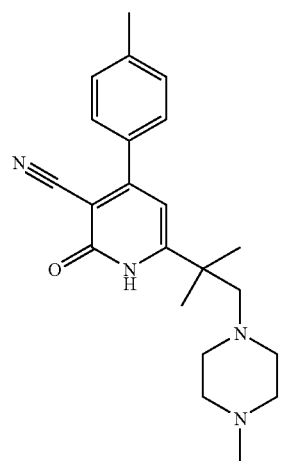

Analogously to Example 13, 68 mg of product is obtained from 106 mg of the compound that is described under Example 25f), 210 μl of N-methylpiperazine and 100 mg of sodium triacetoxy borohydride.

¹H-NMR (d6-DMSO): δ=1.24 (6H); 2.13 (3H); 2.30 (4H); 2.38 (3H); 2.45 (4H); 2.58 (2H); 6.23 (1H); 7.38 (2H); 7.55 (2H); 12.52 (1H) ppm.

EXAMPLE 27b

Production of 3-Cyano-6-[1,1-dimethyl-2-(4-methyl-piperazin-1-yl)-ethyl)]-4-p-tolyl-2-trifluoromethane-sulfonyl pyridine

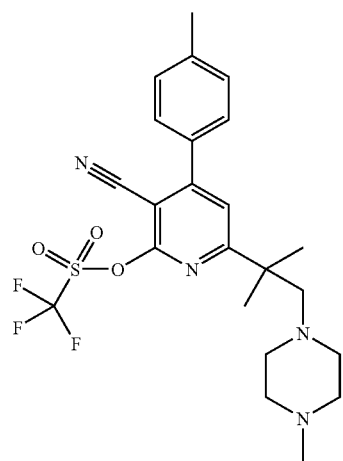

Analogously to Example 3b), 50 mg of product is obtained from 44 mg of the substance that is described under Example 27a) and 45 μl of trifluoromethanesulfonic acid anhydride in pyridine.

¹H-NMR (CDCl₃): δ=1.37 (6H); 1.98 (4H); 2.30 (3H); 2.35 (3H); 2.43 (4H); 2.68 (2H); 7.40 (2H); 7.50 (3H) ppm.

EXAMPLE 27c

Production of 6-[1,1-Dimethyl-2-(4-methyl-piper-azin-1-yl)-ethyl]-4-p-tolyl-1H-pyrazolo[3,4b]pyri-din-3-ylamine

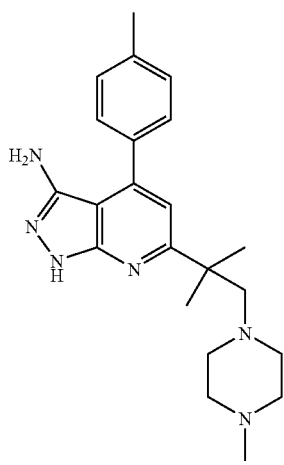

Analogously to Example 1c), 24 mg of product is produced from 50 mg of the compound that is described under Example 27b) with 22 μl of hydrazine hydrate solution (80%) in propanol.

¹H-NMR (d6-DMSO): δ=1.33 (6H); 2.10 (3H); 2.24 (4H); 2.40 (3H); 2.55 (4H); 2.62 (2H); 4.46 (2H); 6.95 (1H); 7.37 (2H); 7.48 (2H); 12.12 (1H) ppm.

EXAMPLE 28

Production of 4-[2-(3-Amino-4-p-tolyl-1H-pyrazolo [3,4b]pyridin-6-yl)-2-methyl-propyl]-piperazine-1-carboxylic acid tert-butyl ester

EXAMPLE 28a

Production of 4-[2-(5-Cyano-6-oxo-4-p-tolyl-1,6-dihydro-pyridin-2-yl)-2-methyl-propyl]-piperazine-1-carboxylic acid tert-butyl ester

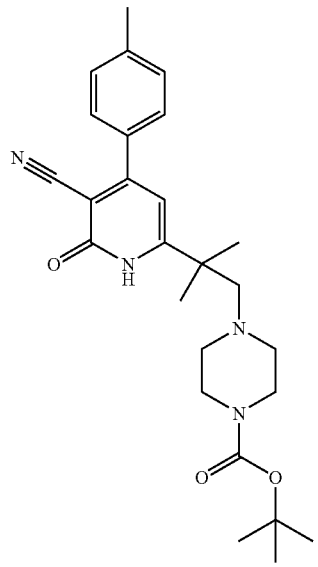

Analogously to Example 13, 245 mg of product is obtained from 182 mg of the compound that is described under Example 25f), 605 mg of 1-tert-butoxycarbonylpiperazine and 150 mg of sodium triacetoxy borohydride.

¹H-NMR (CDCl₃): δ=1.30 (6H); 1.41 (9H); 2.41 (3H); 2.60 (6H); 3.59 (4H); 6.12 (1H); 7.30 (2H); 7.50 (2H); 12.40 (1H) ppm.

EXAMPLE 28b

Production of 4-[2-(5-Cyano-4-p-tolyl-6-trifluoromethanesulfonyloxy-pyridin-2-yl)-2-methyl-propyl]-piperazine-1-carboxylic acid tert-butyl ester

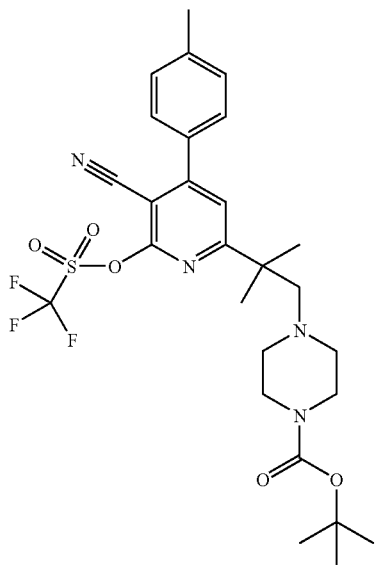

Analogously to Example 3b), 301 mg of product is obtained from 240 mg of the substance that is described under Example 28a) and 200 µl of trifluoromethanesulfonic acid anhydride in pyridine.

$^1$H-NMR (CDCl$_3$): δ=1.35 (6H); 1.41 (9H); 2.26 (4H); 2.45 (3H); 2.63 (2H); 3.23 (4H); 7.38 (2H); 7.50 (3H) ppm.

EXAMPLE 28c

Production of 4-[2-(3-Amino-4-p-tolyl-1H-pyrazolo[3,4b]pyridin-6-yl)-2-methyl-propyl]-piperazine-1-carboxylic acid tert-butyl ester

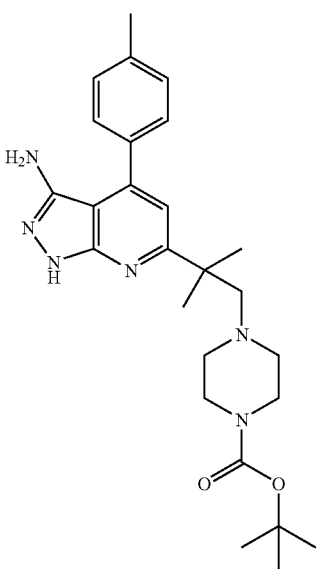

Analogously to Example 1c), 168 mg of product is produced from 300 mg of the compound that is described under Example 28b) with 97 µl of hydrazine hydrate solution (80%) in propanol.

$^1$H-NMR (CDCl$_3$): δ=1.41 (9H); 1.43 (6H); 2.25 (4H); 2.46 (3H); 2.69 (2H); 3.23 (4H); 3.93 (2H); 7.03 (1H); 7.35 (2H); 7.48 (2H); 9.98 (1H) ppm.

EXAMPLE 29

Production of 6-(1,1-Dimethyl-2-piperazin-1-yl-ethyl)-4-p-tolyl-1H-pyrazolo[3,4b]pyridin-3-ylamine

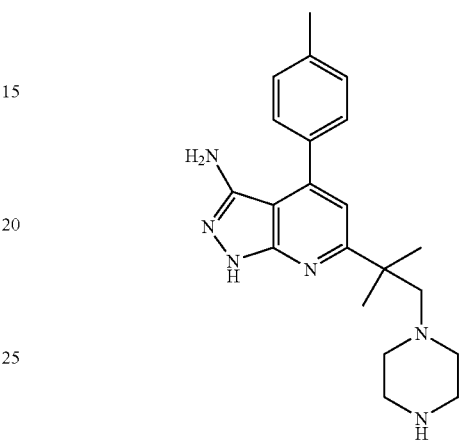

Analogously to Example 14, 43 mg of product is obtained by reaction of 80 mg of the substance that is described under Example 28c) with 430 µl of HCl solution (2 molar in diethyl ether) in dichloromethane.

$^1$H-NMR (d6-DMSO): δ=1.50 (6H); 2.41 (3H); 2.50 (6H); 3.45 (4H); 3.70 (2H); 7.20 (1H); 7.40 (2H); 7.60 (2H); 9.95 (1H) ppm.

EXAMPLE 30

Production of 6-(1,1-Dimethyl-2-(4-methyl-piperazin-1-yl)-ethyl]-4-(4-phenoxyphenyl)-1H-pyrazolo[3,4b]pyridin-3-ylamine

EXAMPLE 30a

Production of 6-(2-Hydroxy-1,1-dimethylethyl)-2-oxo-4-(4-phenoxyphenyl)-1,2-dihydro-pyridine-3-carbonitrile

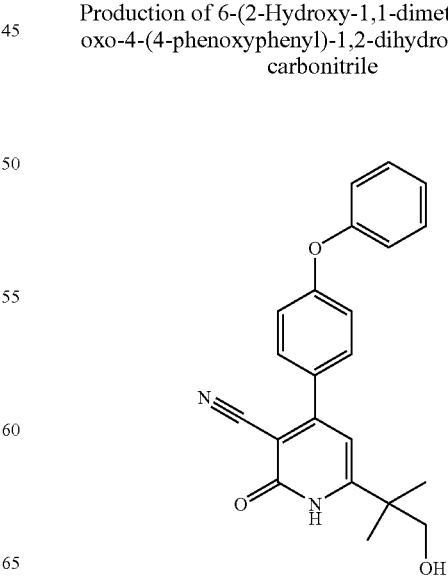

Analogously to Example 1a), 1.85 g of product is obtained from 6.7 g of ammonium acetate, 1.15 ml of cyanoacetic acid ethyl ester, 2.5 g of the compound that is described under Example 25d), and 2.15 g of 4-phenoxybenzaldehyde.

$^1$H-NMR (d6-DMSO): δ=1.24 (6H); 3.55 (2H); 6.28 (1H); 7.10 (4H); 7.23 (1H); 7.46 (2H); 7.68 (2H) ppm.

EXAMPLE 30b

Production of 6-(1,1-Dimethyl-2-oxo-ethyl)-2-oxo-4-(4-phenoxyphenyl)-1,2-dihydro-pyridine-3-carbonitrile

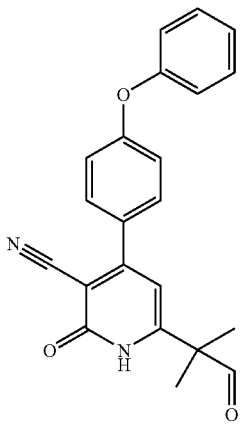

Analogously to Example 25f), 184 mg of product is obtained from 442 mg of the compound that is described under Example 30a), 585 mg of sulfur trioxide-pyridine complex and 850 µl of triethylamine in dimethyl sulfoxide.

$^1$H-NMR (CDCl$_3$): δ=1.60 (6H); 6.27 (1H); 7.10 (4H); 7.20 (1H); 7.40 (2H); 7.59 (2H); 9.70 (1H); 12.55 (1H) ppm.

EXAMPLE 30c

Production of 6-[1,1-Dimethyl-2-(4-methylpiperazin-1-yl)-ethyl]-2-oxo-4-(4-phenoxyphenyl)-1,2-dihydro-pyridine-3-carbonitrile

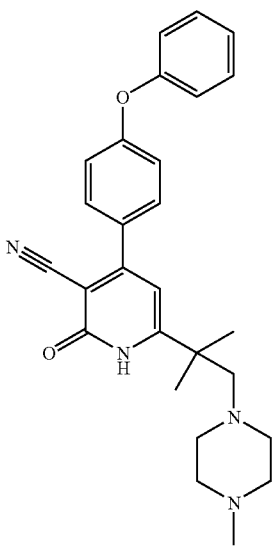

Analogously to Example 13, 101 mg of product is obtained from 130 mg of the compound that is described under Example 30b), 200 µl of N-methylpiperazine and 100 mg of sodium triacetoxy borohydride.

$^1$H-NMR (CDCl$_3$): δ=1.31 (6H); 1.63 (4H); 2.32 (3H); 2.58 (2H); 2.62 (2H); 2.72 (2H); 6.10 (1H); 7.08 (4H); 7.19 (1H); 7.40 (2H); 7.58 (2H); 12.70 (1H) ppm.

EXAMPLE 30d

Production of 3-Cyano-6-[1,1-dimethyl-2-(4-methylpiperazin-1-yl)-ethyl]-4-(4-phenoxyphenyl)-2-trifluoromethanesulfonyl pyridine

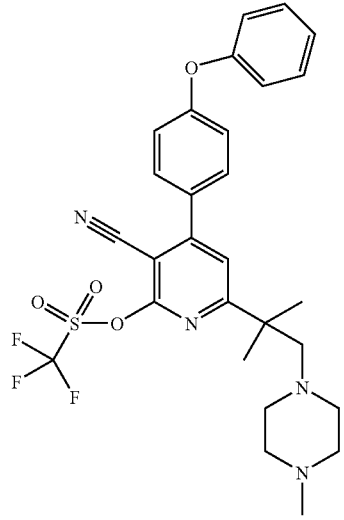

Analogously to Example 3b), 105 mg of product is obtained from 96 mg of the substance that is described under Example 30c) and 80 µl of trifluoromethanesulfonic acid anhydride in pyridine.

$^1$H-NMR (CDCl$_3$): δ=1.37 (6H); 1.76 (4H); 2.27 (3H); 2.40 (4H); 2.67 (2H); 7.05-7.28 (6H); 7.40 (2H); 7.60 (2H) ppm.

EXAMPLE 30e

Production of 6-(1,1-Dimethyl-2-(4-methyl-piperazin-1-yl)-ethyl]-4-(4-phenoxyphenyl)-1H-pyrazolo[3,4b]pyridin-3-ylamine

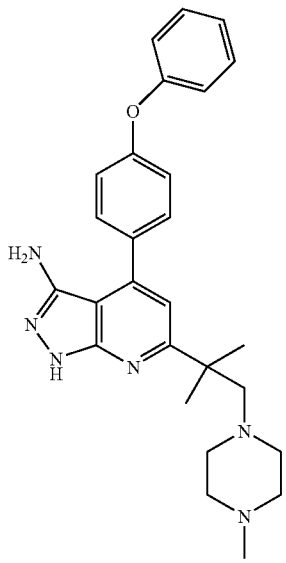

Analogously to Example 1c), 49 mg of product is produced from 134 mg of the compound that is described under Example 30d) with 40 μl of hydrazine hydrate solution (80%) in propanol.

$^1$H-NMR (d6-DMSO): δ=1.33 (6H); 2.05 (3H); 2.13 (4H); 2.27 (4H); 2.60 (2H); 4.52 (2H); 7.03-7.25 (6H); 7.43 (2H); 7.60 (2H) ppm.

EXAMPLE 31

Production of 6-(1,1-Dimethyl-2-morpholin-4-yl-ethyl)-4-(4-phenoxyphenyl)]-1H-pyrazolo[3,4b]pyridin-3-ylamine

EXAMPLE 31a

Production of 6-(1,1-Dimethyl-2-morpholin-4-yl-ethyl)-2-oxo-4-(4-phenoxyphenyl)-1,2-dihydro-pyridine-3-carbonitrile

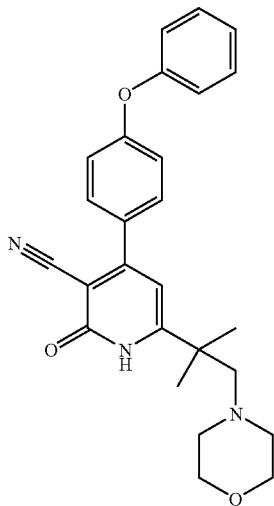

Analogously to Example 13, 122 mg of product is obtained from 145 mg of the compound that is described under Example 30b), 180 μl of morpholine and 100 mg of sodium triacetoxy borohydride.

$^1$H-NMR (d6-DMSO): δ=1.28 (6H); 2.40 (4H); 2.59 (2H); 3.53 (4H); 6.27 (1H); 7.12 (4H); 7.22 (1H); 7.48 (2H); 7.68 (2H); 12.42 (1H) ppm.

EXAMPLE 31b

Production of 3-Cyano-6-(1,1-dimethyl-2-morpholin-4-yl-ethyl)-4-(4-phenoxyphenyl)-2-trifluoromethanesulfonyl pyridine

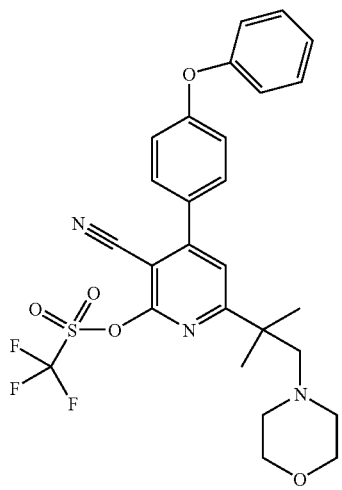

Analogously to Example 3b), 139 mg of product is obtained from 118 mg of the substance that is described under Example 31a) and 102 μl of trifluoromethanesulfonic acid anhydride in pyridine.

$^1$H-NMR (CDCl$_3$): δ=1.37 (6H); 2.30 (4H); 2.65 (2H); 3.53 (4H); 7.18-7.30 (5H); 7.41 (2H); 7.49 (1H); 7.61 (2H)

EXAMPLE 31c

Production of 6-(1,1-Dimethyl-2-morpholin-4-yl-ethyl)-4-(4-phenoxyphenyl)]-1H-pyrazolo[3,4b]pyridin-3-ylamine

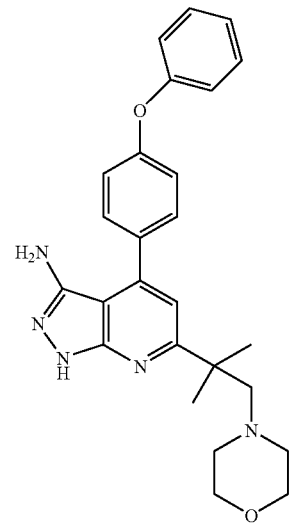

Analogously to Example 1c), 89 mg of product is produced from 135 mg of the compound that is described under Example 31b) with 50 μl of hydrazine hydrate solution (80%) in propanol.

$^1$H-NMR (CDCl$_3$): δ=1.45 (6H); 2.30 (4H); 2.70 (2H); 3.53 (4H); 3.95 (2H); 7.05 (1H); 7.08-7.23 (5H); 7.40 (2H); 7.55 (2H) ppm.

EXAMPLE 32

Production of 3-(3-Amino-6-pyridin-4-yl-1H-pyrazolo[3,4-b]pyridin-4-yl)-phenol

EXAMPLE 32a

Production of 4-(3-Hydroxyphenyl)-6-oxo-1,6-dihydro-[2,4']bipyridinyl-5-carbonitrile

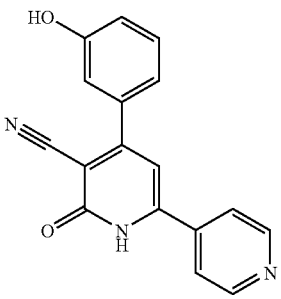

Analogously to Example 1a, 1.82 g of product is obtained from 7.57 g of ammonium acetate, 1.31 ml of cyanoacetic acid ethyl ester, 1.36 ml of 4-acetylpyridine and 1.5 g of 3-hydroxybenzaldehyde.

$^1$H-NMR (d6-DMSO): δ=6.96 (1H); 7.00-7.20 (3H); 7.48 (1H); 7.90 (2H); 8.72 (2H); 9.88 (1H); 12.97 (1H) ppm.

EXAMPLE 32b

Production of Acetic Acid 3-(5-cyano-6-oxo-1,6-dihydro-[2,4']bipyridinyl-4-yl)-phenyl Ester

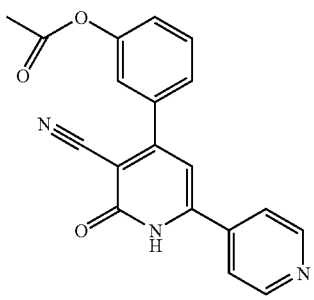

580 mg of the compound that is described under Example 32a is dissolved in 6 ml of pyridine. 0.5 ml of acetic acid anhydride is added, and it is allowed to stir for 2 more hours at 80° C. After cooling, 20 ml of water is added. It is stirred for one more hour, and then the precipitate is suctioned off. 564 mg of product is obtained.

$^1$H-NMR (d6-DMSO): δ=2.31 (3H); 7.11 (1H); 7.37 (1H); 7.55 (1H); 7.64 (2H); 7.92 (2H); 8.76 (2H); 13.02 (1H) ppm.

EXAMPLE 32c

Production of Acetic Acid 3-(5-Cyano-6-trifluoromethanesulfonyloxy-[2,4']bipyridinyl-4-yl)-phenyl Ester

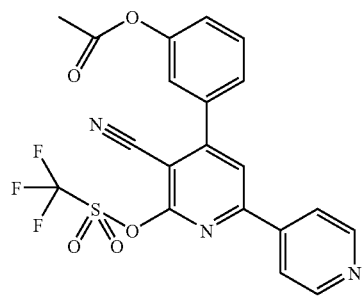

Analogously to Example 3b, 202 mg of product is obtained from 200 mg of the substance that is described under Example 32b and 305 μl of trifluoromethanesulfonic acid in pyridine.

$^1$H-NMR (CDCl$_3$): δ=2.38 (3H); 7.36 (1H); 7.41 (1H); 7.55-7.68 (2H); 7.91 (1H); 8.00 (1H); 8.86 (1H) ppm.

EXAMPLE 32d

Production of 3-(3-Amino-6-pyridin-4-yl-1H-pyrazolo[3,4-b]pyridin-4-yl)-phenol

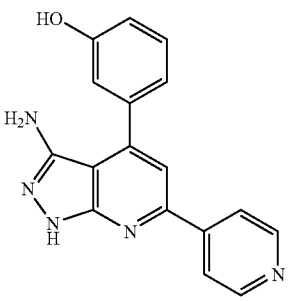

Analogously to Example 1c, 65 mg of product is obtained from 197 mg of the substance that is described under Example 32c with 80 μl of hydrazine hydrate solution (80%) in propanol.

$^1$H-NMR (d6-DMSO): δ=6.93 (1H); 7.05 (2H); 7.36 (1H); 7.42 (1H); 8.20 (1H); 8.48 (1H); 8.71 (2H); 9.82 (1H) ppm.

EXAMPLE 33

Production of 3-(3-Amino-6-pyridin-4-yl-1H-pyrazolo[3,4-b]pyridin-4-yl)-5-methoxyphenol EXAMPLE 33a Production of 2-(3,5-Dimethoxyphenyl)-[1,3]dioxolane

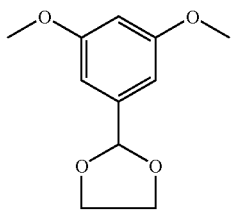

4.2 ml of ethylene glycol, 4.1 ml of trimethyl orthoformate and 5 mg of p-toluenesulfonic acid are added to a solution of 5 g of 3,5 dimethoxy benzaldehyde in 100 ml of dichloromethane. It is allowed to stir for 20 more hours at 25° C. Then, it is washed with saturated sodium bicarbonate solution and saturated sodium chloride solution, dried on sodium sulfate, and concentrated by evaporation in a vacuum. The crude product is purified by column chromatography. 5.67 g of product is obtained.

$^1$H-NMR (CDCl$_3$): δ=3.80 (6H); 4.00-4.15 (4H); 5.77 (1H); 6.45 (1H); 6.64 (2H) ppm.

EXAMPLE 33b

Production of
3-[1,3]Dioxolan-2-yl-5-methoxyphenol

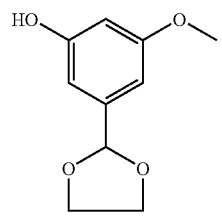

5.67 g of the substance that is described under Example 33a is dissolved in 100 ml of dimethylformamide. 7.6 g of sodium methanethiolate is added, and it is refluxed for 4 hours. Then, the reaction mixture is poured into ice water. It is allowed to stir for one more hour and then extracted with ethyl acetate. The organic phase is washed with saturated sodium chloride solution, dried on sodium sulfate, and concentrated by evaporation in a vacuum. The crude product is purified by column chromatography. 2.84 g of product is obtained.

$^1$H-NMR (CDCl$_3$): δ=3.80 (3H); 4.00-4.15 (4H); 5.18 (1H); 5.73 (1H); 6.40 (1H); 6.55 (1H); 6.61 (1H) ppm.

EXAMPLE 33c

Production of 3-Hydroxy-5-methoxy-benzaldehyde

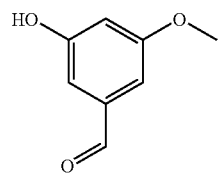

300 ml of 2N hydrochloric acid is added to a solution of 450 mg of the substance, described under Example 33b, in 10 ml of acetone. It is allowed to stir for 30 minutes at 25° C., then diluted with dichloromethane. The organic phase is dried with saturated sodium chloride solution, dried on sodium sulfate, and concentrated by evaporation in a vacuum. The crude product is purified by column chromatography. 207 mg of product is obtained.

$^1$H-NMR (d6-DMSO): δ=3.79 (3H); 6.65 (1H); 6.90 (2H); 9.85 (1H); 10.00 (1H) ppm.

EXAMPLE 33d

Production of 4-(3-Hydroxy-5-methoxyphenyl)-6-oxo-1,6-dihydro-[2,4']bipyridinyl-5-carbonitrile

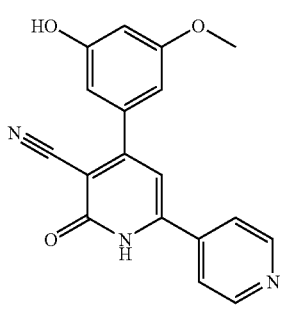

Analogously to Example 1a, 477 mg of product is obtained from 450 mg of the compound that is described under Example 33c, 1.84 g of ammonium acetate, 320 μl of cyanoacetic acid ethyl ester and 330 μl of 4-acetylpyridine.

$^1$H-NMR (d6-DMSO): δ=3.77 (3H); 6.51 (1H); 6.70 (2H); 7.05 (1H); 7.90 (2H); 8.72 (2H); 9.11 (1H) ppm.

EXAMPLE 33e

Production of Acetic Acid 3-(5-cyano-6-oxo-1,6-dihydro-[2,4']bipyridinyl-4-yl)-5-methoxyphenyl ester

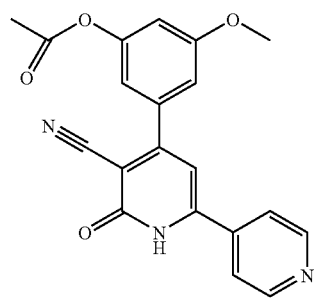

Analogously to Example 32b, 204 mg of product is obtained from 200 mg of the compound that is described under Example 33d and 160 μl of acetic acid anhydride in pyridine.

$^1$H-NMR (d6-DMSO): δ=2.29 (3H); 3.34 (3H); 6.99 (1H); 7.11 (2H); 7.22 (1H); 7.93 (2H); 8.75 (2H) ppm.

EXAMPLE 33f

Production of Acetic Acid 3-(5-cyano-6-trifluoromethane-sulfonyloxy-[2,4']bipyridinyl-4-yl)-5-methoxyphenyl ester

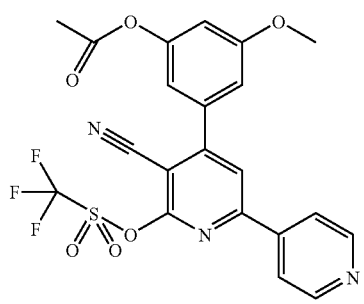

Analogously to Example 3b, 186 mg of product is obtained from 200 mg of the substance that is described under Example 33e and 280 μl of trifluoromethanesulfonic acid in pyridine.

$^1$H-NMR (CDCl$_3$): δ=2.33 (3H); 3.90 (3H); 6.89 (1H); 7.00 (1H); 7.06 (1H); 7.91 (2H); 7.99 (1H); 8.85 (2H) ppm.

EXAMPLE 33g

Production of 3-(3-Amino-6-pyridin-4-yl-1H-pyrazolo[3,4-b]pyridin-4-yl)-5-methoxyphenol

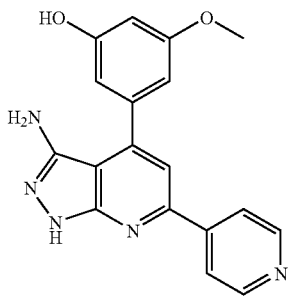

Analogously to Example 1c, 67 mg of product is obtained from 181 mg of the substance that is described under Example 33f with 70 μl of hydrazine hydrate solution (80%) in propanol.

$^1$H-NMR (d6-DMSO): δ=3.78 (3H); 6.50 (1H); 6.62 (2H); 7.43 (1H); 8.20 (2H); 8.45 (1H); 8.70 (2H); 9.85 (1H) ppm.

EXAMPLE 34

Production of 4-(3,5-Dimethoxy-phenyl)-6-pyridin-4-yl-1H-pyrazolo[3,4-b]pyridin-3-ylamine

EXAMPLE 34a

Production of 4-(3,5-Dimethoxyphenyl)-6-oxo-1,6-dihydro-[2,4']bipyridinyl-5-carbonitrile

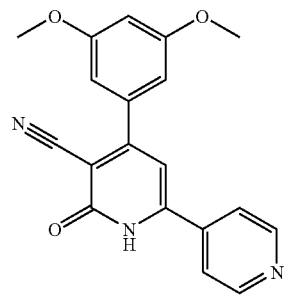

Analogously to Example 1a, 1.49 g of product is obtained from 5.57 g of ammonium acetate, 960 μl of cyanoacetic acid ethyl ester, 1 ml of 4-acetylpyridine, and 1.5 g of 3,5-dimethoxybenzaldehyde.

$^1$H-NMR (d6-DMSO): δ=3.80 (6H); 6.60 (1H); 6.76 (2H); 6.87 (1H); 7.95 (2H); 8.65 (2H) ppm.

EXAMPLE 34b

Production of Trifluoromethanesulfonic Acid-5-cyano-4-(3,5-dimethoxy-phenyl)-[2,4']bipyridinyl-6-yl Ester

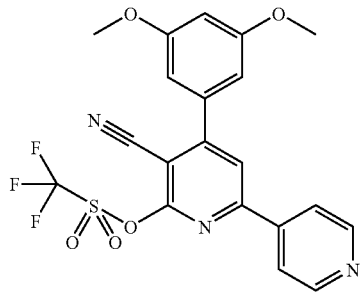

Analogously to Example 3b, 302 mg of product is obtained from 240 mg of the substance that is described under Example 34a and 360 μl of trifluoromethanesulfonic acid in pyridine.

$^1$H-NMR (d6-DMSO): δ=3.85 (6H); 6.79 (1H); 7.04 (2H); 8.17 (2H); 8.61 (1H); 8.85 (1H) ppm.

EXAMPLE 34c

Production of 4-(3,5-Dimethoxy-phenyl)-6-pyridin-4-yl-1H-pyrazolo[3,4-b]pyridin-3-ylamine

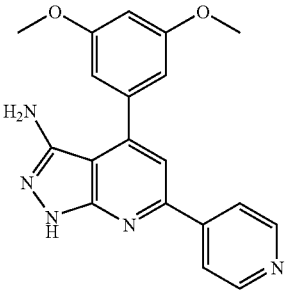

Analogously to Example 1c, 76 mg of product is obtained from 297 mg of the substance that is described under Example 34b with 120 μl of hydrazine hydrate solution (80%) in propanol.

$^1$H-NMR (d6-DMSO): δ=3.85 (6H); 4.73 (2H); 6.68 (1H); 6.84 (2H); 7.65 (1H); 8.15 (2H); 8.71 (2H); 12.51 (1H) ppm.

EXAMPLE 35

Production of 3-(3-Amino-6-pyridin-4-yl-1H-pyrazolo[3,4-b]pyridin-4-yl)-4-methyl-phenol

EXAMPLE 35a

Production of 2-Methyl-5-nitro-benzoic Acid Methyl Ester

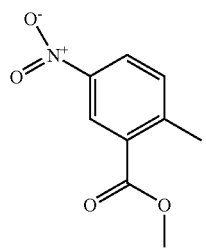

300 μl of concentrated sulfuric acid is added to a suspension of 2 g of 2-methyl-5-nitrobenzoic acid in 7 ml of methanol. It is refluxed for 6 hours. Then, the reaction mixture is diluted with ethyl acetate and poured into saturated sodium bicarbonate solution. The phases are separated, and the aqueous phase is extracted with ethyl acetate. The combined organic phases are then washed with saturated sodium chloride solution, dried on sodium sulfate, and concentrated by evaporation in a vacuum. The crude product that is obtained is incorporated without purification into the next step.

$^1$H-NMR (CDCl$_3$): δ=2.70 (3H); 3.95 (3H); 7.42 (1H); 8.23 (1H); 8.78 (1H) ppm.

EXAMPLE 35b

Production of 5-Amino-2-methylbenzoic Acid-Methyl Ester

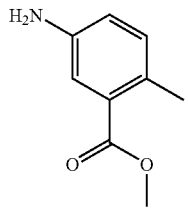

3.17 g of the compound that is described under Example 35a is hydrogenated in a mixture that consists of 20 ml of tetrahydrofuran and 5 ml of ethanol with 625 mg of palladium/carbon (10%) under hydrogen. After the reaction is completed, it is filtered over Celite and concentrated by evaporation in a vacuum. The crude product that is obtained is purified by column chromatography on silica gel with a mixture that consists of ethyl acetate/hexane. 2.65 g of product is obtained.

$^1$H-NMR (CDCl$_3$): δ=2.47 (3H); 3.87 (3H); 6.75 (1H); 7.01 (1H); 7.25 (1H) ppm.

EXAMPLE 35c

Production of 5-Hydroxy-2-methyl-benzoic Acid Methyl Ester

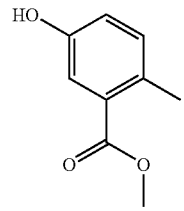

3.17 g of the compound that is described under Example 35b is suspended in 18 ml of 50% sulfuric acid. It is cooled to −5° C., and 6.4 ml of a 2.5 molar aqueous sodium nitrite solution is added at such a speed that the internal temperature does not increase above 5° C. Then, it is stirred for 1 more hour at 25° C. and for another 30 minutes at 80° C. Then, saturated sodium bicarbonate solution is slowly added to the reaction solution. It is extracted with ethyl acetate, the organic phase is washed with saturated sodium chloride solution, dried on sodium sulfate, and concentrated by evaporation in a vacuum. The crude product that is obtained is purified by column chromatography on silica gel with a mixture that consists of ethyl acetate/hexane. 1.6 g of product is obtained.

$^1$H-NMR (CDCl$_3$): δ=2.50 (3H); 3.88 (3H); 5.08 (1H); 6.90 (1H); 7.10 (1H); 7.40 (1H) ppm.

EXAMPLE 35d

Production of 5-(tert-Butyldimethylsilanyloxy)-2-methylbenzoic Acid Methyl Ester

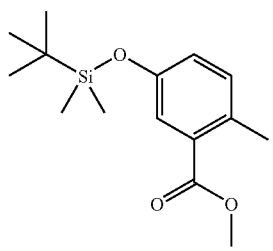

1 g of tert-butyldimethysilyl chloride is added to a solution of 770 mg of the compound that is described under Example 35c and 760 mg of imidazole in 20 ml of N,N-dimethylformamide. It is allowed to stir for 2 more hours at 25° C., and then the reaction mixture is poured into saturated sodium bicarbonate solution. It is extracted with ethyl acetate, the organic phase is washed with saturated sodium chloride solution, dried on sodium sulfate, and concentrated by evaporation in a vacuum. The crude product that is obtained is purified by column chromatography on silica gel with a mixture that consists of ethyl acetate/hexane. 1.12 g of product is obtained.

$^1$H-NMR (CDCl$_3$): δ=0.18 (6H); 0.98 (9H); 2.50 (3H); 3.89 (3H); 6.88 (1H); 7.08 (1H); 7.37 (1H) ppm.

EXAMPLE 35e

Production of [5-(tert-Butyldimethylsilanyloxy)-2-methyl-phenyl]-methanol

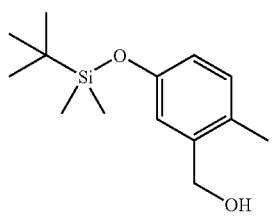

2.3 ml of a 1.2 molar solution of diisobutylaluminum hydride in toluene is added to a solution of 250 mg of the compound, described under Example 35d, in 7 ml of toluene at −30° C. It is allowed to stir for 1 more hour at 0° C., and then 1 ml of 2-propanol is added. It is allowed to stir for another 10 minutes, and 1.3 ml of water is added. It is allowed to stir for another hour and then filtered over Celite. Then, it is concentrated by evaporation in a vacuum. The crude product that is obtained (223 mg) is incorporated without purification into the next step.

$^1$H-NMR (CDCl$_3$): δ=0.18 (6H); 0.98 (9H); 2.26 (3H); 4.64 (2H); 6.68 (1H); 6.88 (1H); 7.01 (1H) ppm.

EXAMPLE 35f

Production of 5-(tert-Butyldimethylsilanyloxy)-2-methyl-benzaldehyde

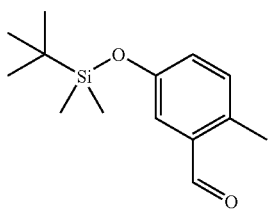

Analogously to the oxidation that is described under Example 25f), 2.03 g of product is obtained from 2.2 g of the compound that is described under Example 35e).
$^1$H-NMR (CDCl$_3$): δ=0.19 (6H); 0.99 (9H); 2.58 (3H); 6.97 (1H); 7.11 (1H); 7.26 (1H); 10.21 (1H) ppm.

EXAMPLE 35g

Production of 4-[5-(tert-Butyldimethylsilanyloxy)-2-methylphenyl]-6-oxo-1,6-dihydro-[2,4']bipyridinyl-5-carbonitrile

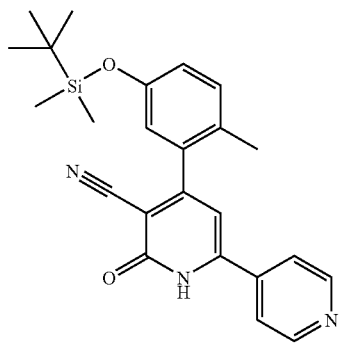

Analogously to Example 1a, 170 mg of product is obtained from 600 mg of ammonium acetate, 105 μl of cyanoacetic acid ethyl ester, 110 μl of 4-acetylpyridine and 240 mg of the substance that is described under Example 35f.
$^1$H-NMR (CDCl$_3$): δ=0.19 (6H); 0.97 (9H); 2.25 (3H); 6.72 (2H); 6.89 (1H); 7.20 (1H); 7.79 (2H); 8.86 (2H) ppm.

EXAMPLE 35h

Production of Trifluoromethanesulfonic Acid-4-[5-(tert-butyldimethyl-silanyloxy)-2-methyl-phenyl]-5-cyano-[2,4']bipyridinyl-6-yl ester

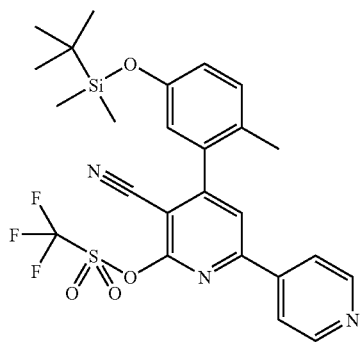

Analogously to Example 3b, 85 mg of product is obtained from 107 mg of the substance that is described under Example 35g and 130 μl of trifluoromethanesulfonic acid in pyridine.
$^1$H-NMR (CDCl$_3$): δ=0.21 (6H); 0.98 (9H); 2.19 (3H); 6.73 (1H); 6.92 (1H); 7.23 (1H); 7.86 (1H); 7.91 (2H); 8.82 (2H) ppm.

EXAMPLE 35i

Production of 4-[5-(tert-Butyldimethylsilanyloxy)-2-methyl-phenyl]-6-pyridin-4-yl-1H-pyrazolo[3,4-b]pyridin-3-ylamine

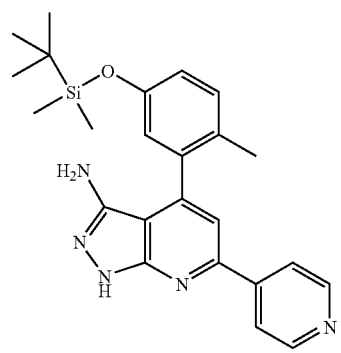

Analogously to Example 1c, 27 mg of product is obtained from 50 mg of the substance that is described under Example 35h with 20 μl of hydrazine hydrate solution (80%) in propanol.
$^1$H-NMR (d6-DMSO): δ=0.21 (6H); 0.93 (9H); 2.07 (3H); 4.38 (2H); 6.79 (1H); 6.93 (1H); 7.30 (1H); 7.52 (1H); 8.13 (2H); 8.70 (2H); 12.45 (1H) ppm.

EXAMPLE 35j

Production of 3-(3-Amino-6-pyridin-4-yl-1H-pyrazolo[3,4-b]pyridin-4-yl)-4-methyl-phenol

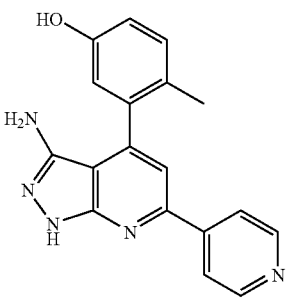

70 μl of a 1 molar solution of tetrabutylammonium fluoride in tetrahydrofuran is added to a solution of 24 mg of the substance, described under Example 35i, in 5 ml of tetrahydrofuran at 0° C. It is allowed to stir for one more hour and then poured into saturated sodium bicarbonate solution. It is extracted with ethyl acetate, the organic phase is washed with saturated sodium chloride solution, dried on sodium sulfate, and concentrated by evaporation in a vacuum. The crude product that is obtained is purified by column chromatography on silica gel with a mixture that consists of ethyl acetate/hexane. 9.8 mg of product is obtained.

$^1$H-NMR (d6-DMSO): δ=1.85 (3H); 4.22 (2H); 6.52 (1H); 6.67 (1H); 7.02 (1H); 7.35 (1H); 7.95 (2H); 8.50 (2H); 9.36 (1H); 12.27 (1H) ppm.

EXAMPLE 36

Production of 3-(3-Amino-6-tert-butyl-1H-pyrazolo[3,4-b]pyridin-4-yl)-5-methoxy-phenol

EXAMPLE 36a

Production of 6-tert-Butyl-4-(3-hydroxy-5-methoxy-phenyl)-2-oxo-1,2-dihydro-pyridine-3-carbonitrile

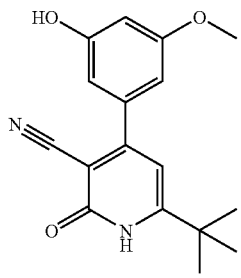

Analogously to Example 1a, 164 mg of product is obtained from 820 mg of ammonium acetate, 140 μl of cyanoacetic acid ethyl ester, 165 μl of 3,3-dimethyl-2-butanone and 202 mg of the compound that is described under Example 33c.

$^1$H-NMR (d6-DMSO): δ=1.29 (9H); 3.77 (3H); 6.19 (3H); 6.49 (1H); 6.60 (2H); 9.86 (1H); 12.25 (1H) ppm.

EXAMPLE 36b

Production of Acetic Acid-3-(6-tert-butyl-3-cyano-2-oxo-1,2-dihydro-pyridin-4-yl)-5-methoxy Phenyl Ester

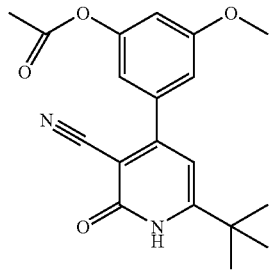

Analogously to Example 32b, 122 mg of product is obtained from 150 mg of the compound that is described under Example 36a and 130 μl of acetic acid anhydride in pyridine.

$^1$H-NMR (CDCl$_3$): δ=1.42 (9H); 2.31 (3H); 3.88 (3H); 6.29 (1H); 6.80 (1H); 6.91 (1H); 7.02 (1H); 12.12 (1H) ppm.

EXAMPLE 36c

Production of Acetic Acid 3-(6-tert-Butyl-3-cyano-2-trifluoromethanesulfonyloxy-pyridin-4-yl)-5-methoxy-phenyl Ester

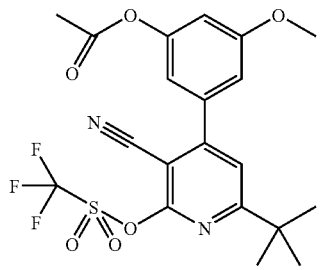

Analogously to Example 3b, 133 mg of product is obtained from 120 mg of the substance that is described under Example 36b and 175 μl of trifluoromethanesulfonic acid in pyridine.

$^1$H-NMR (CDCl$_3$): δ=1.39 (9H); 2.35 (3H); 3.88 (3H); 6.84 (1H); 6.90 (1H); 7.01 (1H); 7.46 (1H) ppm.

EXAMPLE 36d

Production of 3-(3-Amino-6-tert-butyl-1H-pyrazolo[3,4-b]pyridin-4-yl)-5-methoxy-phenol

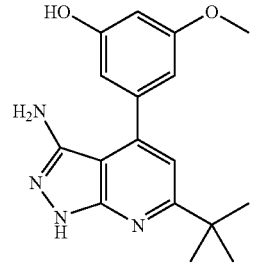

Analogously to Example 1c, 49 mg of product is obtained from 130 mg of the substance that is described under Example 36c with 55 μl of hydrazine hydrate solution (80%) in propanol.

$^1$H-NMR (d6-DMSO): δ=1.38 (9H); 3.77 (3H); 4.57 (2H); 6.46 (1H); 6.53 (2H); 6.95 (1H); 9.79 (1H); 12.12 (1H) ppm.

EXAMPLE 37

Production of 3-(3-Amino-6-tert-butyl-1H-pyrazolo[3,4-b]pyridin-4-yl)-phenol

EXAMPLE 37a

Production of 6-tert-Butyl-4-(3-hydroxyphenyl)-2-oxo-1,2-dihydro-pyridine-3-carbonitrile

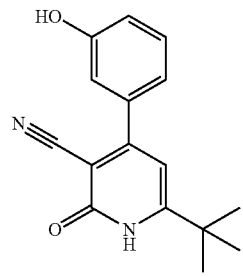

Analogously to Example 1a, 814 mg of product is obtained from 5 g of ammonium acetate, 875 µl of cyanoacetic acid ethyl ester, 1.01 ml of 3,3-dimethyl-2-butanone and 1 g of 3-hydroxybenzaldehyde.

$^1$H-NMR (d6-DMSO): δ=1.28 (9H); 6.20 (1H); 6.93 (1H); 6.98-7.08 (2H); 7.34 (1H); 9.84 (1H); 12.25 (1H) ppm.

EXAMPLE 37b

Production of Acetic Acid 3-(6-tert-Butyl-3-cyano-2-oxo-1,2-dihydro-pyridin-4-yl)-phenyl Ester

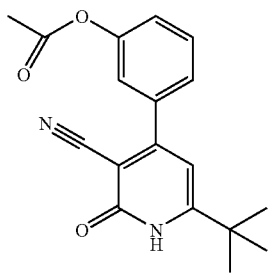

Analogously to Example 32b, 376 mg of product is obtained from 396 mg of the compound that is described under Example 37a and 370 µl of acetic acid anhydride in pyridine.

$^1$H-NMR (d6-DMSO): δ=1.31 (9H); 2.29 (3H); 6.25 (1H); 7.34 (1H); 7.42 (1H); 7.52-7.65 (2H); 12.35 (1H) ppm.

EXAMPLE 37c

Production of Acetic Acid 3-(6-tert-Butyl-3-cyano-2-trifluoromethane-sulfonyloxy-pyridin-4-yl)-phenyl ester

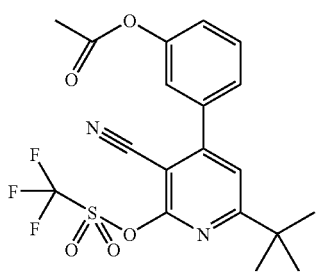

Analogously to Example 3b, 480 mg of product is obtained from 371 mg of the substance that is described under Example 37a and 605 µl of trifluoromethanesulfonic acid in pyridine.

$^1$H-NMR (CDCl$_3$): δ=1.40 (9H); 2.35 (3H); 7.28-7.37 (2H); 7.45-7.53 (2H); 7.59 (1H) ppm.

EXAMPLE 37d

Production of 3-(3-Amino-6-tert-butyl-1H-pyrazolo[3,4-b]pyridin-4-yl)-phenol

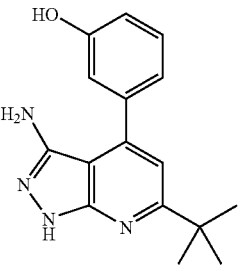

Analogously to Example 1c, 147 mg of product is obtained from 477 mg of the substance that is described under Example 37c with 200 µl of hydrazine hydrate solution (80%) in propanol.

$^1$H-NMR (d6-DMSO): δ=1.38 (9H); 4.52 (2H); 6.37-7.00 (4H); 7.36 (1H); 9.75 (1H); 12.14 (1H) ppm.

EXAMPLE 38

Production of 3-(3-Amino-6-tert-butyl-1H-pyrazolo[3,4-b]pyridin-4-yl)-4-methyl-phenol

EXAMPLE 38a

Production of 6-tert-Butyl-4-[5-(tert-butyl-dimethyl-silanyloxy)-2-methyl-phenyl]-2-oxo-1,2-dihydro-pyridine-3-carbonitrile

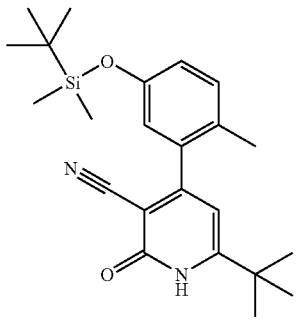

Analogously to Example 1a, 1.13 g of product is obtained from 5 g of ammonium acetate, 865 µl of cyanoacetic acid ethyl ester, 1 ml of 3,3-dimethyl-2-butanone and 2.03 g of the substance that is described under Example 35f.

EXAMPLE 38b

Production of Trifluoromethanesulfonic Acid 6-tert-Butyl-4-[5-(tert-butyl-dimethyl-silanyloxy)-2-methyl-phenyl]-3-cyano-pyridin-2-yl Ester

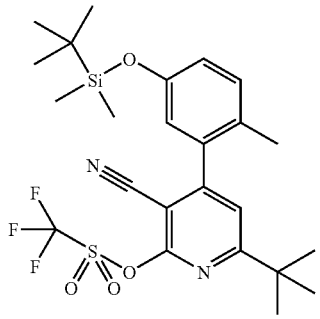

Analogously to Example 3b, 352 mg of product is obtained from 330 mg of the substance that is described under Example 38a and 200 μl of trifluoromethanesulfonic acid in pyridine.

EXAMPLE 38c

Production of 6-tert-Butyl-4-[5-(tert-butyl-dimethyl-silanyloxy)-2-methyl-phenyl]-1H-pyrazolo[3,4-b]pyridin-3-ylamine

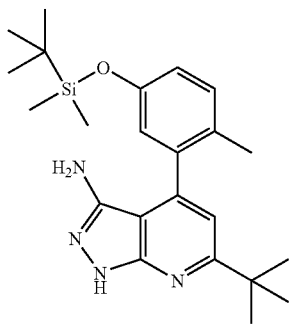

Analogously to Example 1c, 189 mg of product is obtained from 367 mg of the substance that is described under Example 38b with 150 μl of hydrazine hydrate solution (80%) in propanol.

EXAMPLE 38d

Production of 3-(3-Amino-6-tert-butyl-1H-pyrazolo[3,4-b]pyridin-4-yl)-4-methyl-phenol

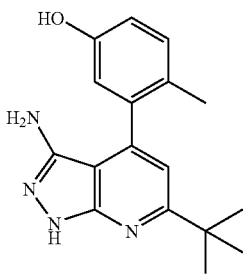

Analogously to Example 35j, 64 mg of product is obtained from 150 mg of the substance that is described under Example 38c.

$^1$H-NMR (d6-DMSO): δ=1.34 (9H); 1.96 (3H); 4.23 (2H); 6.62 (1H); 6.75-6.86 (2H); 7.17 (1H); 9.48 (1H); 12.08 (1H) ppm.

EXAMPLE 39

Production of 4-(3,5-Dimethoxy-phenyl)-6-pyridin-4-yl-1H-pyrazolo[3,4-b]pyridin-3-ylamine

EXAMPLE 39a

Production of 6-tert-Butyl-4-(3,5-dimethoxyphenyl)-2-oxo-1,2-dihydro-pyridine-3-carbonitrile

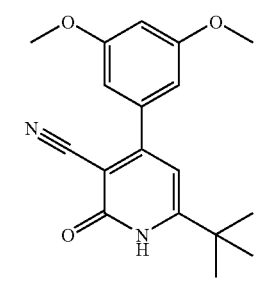

Analogously to Example 1a, 600 mg of product is obtained from 3.71 g of ammonium acetate, 645 μl of cyanoacetic acid ethyl ester, 745 μl of 3,3-dimethyl-2-butanone and 1 g of 3,5-dimethoxy benzaldehyde.

$^1$H-NMR (d6-DMSO): δ=1.30 (9H); 3.80 (6H); 6.27 (1H); 6.68 (1H); 6.77 (2H) ppm.

EXAMPLE 39b

Production of Trifluoromethanesulfonic acid-6-tert-butyl-3-cyano-4-(3,5-dimethoxyphenyl)pyridin-2-yl ester

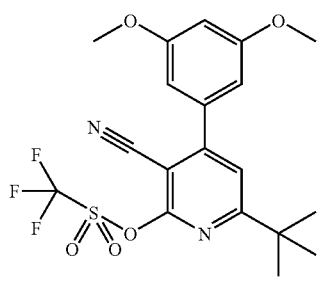

Analogously to Example 3b, 382 mg of product is obtained from 290 mg of the substance that is described under Example 39a and 470 μl of trifluoromethanesulfonic acid in pyridine.

$^1$H-NMR (CDCl$_3$): δ=1.38 (9H); 3.86 (6H); 6.61 (1H); 6.69 (2H); 7.46 (1H) ppm.

EXAMPLE 39c

Production of 6-tert-Butyl-4-(3,5-dimethoxyphenyl)-1H-pyrazolo[3,4-b]pyridin-3-ylamine

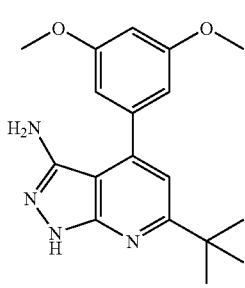

Analogously to Example 1c, 126 mg of product is obtained from 377 mg of the substance that is described under Example 39b with 155 μL of hydrazine hydrate solution (80%) in propanol.

$^1$H-NMR (d6-DMSO): δ=1.35 (9H); 3.80 (6H); 4.53 (2H); 6.62 (1H); 6.70 (2H); 7.00 (1H); 12.15 (1H) ppm.

EXAMPLE 40

Production of 3-(3-Amino-6-tert-butyl-1H-pyrazolo3,4-b]pyridin-4-yl)-5-isopropoxy Phenol

EXAMPLE 40a

Production of 2-(3-Isopropoxy-5-methoxy-phenyl)-[1,3]dioxolane

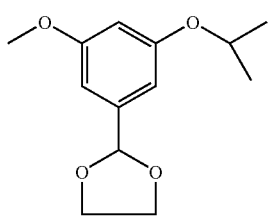

3.42 ml of azodicarboxylic acid diethyl ester is slowly added in drops to a solution of 2.85 g of the compound that is described under Example 33b, 5.7 g of triphenylphosphine and 1.7 ml of 2-propanol in 20 ml of tetrahydrofuran at 0° C. It is allowed to stir for 20 more minutes at 23° C., and then the reaction mixture is poured into 10 ml of hexane. Then, it is stirred for 15 more minutes and then filtered over Celite. The crude product is purified by column chromatography. 2.94 g of product is obtained.

$^1$H-NMR (CDCl$_3$): δ=1.30 (6H); 3.78 (3H); 4.00-4.15 (4H); 4.53 (1H); 5.76 (1H); 6.42 (1H); 6.62 (2H) ppm.

EXAMPLE 40b

Production of 3-[1,3]Dioxolan-2-yl-5-isopropoxy Phenol

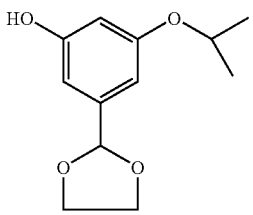

Analogously to Example 33b, 1.91 g of product is obtained from 2.94 g of the compound that is described under 40a and 3.46 g of sodium methanethiolate in N,N-dimethylformamide after column chromatography.

$^1$H-NMR (CDCl$_3$): δ=1.30 (6H); 3.98-4.15 (4H); 4.51 (1H); 5.20 (1H); 6.37 (1H); 6.51 (1H); 6.60 (1H) ppm.

EXAMPLE 40c

Production of 3-Hydroxy-5-isopropoxybenzaldehyde

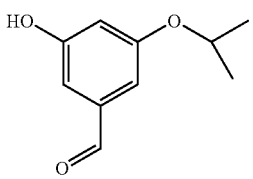

Analogously to Example 33c, 1.46 g of product is obtained from 2.08 g of the substance that is described under 40b with 2N hydrochloric acid in acetone.

$^1$H-NMR (CDCl$_3$): δ=1.35 (6H); 4.58 (1H); 5.61 (1H); 6.66 (1H); 6.91 (1H); 6.98 (1H); 9.87 (1H) ppm.

EXAMPLE 40d

Production of 6-tert-Butyl-4-(3-hydroxy-5-isopropoxy-phenyl)-2-oxo-1,2-dihydro-pyridine-3-carbonitrile

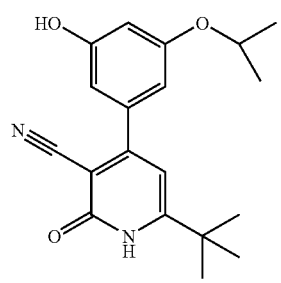

1.12 g of product is obtained [from] 1.46 g of the compound that is described under Example 40c, 5 g of ammonium acetate, 865 µl of cyanoacetic acid ethyl ester and 1 ml of 3,3-dimethyl-2-butanone.

¹H-NMR (d6-DMSO): δ=1.20-1.40 (15H); 4.60 (1H); 6.20 (1H); 6.47 (1H); 6.57 (2H); 9.82 (1H) ppm.

EXAMPLE 40e

Production of Acetic Acid 3-(6-tert-butyl-3-cyano-2-oxo-1,2-dihydro-pyridin-4-yl)-5-isopropoxyphenyl Ester

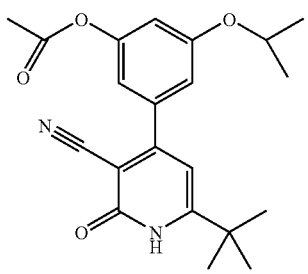

Analogously to Example 32b, 407 mg of product is obtained from 460 mg of the compound that is described under Example 40d and 265 µl of acetic acid anhydride in pyridine.

¹H-NMR (CDCl₃): δ=1.36 (6H); 1.42 (9H); 2.31 (3H); 4.58 (1H); 6.30 (1H); 6.77 (1H); 6.89 (1H); 7.00 (1H); 12.26 (1H) ppm.

EXAMPLE 40f

Production of Acetic Acid 3-(6-tert-butyl-3-cyano-2-trifluoromethane-sulfonyloxypyridin-4-yl)-5-isopropoxyphenyl Ester

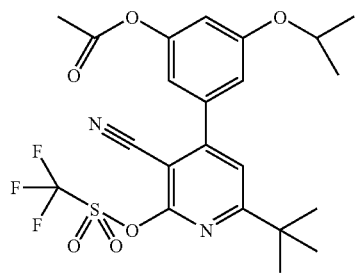

Analogously to Example 3b, 490 mg of product is obtained from 404 mg of the substance that is described under Example 40e and 555 µl of trifluoromethanesulfonic acid in pyridine.

¹H-NMR (CDCl₃): δ=1.32-1.42 (15H); 2.32 (3H); 4.58 (1H); 6.80 (1H); 6.88 (1H); 6.96 (1H); 7.46 (1H) ppm.

EXAMPLE 40g

Production of 3-(3-Amino-6-tert-butyl-1H-pyrazolo3,4-b]pyridin-4-yl)-5-isopropoxy-phenol

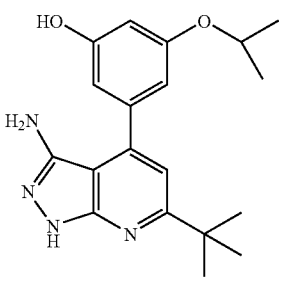

Analogously to Example 1c, 167 mg of product is obtained from 486 mg of the substance that is described under Example 40f with 180 µl of hydrazine hydrate solution (80%) in propanol.

¹H-NMR (d6-DMSO): δ=1.28 (6H); 1.37 (9H); 4.54-4.68 (3H); 6.42 (1H); 6.50 (2H); 6.95 (1H); 9.73 (1H); 12.12 (1H) ppm.

EXAMPLE 41

Production of 3-(3-Amino-6-tert-butyl-1H-pyrazolo[3,4b]pyridin-4-yl)-4-nitro-phenol

EXAMPLE 41a

Production of 6-tert-Butyl-4-(5-hydroxy-2-nitrophenyl)-2-oxo-1,2-dihydro-pyridine-3-carbonitrile

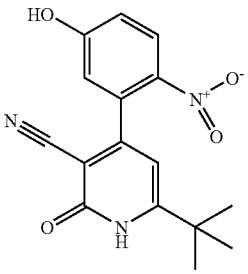

Analogously to Example 1a, 690 mg of product is obtained from 3.7 g of ammonium acetate, 640 µl of cyanoacetic acid ethyl ester, 740 µl of 3,3-dimethyl-2-butanone and 1 g of 5-hydroxy-2-nitrobenzaldehyde.

¹H-NMR (d6-DMSO): δ=1.29 (9H); 6.25 (1H); 6.81 (1H); 7.06 (1H); 8.21 (1H); 12.37 (1H) ppm.

EXAMPLE 41b

Production of Acetic Acid-3-(6-tert-butyl-3-cyano-2-oxo-1,2-dihydropyridin-4-yl)-4-nitrophenyl Ester

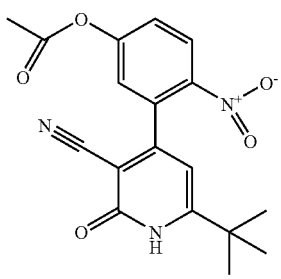

Analogously to Example 33b, 143 mg of product is obtained from 200 mg of the compound that is described under Example 41a and 120 μl of acetic acid anhydride in pyridine.
$^1$H-NMR (CDCl$_3$): δ=1.35 (3H); 2.35 (3H); 6.10 (1H); 7.22 (1H); 7.42 (1H); 8.29 (1H) ppm.

EXAMPLE 41c

Production of Acetic Acid 3-(6-tert-butyl-3-cyano-2-trifluoromethane-sulfonyloxy-pyridin-4-yl)-4-nitrophenyl Ester

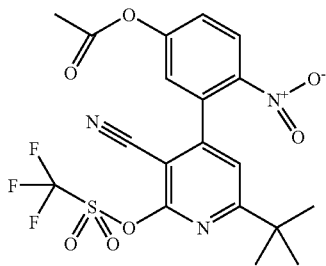

Analogously to Example 3b, 105 mg of product is obtained from 143 mg of the substance that is described under Example 41b and 205 μl of trifluoromethanesulfonic acid in pyridine.
$^1$H-NMR (CDCl$_3$): δ=1.38 (9H); 1.55 (3H); 7.32 (1H); 7.39 (1H); 7.68 (1H); 8.43 (1H) ppm.

EXAMPLE 41d

Production of 3-(3-Amino-6-tert-butyl-1H-pyrazolo[3,4b]pyridin-4-yl)-4-nitro-phenol

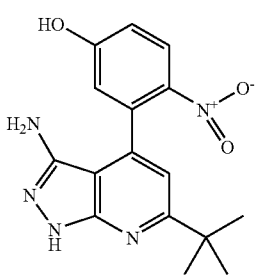

Analogously to Example 1c, 147 mg of product is obtained from 477 mg of the substance that is described under Example 41 with 200 μl of hydrazine hydrate solution (80%) in propanol.
$^1$H-NMR (d6-DMSO): δ=1.35 (9H); 4.30 (2H); 6.72 (1H); 6.88 (1H); 7.00 (1H); 8.16 (1H); 12.10 (1H) ppm.

EXAMPLE 42

Production of 5-(3-Amino-6-tert-butyl-1H-pyrazolo[3,4-b]pyridin-4-yl)-2,3-dimethoxyphenol

EXAMPLE 42a

Production of 6-tert-Butyl-4-(3-hydroxy-4,5-dimethoxy-phenyl)-2-oxo-1,2-dihydro-pyridine-3-carbonitrile

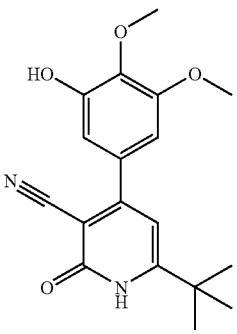

Analogously to Example 1a, 340 mg of product is obtained from 1.7 g of ammonium acetate, 300 μl of cyanoacetic acid ethyl ester, 340 μl of 3,3-dimethyl-2-butanone and 500 mg of 3,4-dimethoxy-5-hydroxybenzaldehyde.
$^1$H-NMR (d6-DMSO): δ=1.30 (9H); 3.72 (3H); 3.82 (3H); 6.22 (1H); 6.76 (2H); 9.62 (1H); 12.21 (1H) ppm.

EXAMPLE 42b

Production of Acetic Acid 5-(6-tert-butyl-3-cyano-2-oxo-1,2-dihydro-pyridin-4-yl)-2,3-dimethoxyphenyl Ester

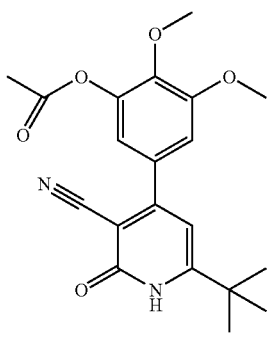

Analogously to Example 33b, 180 mg of product is obtained from 160 mg of the compound that is described under Example 42a and 100 μl of acetic acid anhydride in pyridine.

$^1$H-NMR (CDCl$_3$): δ=1.42 (9H); 2.36 (3H); 3.91 (3H); 3.95 (3H); 6.29 (1H); 6.90 (1H); 7.18 (1H) ppm.

EXAMPLE 42c

Production of Acetic Acid 5-(6-tert-butyl-3-cyano-2-trifluoro-methanesulfonyloxypyridin-4-yl)-2,3-dimethoxyphenyl Ester

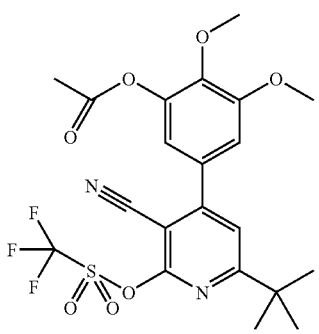

Analogously to Example 3b, 215 mg of product is obtained from 180 mg of the substance that is described under Example 42b and 250 μl of trifluoromethanesulfonic acid in pyridine.

$^1$H-NMR (CDCl$_3$): δ=1.40 (9H); 2.36 (3H); 3.92 (3H); 3.97 (3H); 6.90 (1H); 7.11 (1H); 7.43 (1H) ppm.

EXAMPLE 42d

Production of 5-(3-Amino-6-tert-butyl-1H-pyrazolo[3,4b]pyridin-4-yl)-2,3-dimethoxyphenol

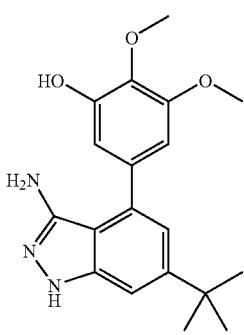

Analogously to Example 1c, 90 mg of product is obtained from 210 mg of the substance that is described under Example 42c with 80 μl of hydrazine hydrate solution (80%) in propanol.

$^1$H-NMR (d6-DMSO): δ=1.38 (9H); 3.73 (3H); 3.82 (3H); 4.59 (2H); 6.68 (2H); 6.96 (1H); 9.51 (1H); 12.12 (1H) ppm.

EXAMPLE 43

Production of 6-Cyclopropyl-4-(3,4-dichlorophenyl)-1H-pyrazolo-[3,4-b]pyridin-3-ylamine

EXAMPLE 43a

Production of 6-Cyclopropyl-4-(3,4-dichlorophenyl)-2-oxo-1,2-dihydropyridine-3-carbonitrile

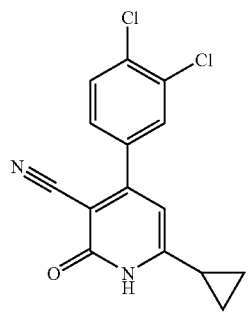

While being stirred, 300 ml of ethanol is mixed with 14 g of acetyl cyclopropane, 18 g of cyanoacetic acid ethyl ester, 28 g of 3,4-dichlorobenzaldehyde as well as 100 g of ammonium acetate, and it is subsequently heated to boiling for six hours at a bath temperature of 80-90° C. After some length of time, a portion of the product already precipitates from the reaction solution. To complete the precipitation, it is then allowed to cool to room temperature while being stirred. The precipitate is suctioned off, washed acetate-free with cold ethanol and water and ultimately dried. 15 g of product accumulates, melting point 290-295° C., while decomposing.

EXAMPLE 43b

Production of 2-Chloro-6-cyclopropyl-4-(3,4-dichlorophenyl)-nicotinonitrile

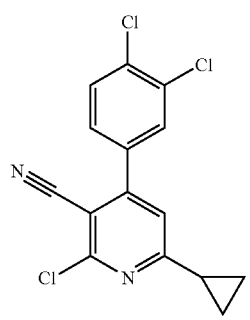

16 g of pyridone (the Example given above) is carefully introduced into 75 ml of phenylphosphonic acid dichloride, and the mixture is then stirred for four hours in a moisture-free environment at 150-160° C. Under these conditions, the pyridone goes into solution as soon as possible. For working-up, it is allowed to cool to room temperature, and then carefully stirred in water. The precipitate that is produced is suctioned off, washed with water and dried in air. Yield 11 g, melting point 158-160° C. (propanol).

EXAMPLE 43c

Production of 6-Cyclopropyl-4-(3,4-dichlorophenyl)-1H-pyrazolo[3,4-b]pyridin-3-ylamine

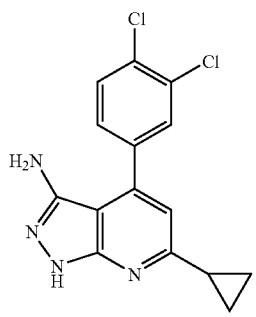

A solution of 0.971 g of the chlorocyanopyridine above in 10 ml of propanol and 1 ml of hydrazine hydrate (80%) is heated for four hours at 100° C. After the reaction mixture is cooled, the precipitated product is suctioned off and recrystallized from acetic acid. Yield 250 mg, melting point 256-258° C.

EXAMPLE 44

Production of 3-(3-Amino-6-cyclopropyl-1H-pyrazolo-[3,4-b]pyridin-4-yl)-phenol

EXAMPLE 44a

Production of 6-Cyclopropyl-4-(3-hydroxy-phenyl)-2-oxo-1,2-dihydropyridine-3-carbonitrile

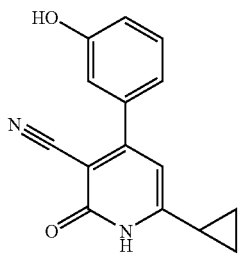

Analogously to Example 1a, 750 mg of product is obtained from 5 g of ammonium acetate, 875 µl of cyanoacetic acid ethyl ester, 815 µl of cyclopropylmethylketone and 1 g of 3-hydroxybenzaldehyde.

$^1$H-NMR (d6-DMSO): δ=1.00-1.25 (4H); 1.97 (1H); 5.99 (1H); 6.86-7.05 (3H); 7.30 (1H); 9.80 (1H); 12.58 (1H) ppm.

EXAMPLE 44b

Production of Acetic Acid 3-(3-cyano-6-cyclopropyl-2-oxo-1,2-dihydro-pyridin-4-yl)-phenyl Ester

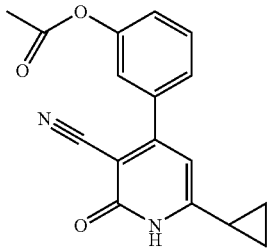

Analogously to Example 33b, 570 mg of product is obtained from 750 mg of the compound that is described under Example 44a and 5500 µl of acetic acid anhydride in pyridine.

$^1$H-NMR (CDCl$_3$): δ=1.12 (2H); 1.31 (2H); 2.07 (1H); 2.33 (3H); 5.96 (1H); 7.20-7.33 (2H); 7.50 (2H); 13.46 (1H) ppm.

EXAMPLE 44c

Production of Acetic Acid 3-(3-cyano-6-cyclopropyl-2-trifluoromethane-sulfonyloxypyridin-4-yl)-phenyl Ester

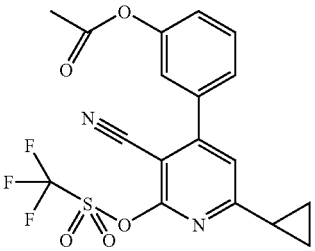

Analogously to Example 3b, 458 mg of product is obtained from 350 mg of the substance that is described under Example 44b and 600 µl of trifluoromethanesulfonic acid in pyridine.

$^1$H-NMR (CDCl$_3$): δ=1.22 (4H); 2.10 (1H); 2.33 (3H); 7.27-7.38 (2H); 7.39 (1H); 7.49 (1H); 7.56 (1H) ppm.

EXAMPLE 44d

Production of 3-(3-Amino-6-cyclopropyl-1H-pyrazolo-[3,4-b]pyridin-4-yl)-phenol

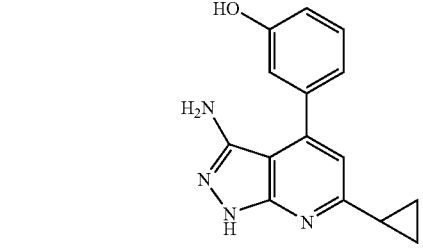

Analogously to Example 1c, 208 mg of product is obtained from 453 mg of the substance that is described under Example 44c with 200 µl of hydrazine hydrate solution (80%) in propanol.

¹H-NMR (d6-DMSO): δ=0.93-1.14 (4H); 2.19 (1H); 4.49 (2H); 6.83 (1H); 6.88-7.00 (3H); 7.34 (1H); 9.78 (1H); 12.01 (1H) ppm.

EXAMPLE 45

Production of 3-(3-Amino-6-cyclohexyl-1H-pyrazolo-[3,4-b]pyridin-4-yl)-phenol

EXAMPLE 45a

Production of 6-Cyclohexyl-4-(3-hydroxy-phenyl)-2-oxo-1,2-dihydro-pyridine-3-carbonitrile

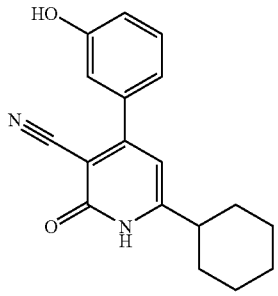

Analogously to Example 1a, 750 mg of product is obtained from 5 g of ammonium acetate, 875 µl of cyanoacetic acid ethyl ester, 1.13 ml of 3,3-dimethyl-2-butanone and 1 g of 3-hydroxybenzaldehyde.

¹H-NMR (d6-DMSO): δ=1.10-1.40 (4H); 1.40-1.60 (2H); 1.62-1.91 (4H); 2.53 (1H); 6.23 (1H); 6.88-7.06 (3H); 7.32 (1H); 9.81 (1H); 12.49 (1H) ppm.

EXAMPLE 45b

Production of Acetic Acid 3-(3-cyano-6-cyclohexyl-2-oxo-1,2-dihydro-pyridin-4-yl)-phenyl Ester

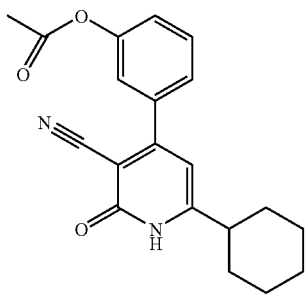

Analogously to Example 33b, 720 mg of product is obtained from 743 mg of the compound that is described under Example 45a and 470 µl of acetic acid anhydride in pyridine.

¹H-NMR (d6-DMSO): δ=1.10-1.38 (4H); 1.40-1.60 (2H); 1.60-1.90 (4H); 2.30 (3H); 2.53 (1H); 6.29 (1H); 7.32 (1H); 7.40 (1H); 7.50-7.65 (2H); 12.56 (1H) ppm.

EXAMPLE 45c

Production of Acetic Acid 3-(3-cyano-6-cyclohexyl-2-trifluoromethane-sulfonyloxy-pyridin-4-yl)phenyl Ester

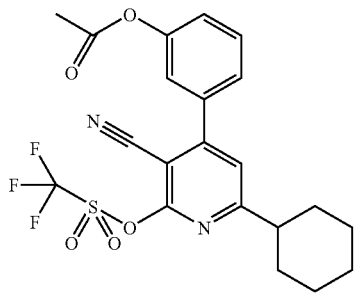

Analogously to Example 3b, 385 mg of product is obtained from 365 mg of the substance that is described under Example 45b and 550 µl of trifluoromethanesulfonic acid in pyridine.

¹H-NMR (CDCl₃): δ=1.20-1.62 (5H); 1.77 (1H); 1.82-2.02 (4H); 2.33 (3H); 2.78 (1H); 7.23-7.37 (3H); 7.49 (1H); 7.57 (1H) ppm.

EXAMPLE 45d

Production of 3-(3-Amino-6-cyclohexyl-1H-pyrazolo-[3,4-b]pyridin-4-yl)-phenol

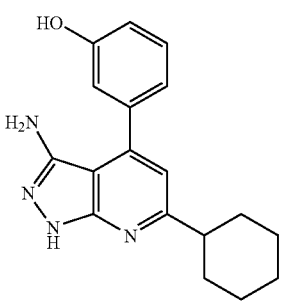

Analogously to Example 1c, 165 mg of product is obtained from 380 mg of the substance that is described under Example 45c with 150 µl of hydrazine hydrate solution (80%) in propanol.

¹H-NMR (d6-DMSO): δ=1.15-1.50 (4H); 1.50-1.97 (6H); 2.75 (1H); 4.51 (2H); 6.78 (1H); 6.85-7.00 (3H); 7.33 (1H); 9.75 (1H); 12.10 (1H) ppm.

EXAMPLE 46

Production of 5-(3-Amino-6-tert-butyl-1H-pyrazolo [3,4-b]pyridin-4-yl)-2-methoxyphenol

EXAMPLE 46a

Production of 6-tert-Butyl-4-(3-hydroxy-4-methoxyphenyl)-2-oxo-1,2-dihydro-pyridine-3-carbonitrile

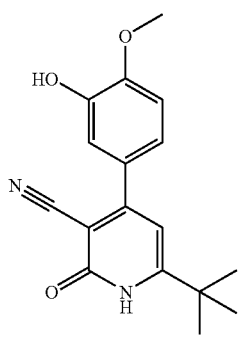

Analogously to Example 1a, 660 mg of product is obtained from 4.1 g of ammonium acetate, 700 µl of cyanoacetic acid ethyl ester, 815 µl of 3,3-dimethyl-2-butanone and 1 g of 3-hydroxy-4-methoxybenzaldehyde.

$^1$H-NMR (d6-DMSO): δ=1.28 (9H); 3.84 (3H); 6.19 (1H); 7.08 (3H); 9.41 (1H); 12.13 (1H) ppm.

46b

Production of Acetic Acid 5-(6-tert-butyl-3-cyano-2-oxo-1,2-dihydro-pyridin-4-yl)-2-methoxyphenyl Ester

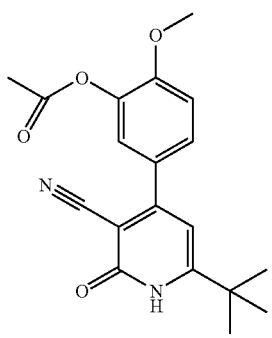

Analogously to Example 33b, 413 mg of product is obtained from 435 mg of the compound that is described under Example 46a and 270 µl of acetic acid anhydride in pyridine.

$^1$H-NMR (CDCl$_3$): δ=1.42 (9H); 2.34 (3H); 3.91 (3H); 6.29 (1H); 7.10 (1H); 7.31 (1H); 7.60 (1H); 12.18 (1H) ppm.

EXAMPLE 46c

Production of Acetic Acid 5-(6-tert-Butyl-3-cyano-2-trifluoromethane-sulfonyloxy-pyridin-4-yl)-2-methoxy-phenyl Ester

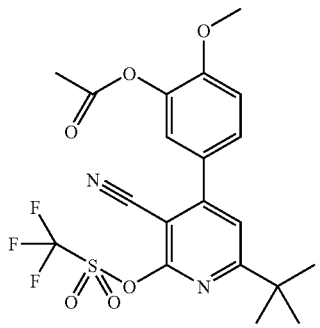

Analogously to Example 3b, 501 mg of product is obtained from 408 mg of the substance that is described under Example 46b and 605 µl of trifluoromethanesulfonic acid in pyridine.

$^1$H-NMR (CDCl$_3$): δ=1.38 (9H); 2.35 (3H); 3.91 (3H); 7.12 (1H); 7.31 (1H); 7.42 (1H); 7.56 (1H) ppm.

EXAMPLE 46d

Production of 5-(3-Amino-6-tert-butyl-1H-pyrazolo [3,4-b]pyridin-4-yl)-2-methoxyphenol

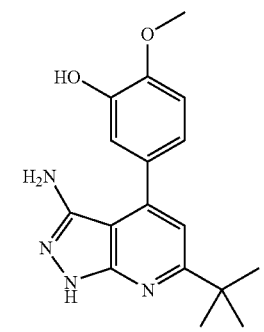

Analogously to Example 1c, 145 mg of product is obtained from 496 mg of the substance that is described under Example 46c with 190 µl of hydrazine hydrate solution (80%) in propanol.

$^1$H-NMR (d6-DMSO): δ=1.35 (9H); 3.83 (3H); 4.56 (2H); 6.90 (1H); 6.99 (2H); 7.10 (1H); 9.31 (1H); 12.10 (1H) ppm.

EXAMPLE 47

Production of 5-(3-Amino-6-tert-butyl-1H-pyrazolo[3,4-b]pyridin-4-yl)-benzene-1,3-diol

EXAMPLE 47A

Production of 6-tert-Butyl-4-(3,5-dihydroxyphenyl)-2-oxo-1,2-dihydropyridine-3-carbonitrile

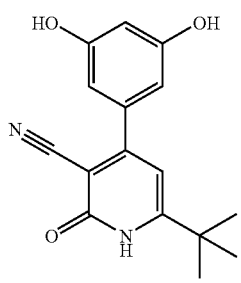

Analogously to Example 1a, 850 mg of product is obtained from 6.46 g of ammonium acetate, 770 μl of cyanoacetic acid ethyl ester, 895 μl of 3,3-dimethyl-2-butanone and 1 g of 3,5-dihydroxybenzaldehyde.

$^1$H-NMR (d6-DMSO): δ=1.30 (9H); 6.15 (2H); 6.36 (1H); 6.43 (1H); 9.67 (2H); 12.23 (1H) ppm.

EXAMPLE 47b

Production of Acetic Acid 3-Acetoxy-5-(6-tert-butyl-3-cyano-2-oxo-1,2-dihydro-pyridin-4-yl)-phenyl Ester

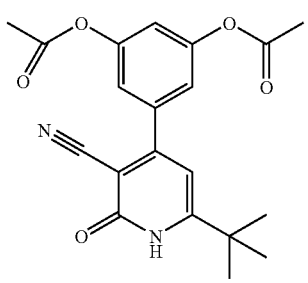

Analogously to Example 33b, 210 mg of product is obtained from 200 mg of the compound that is described under Example 47a and 350 μl of acetic acid anhydride in pyridine.

$^1$H-NMR (CDCl$_3$): δ=1.40 (9H); 2.31 (6H); 6.38 (1H); 7.10 (1H); 7.28 (2H); 12.07 (1H) ppm.

EXAMPLE 47c

Production of Acetic Acid 3-Acetoxy-5-(6-tert-butyl-3-cyano-2-trifluoromethanesulfonyloxy-pyridin-4-yl)-phenyl Ester

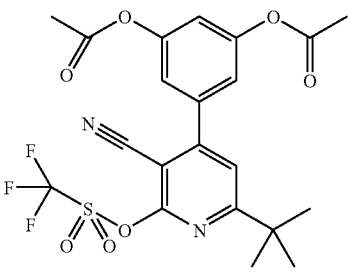

Analogously to Example 3b, 67 mg of product is obtained from 110 mg of the substance that is described under Example 47b and 150 μl of trifluoromethanesulfonic acid in pyridine.

$^1$H-NMR (CDCl$_3$): δ=1.39 (9H); 2.32 (6H); 7.16 (1H); 7.26 (2H); 7.47 (1H) ppm.

EXAMPLE 47d

Production of 5-(3-Amino-6-tert-butyl-1H-pyrazolo[3,4-b]pyridin-4-yl)-benzene-1,3-diol

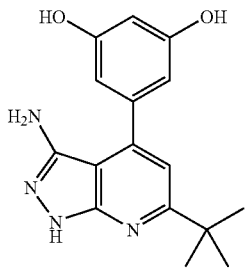

Analogously to Example 1c, 25 mg of product is obtained from 60 mg of the substance that is described under Example 47c with 22 μl of hydrazine hydrate solution (80%) in propanol.

$^1$H-NMR (d6-DMSO): δ=1.37 (9H); 4.60 (2H); 6.35 (3H); 6.90 (1H); 9.59 (2H); 12.1 (1H) ppm.

EXAMPLE 48

Production of 4-Isopropyl-6-(3,4-methylenedioxyphenyl)-1H-pyrazolo[3,4b]pyridin-3-ylamine

EXAMPLE 48a

Production of 4-Isopropyl-6-(3,4-methylenedioxyphenyl)-2-oxo-1,2-dihydropyridine-3-carbonitrile

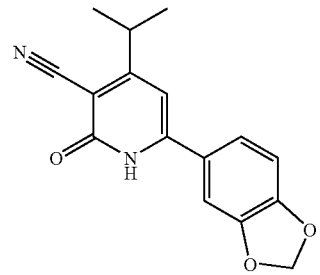

100 g of ammonium acetate is added to a solution of 12 g of isobutyraldehyde, 26 g of 3,4-methylenedioxy-acetophenone and 18 g of cyanoacetic acid ethyl ester in 300 ml of ethanol, and it is then refluxed for six hours while being stirred (80-90° C.). After cooling, the precipitate is suctioned off, washed first with cold ethanol and then with water and dried in air. Yield 17 g, melting point 266-268° C.

EXAMPLE 48b

Production of 2-Chloro-4-isopropyl-6-(3,4-methylenedioxyphenyl)-nicotinonitrile

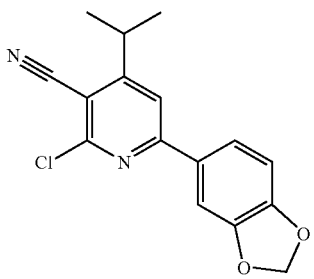

A mixture of 15 g of 2-pyridone (the Example given above) and 75 ml of phenylphosphonic acid dichloride is heated for four hours in a nitrogen atmosphere in a moisture-free environment to 150-160° C. After cooling, the reaction mixture is carefully stirred into ice water, the precipitate is suctioned off, washed carefully with water and dried in air. Yield 16 g, melting point 171-173° C.

EXAMPLE 48c

Production of 4-Isopropyl-6-(3,4-methylenedioxyphenyl)-1H-pyrazolo[3,4-b]pyridin-3-ylamine

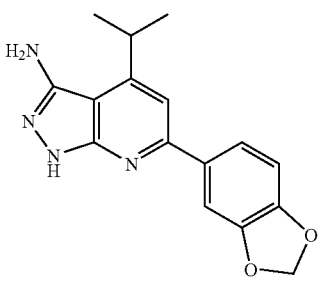

300 mg of chloronicotinonitrile (the Example given above) is mixed in 3 ml of propanol with 1 ml of hydrazine hydrate and heated for four hours while being stirred at 100° C. After half the reaction time, a second portion of hydrazine hydrate (0.5 ml) is added to the reaction solution. For working-up, the product is precipitated by the addition of water. The precipitate is suctioned off, washed with water, cold isopropanol and diethyl ether, and dried in air. Yield 200 mg, melting point 184-186° C.

EXAMPLE 49

Production of 6-(3-Hydroxyphenyl)-4-(4-pyridyl)-1H-pyrazolo[3,4b]-pyridin-3-ylamine

EXAMPLE 49a

Production of 6-(3-Hydroxyphenyl)-2-oxo-4-(4-pyridyl)-1,2-dihydropyridine-3-carbonitrile

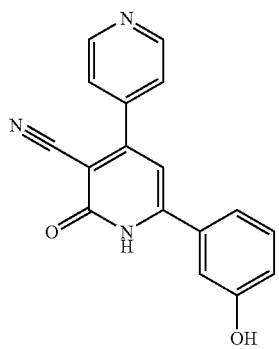

According to the general production procedure for 2-pyridones, and after six hours of reaction time at 80° C., a total of 8 g of the title compound accumulates from a batch with 50 g of ammonium acetate, 11 g of 3-hydroxyacetophenone, 9 g of cyanoacetic acid ethyl ester and 8 g of 4-pyridinaldehyde in 300 ml of ethanol.

EXAMPLE 49b

Production of 6-(3-Acetyloxyphenyl)-2-oxo-4-(4-pyridyl)-1,2-dihydropyridine-3-carbonitrile

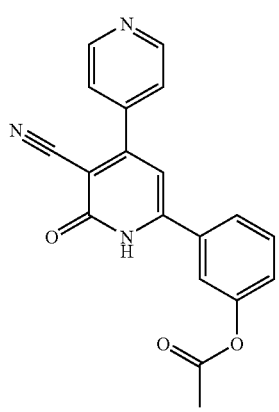

8 g of pyridone (the Example given above) is introduced into 80 ml of pyridine, mixed with 6 ml of acetic acid anhydride while being stirred quickly, and the reaction mixture is then kept for two hours at 80° C. For working-up, it is allowed to cool and stirred into ice water. The precipitate is suctioned off, washed with water and dried in air. Yield 7 g, melting point 284-286° C.

EXAMPLE 49c

Production of 6-(3-Acetyloxyphenyl)-4-(4-pyridyl)-2-trifluoromethyl-sulfonyl-oxynicotinonitrile

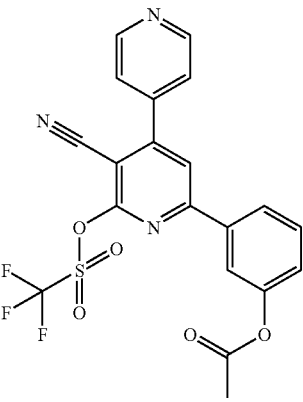

1 ml of trifluoromethanesulfonic acid anhydride is added in drops in a moisture-free environment to a suspension of 1 g of the acetylated pyridone (the Example given above) in 10 ml of pyridine while being cooled in an ice bath. Then, the ice bath is removed, and it is allowed to stir for two hours at room temperature. For working-up, the homogeneous, dark-colored reaction solution is introduced into ice water, the precipitate is suctioned off, washed with water, and dried. The crude product (1 g) can be recrystallized from diethyl ether. Yield 720 mg.

EXAMPLE 49d

Production of 6-(3-Hydroxyphenyl)-4-(4-pyridyl)-1H-pyrazolo[3,4-b]pyridin-3-ylamine

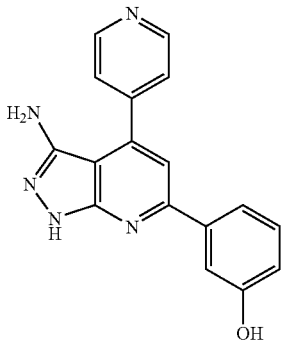

A suspension of 980 mg of triflate (the Example given above) in 25 ml of propanol is mixed with 1 ml of hydrazine hydrate (80%), and the mixture is stirred for 6 hours at a bath temperature of 100° C. After some length of time, the reaction solution is homogeneous. To complete the reaction, another 0.4 ml of hydrazine hydrate solution is added after three hours. The product precipitates while the reaction solution cools. The precipitate is suctioned off, washed with propanol and ether, and ultimately dried. Yield 420 mg.

$^1$H-NMR (DMSO-$d_6$) δ=4.68 (s, 2H); 6.86 (dd, 1H); 7.29 (t, 1H); 7.45 (s, 1H); 7.59 (m, 2H); 7.70 (d, 2H); 8.76 (d, 2H); 9.55 (brs, 1H); 12.42 (s, 1H) ppm.

The following compounds are produced analogously to the above-described examples:

EXAMPLE 50

4-(4-Chlorophenyl)-6-phenyl-1H-pyrazolo[3,4-b]pyridin-3-ylamine

EXAMPLE 51

6-Cyclopropyl-4-(3,4-dichlorophenyl)-1H-pyrazolo[3,4-b]pyridin-3-ylamine

EXAMPLE 52

5-[3-Amino-6-(4-fluorophenyl)-1H-pyrazolo[3,4-b]pyridin-4-yl]-2-methoxyphenol

EXAMPLE 53

6-Pyridin-3-yl-4-quinolin-3-yl-1H-pyrazolo[3,4-b]pyridin-3-ylamine

EXAMPLE 54

6-(3-Chlorophenyl)-4-(1H-indol-3-yl)-1H-pyrazolo[3,4-b]pyridin-3-ylamine

EXAMPLE 55

4-[3-Amino-6-(3-methoxyphenyl)-1H-pyrazolo[3,4-b]pyridin-4-yl]-benzonitrile

EXAMPLE 56

4-(4-Chlorophenyl)-6-cyclopropyl-1H-pyrazolo[3,4-b]pyridin-3-ylamine

EXAMPLE 57

6-Cyclopropyl-4-(3-nitrophenyl)-1H-pyrazolo[3,4-b]pyridin-3-ylamine

EXAMPLE 58

6-(4-Morpholin-4-yl-phenyl)-4-pyridin-4-yl-1H-pyrazolo[3,4-b]pyridin-3-ylamine

EXAMPLE 59

4-[4-(3-Dimethylaminopropoxy)phenyl]-6-(4-fluorophenyl)-1H-pyrazolo[3,4-b]pyridin-3-ylamine

EXAMPLE 60

6-Cyclopropyl-4-(4-trifluoromethylphenyl)-1H-pyrazolo[3,4-b]pyridin-3-ylamine

EXAMPLE 61

4-(3-Amino-6-cyclopropyl-1H-pyrazolo[3,4-b]pyridin-4-yl)-benzonitrile

EXAMPLE 62

4-(1H-Imidazol-2-yl)-6-(4-phenoxy-phenyl)-1H-pyrazolo[3,4-b]pyridin-3-ylamine

EXAMPLE 63

Production of 6-tert-Butyl-4-(4-nitro-phenyl)-1H-pyrazolo[3,4b]pyridin-3-ylamine

EXAMPLE 63a

Production of 6-tert-Butyl-4-(4-nitro-phenyl)-2-oxo-1,2-dihydro-pyridine-3-carbonitrile

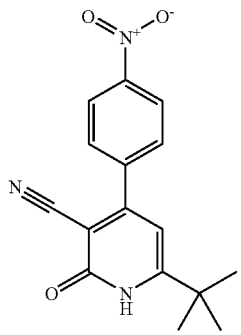

Analogously to Example 1a), 1.55 g of product is obtained from 10 g of ammonium acetate, 1.8 ml of cyanoacetic acid ethyl ester, 2.1 ml of 3,3-dimethyl-2-butanone, and 3 g of 4-nitrobenzaldehyde.

$^1$H-NMR (d6-DMSO): δ=1.33 (9H); 6.30 (1H); 7.93 (2H); 8.38 (2H); 12.46 (1H) ppm.

EXAMPLE 63b

Production of 6-tert-Butyl-3-cyano-4-(4-nitro-phenyl)-2-trifluoromethanesulfonylpyridine

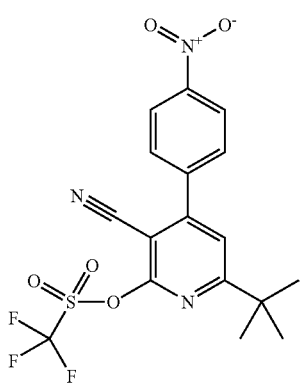

Analogously to Example 3b), 1.85 g of product is obtained from 1.55 g of the substance that is described under Example 63a) and 2.63 ml of trifluoromethanesulfonic acid anhydride in pyridine.

$^1$H-NMR (CDCl$_3$): δ=1.41 (9H); 7.48 (1H); 7.78 (2H); 8.43 (2H) ppm.

EXAMPLE 63c

Production of 6-tert-Butyl-4-(4-nitro-phenyl)-1H-pyrazolo[3,4b]pyridin-3-ylamine

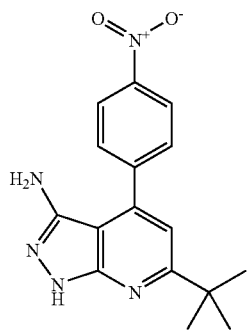

Analogously to Example 1c), 969 mg of product is produced from 1.85 g of the compound, described under Example 63b), with 800 μl of hydrazine hydrate solution (80%) in propanol.

$^1$H-NMR (d6-DMSO): δ=1.39 (9H); 4.58 (2H); 7.87 (2H); 8.38 (2H); 12.30 (1H) ppm.

Biological Testing of the Compounds

Test System for EphB4

A mixture that consists of 20 ng/ml of recombinant EphB4 kinase (related to ProQinase GmbH, Freiburg, Germany), 2.67 μg/ml of polyGluAlaTyr, 2 μmol of ATP, 25 mmol of HEPES (pH 7.3), 5 mmol of MgCl$_2$, 1 mmol of MnCl$_2$, 2 mmol of DTT, 0.1 mmol of NaVO$_4$, 1% (v/v) glycerol, 0.02% NP40, EDTA-free protease inhibitors (Complete Fa. [Company] Roche, 1 tablet in 50 ml) is incubated at 20° C. for 10 minutes. Test substances are dissolved in 100% DMSO and introduced in 0.017× volume before the beginning of the reaction. 60 minutes after the addition of 1.7× volume of a solution of 50 mmol of Hepes, pH 7.0, 0.2% BSA, 0.14 μg/ml of PT66-europium, 3.84 μg/ml of SA-XL665, and 75 mmol of EDTA, the batch is measured in a Discovery HTRF-measuring device of the PerkinElmer Company.

The following compounds, i.a., inhibit the EphB4 kinase with an IC$_{50}$ that is less than 10 μmol: Examples 6, 12, 14, 16, 33, 35, 39, 40, 41, 51, etc. The IC$_{50}$ of compound 6 is, for example, 6.1 μm.

This illustrates that the substances according to the invention inhibit protein tyrosine kinases, in particular Eph receptors, and here in particular EphB4.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2004 061 288.9, filed Dec. 14, 2004, and U.S. Provisional Application Ser. No. 60/636,690, filed Dec. 17, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. Compounds of general formula (I)

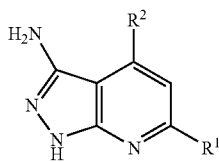

in which
R$^1$ stands for C$_1$-C$_6$-alkyl, C$_2$-C$_6$-alkenyl, C$_2$-C$_6$-alkinyl, C$_3$-C$_{10}$-cycloalkyl, C$_3$-C$_{10}$-heterocycloalkyl, aryl or heteroaryl that optionally is substituted in one or more places, in the same way or differently, with K, wherein the C$_3$-C$_{10}$-heterocycloalkyl and/or the heteroaryl itself is interrupted by at least one of the following atoms nitrogen, oxygen and/or sulfur in the ring, and the C$_3$-C$_{10}$-heterocycloalkyl and/or heteroaryl can be linked only via a carbon ring atom with the pyrazolopyridine, and C$_3$-C$_{10}$-cycloalkyl and/or C$_3$-C$_{10}$-heterocycloalkyl optionally can be interrupted by one or more —(CO)—, —SO— or —SO$_2$— groups that are the same or different in the ring, and optionally one or more double bonds can be contained in the ring, or for a C$_3$-C$_{10}$-cycloalkyl, aryl, C$_3$-C$_{10}$-heterocycloalkyl or heteroaryl that is substituted with the group —O—(CH$_2$)$_n$—O—, wherein the terminal oxygen atoms of the —O—(CH$_2$)$_n$—O— group are linked to the same or a directly adjacent C$_3$-C$_{10}$-cycloalkyl ring-, aryl ring-, C$_3$-C$_{10}$-heterocycloalkyl ring- or heteroaryl ring-carbon atom, K stands for halogen, hydroxy or the group —O—R$^3$, COR$^4$ or —NR$^5$R$^6$, or for C$_3$-C$_{10}$-cycloalkyl, C$_3$-C$_{10}$-heterocycloalkyl, aryl or heteroaryl that optionally is substituted in one or more places, in the same way or differently, with L, wherein the C$_3$-C$_{10}$-heterocycloalkyl and/or the heteroaryl itself is interrupted by at least one of the following atoms nitrogen, oxygen and/or sulfur in the ring, and C$_3$-C$_{10}$-cycloalkyl and/or C$_3$-C$_{10}$-heterocycloalkyl optionally can be interrupted by one or more —(CO)—, —SO— or —SO$_2$— groups that are the same or different in the ring, and optionally one or more double bonds can be contained in the ring, L stands for C$_1$-C$_6$-alkyl or the group —COR$^4$, —OR$^3$, or —NR$^5$R$^6$, R$^2$ stands for C$_3$-C$_{10}$-cycloalkyl, aryl, or heteroaryl that optionally is substituted in one or more places, in the same way or differently, with M, R$^3$ stands for C$_1$-C$_6$-alkyl, aryl or —(CH$_2$)$_n$-aryl that optionally is substituted in one or more places, in the same way or differently, with the group —NR$^5$R$^6$, R$^4$ stands for hydrogen, hydroxy, C$_1$-C$_6$-alkyl or C$_1$-C$_6$-alkoxy, M stands for cyano, halogen, hydroxy, nitro or for C$_1$-C$_6$-alkyl, C$_2$-C$_6$-alkenyl, or C$_2$-C$_6$-alkinyl that optionally is substituted in one or more places, in the same way or differently, with amino, cyano, halogen, hydroxy, nitro, or C$_1$-C$_6$-alkoxy, or for the group —O—R$^3$, —COR$^4$, or —CO—N—R$^7$, R$^5$ and R$^6$, independently of one another, stand for hydrogen, C$_1$-C$_6$-alkyl or for the group —COR$^4$, R$^7$ stands for hydrogen or NH$_2$, and n stands for 1 to 4, with the stipulation that if
R$^1$ stands for methyl, then R$^2$ cannot simultaneously stand for phenyl, chlorophenyl, or benzofuranyl, or furanyl that is substituted with hydroxy and/or methoxy, or if
R$^1$ stands for —CH=CH-phenyl, then R$^2$ cannot simultaneously stand for phenyl, or if
R$^1$ stands for —CH=CH-chlorophenyl, then R$^2$ cannot simultaneously stand for phenyl or chlorophenyl, or if
R$^1$ stands for —CH=CH-methoxyphenyl, then R$^2$ cannot simultaneously stand for phenyl or methoxyphenyl, or if
R$^1$ stands for phenyl, then R$^2$ cannot simultaneously stand for methoxyphenyl or phenyl, or if
R$^1$ stands for chlorophenyl, then R$^2$ cannot simultaneously stand for chlorophenyl, or if
R$^1$ stands for dichlorophenyl, then R$^2$ cannot simultaneously stand for trimethoxyphenyl, or if
R$^1$ stands for bromophenyl, then R$^2$ cannot simultaneously stand for trimethoxyphenyl, or if
R$^1$ stands for alkyl, alkenyl, aryl, aralkyl, cycloalkyl, for a phenyl-substituted alkyl or p-methoxyphenyl, then R$^2$ cannot simultaneously also stand for aryl, a heterocyclic radical or cycloalkyl, or a stereoisomer or salt thereof.

2. A compounds according to claim 1, in which
R$^1$ stands for C$_1$-C$_6$ alkyl, C$_3$-C$_{10}$-cycloalkyl that optionally is substituted in one or more places, in the same way or differently, with K, wherein the C$_3$-C$_{10}$-cycloalkyl optionally is interrupted by one or more —(CO)—, —SO— or —SO$_2$— groups in the ring, and optionally one or more double bonds can be contained in the ring, or for aryl, C$_3$-C$_{10}$-heterocycloalkyl or heteroaryl that optionally is substituted in one or more places, in the same way or differently, with K, wherein the C$_3$-C$_{10}$-heterocycloalkyl and/or the heteroaryl itself is interrupted by at least one nitrogen, oxygen and/or sulfur, and the C$_3$-C$_{10}$-heterocycloalkyl and/or heteroaryl can be linked only via a carbon ring atom to the pyrazolopyridine, or for a C$_3$-C$_{10}$-cycloalkyl, aryl, C$_3$-C$_{10}$-heterocycloalkyl or heteroaryl that is substituted with the group —O—(CH$_2$)$_n$—O—, wherein the terminal oxygen atoms of the —O—(CH$_2$)$_n$—O— group are linked to the same or a directly adjacent C$_3$-C$_{10}$-cycloalkyl ring-, aryl ring-, C$_3$-C$_{10}$-heterocycloalkyl ring- or heteroaryl ring-carbon atom, K stands for halogen, hydroxy or the group —OR$^3$ or —COR$^4$, or for C$_3$-C$_{10}$-cycloalkyl, C$_3$-C$_{10}$-heterocycloalkyl, aryl or heteroaryl that optionally is substituted in one or more places, in the same way or differently, with L, wherein the C$_3$-C$_{10}$-heterocycloalkyl and/or the heteroaryl itself is interrupted by at least one of the following atoms nitrogen, oxygen and/or sulfur in the ring, and C$_3$-C$_{10}$-cycloalkyl and/or C$_3$-C$_{10}$-heterocycloalkyl optionally can be interrupted by one or more —(CO)—, —SO— or —SO$_2$— groups that are the same or different in the ring, and optionally one or more double bonds can be contained in the ring, R$^2$ stands for C$_3$-C$_{10}$-cycloalkyl, aryl or heteroaryl that optionally is substituted in one or more places, in the same way or differently, with M, wherein the heteroaryl is interrupted by at least one nitrogen, oxygen and/or sulfur, $R^3$ stands for $C_1$-$C_6$-alkyl, aryl or —$(CH_2)_n$-aryl, and M stands for amino, cyano, halogen, hydroxy, or nitro or for $C_1$-$C_6$-alkyl that optionally is substituted in one or more places, in the same way or differently, with amino, cyano, halogen, hydroxy, nitro, or $C_1$-$C_6$-alkoxy, or for the group —O—$C_1$-$C_6$-alkyl, —O—$(CH_2)_n$—$NR^5R^6$, —$COR^4$, —O-phenyl, —O—$(CH_2)_n$-phenyl or —CO—N—$R^7$, or a stereoisomer or salt thereof.

3. Compounds according to claim 2, in which $R^1$ stands for $C_1$-$C_6$ alkyl, $C_3$-$C_{10}$-cycloalkyl that optionally is substituted in one or more places, in the same way or differently, with K, wherein the $C_3$-$C_{10}$-cycloalkyl optionally is interrupted by one or more —(CO)—, —SO— or —$SO_2$— groups in the ring, and optionally one or more double bonds can be contained in the ring, or for aryl or heteroaryl that optionally is substituted in one or more places, in the same way or differently, with K, wherein the heteroaryl itself is interrupted by at least one nitrogen, oxygen and/or sulfur, and the heteroaryl can be linked only via a carbon ring atom with the pyrazolopyridine, or for a $C_3$-$C_{10}$-cycloalkyl, aryl or heteroaryl that is substituted with the group —O—$(CH_2)_n$—O—, wherein the terminal oxygen atoms of the —O—$(CH_2)_n$—O— group are linked to the same or a directly adjacent $C_3$-$C_{10}$-cycloalkyl ring-, aryl ring- or heteroaryl ring-carbon atom, K stands for halogen, hydroxy or the group —$OR^3$ or $COR^4$ or for $C_3$-$C_{10}$-cycloalkyl, or $C_3$-$C_{10}$-heterocycloalkyl that optionally is substituted in one or more places, in the same way or differently, with L, wherein the $C_3$-$C_{10}$-heterocycloalkyl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, L stands for $C_1$-$C_6$-alkyl or the group —$COR^4$ or —$OR^3$, $R^3$ stands for $C_1$-$C_6$-alkyl or aryl, and M stands for amino, cyano, halogen, hydroxy, or nitro or for $C_1$-$C_6$-alkyl that optionally is substituted in one or more places, in the same way or differently, with amino, cyano, halogen, hydroxy, nitro, or $C_1$-$C_6$-alkoxy, or for the group —O—$C_1$-$C_6$-alkyl, —O—$(CH_2)_n$—$NR^5R^6$, —CO—$C_1$-$C_6$-alkyl, —O-phenyl, —O—$(CH_2)_n$-phenyl or —CO—N—$R^7$, or a stereoisomer or salt thereof.

4. Compounds according to claim 3, in which $R^1$ stands for $C_1$-$C_6$ alkyl, $C_3$-$C_{10}$-cycloalkyl that optionally is substituted in one or more places, in the same way or differently, with K, wherein the $C_3$-$C_{10}$-cycloalkyl optionally is interrupted by one or more —(CO)— groups in the ring, or for aryl or heteroaryl that optionally is substituted in one or more places, in the same way or differently, with K, wherein the heteroaryl itself is interrupted by at least one nitrogen, and the heteroaryl can be linked only via a carbon ring atom with the pyrazolopyridine, or for a $C_3$-$C_{10}$-cycloalkyl, aryl or heteroaryl that is substituted with the group —O—$(CH_2)_n$—O—, wherein the terminal oxygen atoms of the —O—$(CH_2)_n$—O— group are linked to the same or a directly adjacent $C_3$-$C_{10}$-cycloalkyl ring-, aryl ring- or heteroaryl ring-carbon atom, K stands for halogen, hydroxy or for the group —$OR^3$, or $C_3$-$C_{10}$-heterocycloalkyl that optionally is substituted in one or more places, in the same way or differently, with L, wherein the $C_3$-$C_{10}$-heterocycloalkyl itself is interrupted by at least one of the following atoms nitrogen and/or oxygen in the ring, L stands for $C_1$-$C_6$-alkyl or —COO—$C_1$-$C_6$-alkyl, $R^2$ stands for $C_3$-$C_6$-cycloalkyl, aryl or heteroaryl that optionally is substituted in one or more places, in the same way or differently, with M, wherein the heteroaryl is interrupted by at least one nitrogen, and M stands for amino, cyano, halogen, hydroxy, or nitro or for $C_1$-$C_6$-alkyl that optionally is substituted in one or more places, in the same way or differently, with amino, cyano, halogen, hydroxy, nitro or $C_1$-$C_6$-alkoxy or for the group —O—$C_1$-$C_6$-alkyl, —O—$(CH_2)_n$—$N(C_1$-$C_6$-alkyl$)_2$, —CO—$C_1$-$C_6$-alkyl, phenoxy, benzyloxy or —CO—N—$NH_2$, or a stereoisomer or salt thereof.

5. Compounds according to claim 1, in which

M stands for amino, cyano, halogen, hydroxy, nitro or for $C_1$-$C_6$-alkyl that optionally is substituted in one or more places, in the same way or differently, with amino, cyano, halogen, hydroxy, nitro or $C_1$-$C_6$-alkoxy, or for the group —O—$C_1$-$C_6$-alkyl, —O—$(CH_2)_n$—$N(C_1$-$C_6$-alkyl$)_2$ or —CO—$C_1$-$C_6$-alkyl, or a stereoisomer or salt thereof.

6. Compounds according to claim 4, in which $R^1$ stands for $C_1$-$C_6$-alkyl, $C_3$-$C_6$-cycloalkyl, cyclohexanone, 1,4-dioxa-spiro[4.5]dec-8-yl, phenyl, 1,3-benzodioxolyl or pyridinyl that optionally is substituted in one or more places, in the same way or differently, with K, K stands for halogen, hydroxy, $C_1$-$C_6$-alkoxy or morpholinyl, piperazinyl, piperidinyl, or phenoxy that optionally is substituted in one or more places, in the same way or differently, with L, $R^2$ stands for phenyl or quinolinyl, imidazolyl, indolyl or pyridinyl that optionally is substituted in one or more places, in the same way or differently, with M, and M stands for amino, cyano, halogen, hydroxy, nitro, $C_1$-$C_6$-alkyl, —$CF_3$, or for $C_1$-$C_3$-alkoxy or for the group —CO—$C_1$-$C_6$-alkyl, —O—$(CH_2)_n$—$N(C_1$-$C_6$-alkyl$)_2$, phenoxy or benzyloxy, or a stereoisomer or salt thereof.

7. Compounds according to claim 6, in which $R^1$ stands for $C_3$-$C_6$ alkyl, cyclopropyl, cyclohexyl, cyclohexanone, 1,4-dioxa-spiro[4.5]dec-8-yl, phenyl, 1,3-benzodioxolyl or pyridinyl that optionally is substituted in one or more places, in the same way or differently, with K, K stands for halogen, hydroxy, methoxy or morpholinyl, piperazinyl, piperidinyl or phenoxy that optionally is substituted in one or more places, in the same way or differently, with L, L stands for $C_1$-$C_3$-alkyl or —COO—$C_3$-$C_5$-alkyl, $R^2$ stands for phenyl, quinolinyl, imidazolyl, indolyl or pyridinyl that optionally is substituted in one or more places, in the same way or differently, with M, and M stands for cyano, halogen, hydroxy, nitro, methyl, —$CF_3$ or for methoxy, or for the group —CO—$C_1$-$C_3$-alkyl, or —O—$(CH_2)_3$—N(methyl)$_2$ or a stereoisomer or salt thereof.

8. Compounds according to claim 7, in which $R^1$ stands for tert-butyl, cyclopropyl, cyclohexyl, cyclohexanone, 1,4-dioxa-spiro[4.5]dec-8-yl, phenyl, 1,3- benzodioxolyl or pyridinyl that optionally is substituted in one or more places, in the same way or differently, with K, L stands for methyl or —COO-tert-butyl, $R^2$ stands for phenyl, quinolinyl, imidazolyl, indolyl or pyridinyl that optionally is substituted in one or more places, in the same way or differently, with M, and M stands for cyano, halogen, hydroxy, nitro, methyl, —$CF_3$ or for methoxy or for the group —CO-methyl or —O—$(CH_2)_3$—N(methyl)$_2$, or a stereoisomer or salt thereof.

9. A method for preparing a compound of claim 1, comprising converting a compound of formula (II) to a compound of formula (III)

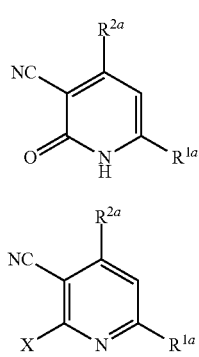

wherein

X stands for halogen or —O—$SO_2$—$C_mF_{2m+1}$, m stands for 1 to 4, $R^{1a}$ and $R^{2a}$ have the same meaning as $R^1$ and $R^2$ according to claim 1, wherein K, however, also can stand for the group —$COR^4$, and $R^3$ also can stand for the group trimethylsilyl (TMS), tert-butyl-dimethylsilyl (TBDMS), tert-butyl-diphenylsilyl (TBDPS), triethylsilyl (TES), $C_1$-$C_2$-alkyl, $C_3$-$C_6$-allyl, benzyl or for the group —$COR^{4a}$, and $R^{4a}$ stands for hydrogen, $C_1$-$C_6$-alkyl or $C_1$-$C_6$-alkoxy.

10. A Pharmaceutical composition comprising a pharmaceutically acceptable carrier and at least one compound of formula I

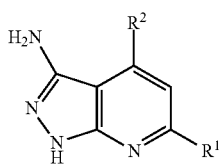

in which $R^1$ stands for $C_1$-$C_6$-alkyl, $C_2$-$C_6$-alkenyl, $c_2$-$C_6$-alkinyl, $C_3$-$C_{10}$-cycloalkyl, $C_3$-$C_{10}$-heterocycloalkyl, aryl or heteroaryl that optionally is substituted in one Or more places, in the same way or differently, with K, wherein the $C_3$-$C_{10}$-heterocycloalkyl and/or the heteroaryl itself is interrupted by at least one of the following atoms nitrogen, oxygen and/or sulfur in the ring, and the $C_3$-$C_{10}$-heterocycloalkyl and/or heteroaryl can be linked only via a carbon ring atom with the pyrazolopyridine, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, or for a $C_3$-$C_{10}$-cycloalkyl, aryl, $C_3$-$C_{10}$-heterocycloalkyl or heteroaryl that is substituted with the group —O—$(CH_2)_n$—O—, wherein the terminal oxygen atoms of the —O—$(CH_2)_n$—O— group are linked to the same or a directly adjacent $C_3$-$C_{10}$-cycloalkyl ring-, aryl ring-, $C_3$-C10-heterocycloalky ring- or heteroaryl ring-carbon atom, K stands for halogen, hydroxy or the group —O—$R^3$, $COR^4$ or -$NR^5R^6$, or for $C_3$-$C_{10}$-cycloalkyl, $C_3$-$C_{10}$-heterocycloalkyl, aryl or heteroaryl that optionally is substituted in one or more places, in the same way or differently, with L, wherein the $C_3$-$C_{10}$-heterocycloalkyl and/or the heteroaryl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —$SO_2$— groups that are the same or different in the ring, and optionally one or more double bonds can be contained in the ring, L stands for $C_1$-$C_6$-alkyl or the group —$COR^4$, —$OR^3$, or —$NR^5R^6$, $R^2$ stands for $C_3$-$C_{10}$-cycloalkyl, aryl, or heteroaryl that optionally is substituted in one or more places, in the same way or differently, with M, $R^3$ stands for $C_1$-$C_6$-alkyl, aryl or —$(CH_2)_n$-aryl that optionally is substituted in one or more places, in the same way or differently, with the group —$NR^5R^6$, $R^4$ stands for hydrogen, hydroxy, $C_1$-$C_6$-alkyl or $C_1$-$C_6$-alkoxy, M stands for cyano, halogen, hydroxy, nitro or for $C_1$-$C_6$-alkyl, $C_2$-$C_6$-alkenyl, or $C_2$-$C_6$-alkinyl that optionally is substituted in one or more places, in the same way or differently, with amino, cyano, halogen, hydroxy, nitro, or $C_1$-C6-alkoxy, or for the group —O—$R^3$, —$COR^4$, or —CO—N—$R^7$, $R^5$ and $R^6$, independently of one another, stand for hydrogen, $C_1$-$C_6$-alkyl or for the group —$COR^4$, $R^7$ stands for hydrogen or $NH_2$, and n stands for 1 to 4, with the stipulation that if $R^1$ stands for methyl, then $R^2$ cannot simultaneously stand for phenyl, chlorophenyl, or benzofuranyl, or furanyl that is substituted with hydroxy and/or methoxy, or if $R^1$ stands for —CH=CH-phenyl, then $R^2$ cannot simultaneously stand for phenyl, or if $R^1$ stands for —CH=CH-chlorophenyl, then $R^2$ cannot simultaneously stand for phenyl or chlorophenyl, or if $R^1$ stands for —CH=CH-methoxyphenyl, then $R^2$ cannot simultaneously stand for phenyl or methoxyphenyl, or if $R^1$ stands for phenyl, then $R^2$ cannot simultaneously stand for methoxyphenyl or phenyl, or if $R^1$ stands for chlorophenyl, then $R^2$ cannot simultaneously stand for chlorophenyl, or if $R^1$ stands for dichlorophenyl, then $R^2$ cannot simultaneously stand for trimethoxyphenyl, or if $R^1$ stands for bromophenyl, then $R^2$ cannot simultaneously stand for trimethoxyphenyl, or if $R^1$ stands for alkyl, alkenyl, aryl, aralkyl, cycloalkyl, for a phenyl-substituted alkyl or p-methoxyphenyl, then $R^2$ cannot simultaneously also stand for aryl, a heterocyclic radical or cycloalkyl, with the overriding stipulation that if $R^1$ stands for alkyl, alkenyl, aryl, aralkyl, or cycloalkyl, or for a phenyl-substituted alkyl or p-methoxyphenyl, then R² can also simultaneously stand for alkyl, alkenyl, aryl, aralkyl, cyano, a heterocyclic radical or cycloalkyl, R¹ stands for a lower alkyl radical, alkoxy, or a primary, secondary or tertiary amino group, then R² can also simultaneously stand for a lower alkyl radical.

11. A pharmaceutical composition comprising a compound according to claim 1 and a pharmaceutically acceptable carrier.

12. A pharmaceutically acceptable salt of a compound of formula (I)

(I)

$H_2N$ $R^2$

[structure of 1H-pyrazolo[3,4-b]pyridine with NH₂ at 3-position, R² at 4-position, R¹ at 6-position]

in which
R¹ stands for $C_1$-$C_6$-alkyl, $C_2$-$C_6$-alkenyl, $C_2$-$C_6$-alkinyl, $C_3$-$C_{10}$-cycloalkyl, $C_3$-$C_{10}$-heterocycloalkyl, aryl or heteroaryl that optionally is substituted in one or more places, in the same way or differently, with K, wherein the $C_3$-$C_{10}$-heterocycloalkyl and/or the heteroaryl itself is interrupted by at least one of the following atoms nitrogen, oxygen and/or sulfur in the ring, and the $C_3$-$C_{10}$-heterocycloalkyl and/or heteroaryl can be linked only via a carbon ring atom with the pyrazolopyridine, and $C_3$-$C_{10}$-cycloalkyl and/or $C_3$-$C_{10}$-heterocycloalkyl optionally can be interrupted by one or more —(CO)—, —SO— or —SO₂— groups that are the same or different in the ring, and optionally one or more double bonds can be contained in the ring, or for a $C_3$-$C_{10}$-cycloalkyl, aryl, $C_3$-$C_{10}$-heterocycloalkyl or heteroaryl that is substituted with the group —O—$(CH_2)_n$—O—, wherein the terminal oxygen atoms of the —O—$(CH_2)_n$—O— group are linked to the same or a directly adjacent $C_3$-$C_{10}$-cycloalkyl ring-, aryl ring-, $C_3$-$C_{10}$-heterocycloalky ring- or heteroaryl ring-carbon atom, K stands for halogen, hydroxy or the group —O—$R^3$, $COR^4$ or —$NR^5R^6$, or for $C_3$-$C_{10}$-cycloalkyl, $C_3$-$C_{10}$-heterocycloalkyl, aryl or heteroaryl that optionally is substituted in one or more places, in the same way or differently, with L, wherein the $C_3$-$C_{10}$-heterocycloalkyl and/or the heteroaryl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —SO₂— groups that are the same or different in the ring, and optionally one or more double bonds can be contained in the ring, L stands for $C_1$-$C_6$-alkyl or the group —$COR^4$, —$OR^3$, or —$NR^5R^6$, R² stands for $C_3$-$C_{10}$-cycloalkyl, aryl, or heteroaryl that optionally is substituted in one or more places, in the same way or differently, with M, R³ stands for $C_1$-$C_6$-alkyl, aryl or -$(CH_2)_n$-aryl that optionally is substituted in one or more places, in the same way or differently, with the group —$NR^5R^6$, R⁴ stands for hydrogen, hydroxy, $C_1$-$C_6$-alkyl or $C_1$-$C_6$-alkoxy, M stands for cyano, halogen, hydroxy, nitro or for $C_1$-$C_6$-alkyl, $C_2$-$C_6$-alkenyl, or $C_2$-$C_6$-alkinyl that optionally is substituted in one or more places, in the same way or differently, with amino, cyano, halogen, hydroxy, nitro, or $C_1$-C6-alkoxy, or for the group —O—$R^3$, —$COR^4$, or —CO——$R^7$, R⁵ and R⁶, independently of one another, stand for hydrogen, $C_1$-$C_6$-alkyl or for the group —$COR^4$, R⁷ stands for hydrogen or $NH_2$, and n stands for 1 to 4, with the stipulation that if
R¹ stands for methyl, then R² cannot simultaneously stand for phenyl, chlorophenyl, or benzofuranyl, or furanyl that is substituted with hydroxy and/or methoxy, or if
R¹ stands for —CH=CH-phenyl, then R² cannot simultaneously stand for phenyl, or if
R¹ stands for —CH=CH-chlorophenyl, then R² cannot simultaneously stand for phenyl or chlorophenyl, or if
R¹ stands for —CH=CH-methoxyphenyl, then R² cannot simultaneously stand for phenyl or methoxyphenyl, or if
R¹ stands for phenyl, then R² cannot simultaneously stand for methoxyphenyl or phenyl, or if
R¹ stands for chlorophenyl, then R² cannot simultaneously stand for chlorophenyl, or if
R¹ stands for dichlorophenyl, then R² cannot simultaneously stand for trimethoxyphenyl, or if
R¹ stands for bromophenyl, then R² cannot simultaneously stand for trimethoxyphenyl, or if
R¹ stands for alkyl, alkenyl, aryl, aralkyl, cycloalkyl, for a phenyl-substituted alkyl or p-methoxyphenyl, then R² cannot simultaneously also stand for.

13. A compound selected from the group consisting of 6-tert-Butyl-4-p-tolyl-1H-pyrazolo[3,4b]pyridin-3-ylamine 6-tert-Butyl-4-(1H-indol-3-yl)-1H-pyrazolo[3,4b]pyridin-3-ylarnine 6-tert-Butyl-4-(1H-indol-3-yl)-1H-pyrazolo[3,4b]pyridin-3-ylamine 6-tert-Butyl-4-(4-phenoxyphenyl)-1H-pyrazolo[3,4-pyridin-3-ylamine 6-tert-Butyl-4-(4-benzyloxyphenyl)-1H-pyrazolo[3,4]pyridin-3-ylamine 6-tert-Butyl-4-(3-methoxyphenyl)-1H-pyrazolo[3,4b]-pyridin-3-ylamine 6-tert-Butyl-4-(3-cyanophenyl)-1H-pyrazolo[3,4b]-pyridin-3-ylamine 1-[4-(3-Amino-6-tert-butyl-1H-pyrazolo[3,4b]pyridin-4-yl)-phenyl]-ethanone 1-[3-(3-Amino-6-tert-butyl-1H-pyrazolo[3,4b]pyridin-4-yl)-phenyl]-ethanone 6-Cyclohexyl-4-p-tolyl-1H-pyrazolo[3,4b]pyridin-3-ylamine 6-(1,4-Dioxa-spiro[4.5]dec-8-yl)-4-p-tolyl-1H-pyrazolo[3,4b]pyridin-3-ylamine 4-(3-Amino-4-p-tolyl-1H-pyrazolo[3,4b]pyridin-6-yl)-cyclohexanone 4-[4-(3-Amino-4-p-tolyl-1H-pyrazolo[3,4b]pyridin-6-yl)-cyclohexyl]-piperazine-1-carboxylic acid tert-butyl ester 6-(4-Piperazin-1-yl-cyclohexyl)-4-p-tolyl-1-pyrazolo[3,4b]pyridin-3-ylamine 6-[4-(4-Methyl-piperazin-1-yl)-cyclohexyl]-4-p-tolyl-1H-pyrazolo[3,4b]pyridin-3-ylamine 6-(4-Piperidin-1-yl-cyclohexyl)-4-p-tolyl-1H-pyrazolo[3,4b]pyridin-3-ylarnine 6-(4-Morpholin-4-yl-cyclohexyl)-4-p-tolyl-1H-pyrazolo[3,4b]ppidin-3-ylamine 6-(1,4-Dioxa-spiro[4.5]dec-8-yl)-4-(4-phenoxyphenyl)-1H-pyrazolo[3,4]pyridin-3-ylamine 4-[3-Amino-4-(4-phenoxy-phenyl)-1H-pyrazolo[3,4b]-pyridin-6-yl]-cyclohexanone 4-{4-[3-Amino-4-(4-phenoxy-phenyl)-1H-pyrazolo[3,4b]pyridin-6-yl]-cyclohexyl}-piperazine-1-carboxylic acid tert-butyl ester 4-(4-Phenoxyphenyl)-6-(4-piperazin-1-yl-cyclohexyl)-1H-pyrazolo[3,4b]pyridin-3-ylarnine 6-[4-(4-Methyl-piperazin-1-yl)-cyclohexyl]-4-(4-phenoxyphenyl)-1H-pyrazolo[3,4b]pyridin -3-ylamine 4-(4-Phenoxy-phenyl)-6-(4-piperidin-1-yl-cyclohexyl)-1H-pyrazolo[3,4b]pyridin-3-ylamine 6-(4-Morpholin-4-yl-cyclohexyl)-4-(4-phenoxyphenyl)-1H-pyrazolo[3,4b]pyridin-3-ylamine 6-(1,1-Dimethyl-2-piperidin-1-yl-ethyl)-4-p-tolyl-1H-pyrazolo[3,4b]pyridin-3-ylamine 6-(1,1-Dimethyl-2-morpholin-1-yl-ethyl)-4-p-tolyl-1H-pyrazolo[3,4b]pyridin-3-ylamine 6[1,1-Dimethyl-2-(4- methyl-piperazin-1-yl)-ethyl]4-p-tolyl-1H-pyrazolo[3,4b]pyridin-3-ylamine 4[2-(3-Amino-4-p-tolyl-1H-pyrazolo[3,4b]pyridin-6-yl)-2-methyl-propyl]-piperazine-1-carboxylic acid tert-butyl ester 6-(1,1-Dimethyl-2-piperazin-1-yl-ethyl)-4-p-tolyl-1H-pyrazolo[3,4b]pyridin-3-ylamine 6-(1,1-Dimethyl-2-(4-methyl-piperazin-1-yl)-ethyl]-4-(4-phenoxyphenyl)-1H-pyrazolo [3,4b]pyridin-3-ylamine 6-(1,1-Dimethyl-2-morpholin-4-yl-ethyl)-4-(4-phenoxyphenyl)]-1H-pyrazolo[3,4b]pyridin-3-ylamine 3 -(3-Amino-6-pyridin-4-yl-1H-pyrazolo[3,4-b]pyridin-4-yl)-phenol 3 -(3-Amino-6-pyridin-4-yl-1H-pyrazolo[3,4-b]pyridin-4-yl)-5-methoxyphenol 4-(3,5-Dimethoxy-phenyl)-6-pyridin-4-yl-1H-pyrazolo[3,4-b]pyridin-3-ylamine 3 -(3-Amino-6-pyridin-4-yl-1H-pyrazolo[3,4-b]pyridin-4-yl)-4-methyl-phenol 3-(3-Amino-6-tert-butyl-1H-pyrazolo[3,4-b]pyridin-4-yl)-5-methoxy-phenol 3-(3-Amino-6-tert-butyl-1H-pyrazolo[3,4-b]pyridin-4-yl)-phenol 3-(3-Amino-6-tert-butyl-1H-pyrazolo[3,4-b]pyridin-4-yl)-4-methyl-phenol 4-(3,5 -Dimethoxy-phenyl)-6-pyridin-4-yl-1H-pyrazolo[3,4-b]pyridin-3-ylamine 3-(3-Amino-6-tert-butyl-1 H-pyrazolo[3,4-b]pyridin-4-yl)-5-isopropoxy Phenol 3-(3-Amino-6-tert-butyl-1H-pyrazolo[3,4b]pyridin-4-yl)-4-nitro-phenol 5-(3 -Amino-6-tert-butyl- 1H-pyrazolo[3,4-b]pyridin-4-yl)-2,3dimethoxyphenol 6-Cyclopropyl-4-(3,4-dichlorophenyl)-1H-pyrazolo-[3,4-b]pyridin-3-ylamine 3-(3-Amino-6-cyclopropyl-1H-pyrazolo-[3,4-b]pyridin-4-yl)-phenol 3-(3-Amino-6-cyclohexyl-1H-pyrazolo-[3,4-b]pyridin-4-yl)-phenol 5-(3-Amino-6-tert-butyl-1H-pyrazolo[3,4-b]pyridin-4-yl)-2-methoxyphenol 5-(3-Amino-6-tert-butyl-1 H-pyrazolo[3,4-b]pyridin-4-yl)-benzene-1,3-diol 4-Isopropyl -6-(3,4-methylenedioxyphenyl)-1H-pyrazolo[3,4b]pyridin-3-ylamine 6-(3-Hydroxyphenyl)-4-(4-pyridyl)-1H-pyrazolo[3,4b]-pyridin-3-ylamine 4-(4-Chlorophenyl)-6-phenyl-1 H-pyrazolo[3,4-b]pyridin-3-ylamine 6-Cyclopropyl-4-(3,4-diehlorophenyl)-1H-pyrazolo[3,4-b]pyridin-3-ylamine 5-[3-Amino-6-(4-fluorophenyl)-1H-pyrazolo [3,4-b]pyridin-4-yl]-2-methoxyphenol 6-Pyridin-3-yl-4-quinolin-3-yl-1H-pyrazolo[3,4-b]pyridin-3-ylamine 6-(3-Chlorophenyl)-4-(1H-indol-3-yl)-1H-pyrazolo[3,4-b]pyridin-3-ylamine 4-[3-Amino-6-(3-methoxyphenyl)-1H-pyrazolo[3,4-b]pyridin-4-yl]-benzonitrile 4-(4-Chlorophenyl)-6-cyclopropyl-1H-pyrazolo[3,4-b]pyridin-3-ylamine 6-Cyclopropyl-4-(3-nitrophenyl)-1H-pyrazolo[3,4-b]pyridin-3-ylamine 6-(4-Morpholin-4-yl-phenyl)-4-pyridin-4-yl-1H-pyrazolo[3,4-b]pyridin-3-ylamine 4-[4-(3-Dimethylaminopropoxy)phenyl] 6-(4-fluorophenyl)-1H -pyrazolo[3,4-b]pyridin-3-ylamine 6-Cyclopropyl-4-(4-trifluoromethylphenyl-1H-pyrazolo[3,4-b]pyridin-3-ylamine 4-(3-Amino-6-cyclopropyl-1H-pyrazolo[3,4-b]pyridin-4-yl)-benzonitrile 4-(1H-Imidazol-2-yl)-6-(4-phenoxy-phenyl)-1H-pyrazolo[3,4-b]pyridin-3-ylamine and 6-tert-Butyl-4-(4-nitro-phenyl)-1H-pyrazolo[3,4b]pyridin-3-ylamine and pharmaceutically acceptable salts thereof.

14. A pharmaceutical composition comprising a pharmaceutically acceptable carrier and at least one compound of formula I

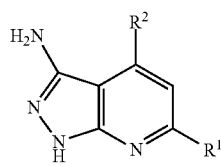

(I)

in which
$R^1$ stands for $C_1$-$C_6$-alkyl, $C_2$-$C_6$-alkenyl, $C_2$-$C_6$-alkinyl, $C_3$-$C_{10}$-cycloalkyl, $C_3$-$C_{10}$-heterocycloalkyl, aryl or heteroaryl that optionally is substituted in one or more places, in the same way or differently, with K, wherein the $C_3$-$C_{10}$-heterocycloalkyl and/or the heteroaryl itself is interrupted by at least one of the following atoms nitrogen, oxygen and/or sulfur in the ring, and the $C_3$-$C_{10}$-heterocycloalkyl and/or heteroaryl can be linked only via a carbon ring atom with the pyrazolopyridine, and $C_3$-$C_{10}$-cycloalkyl and/or $C_3$-$C_{10}$-heterocycloalkyl optionally can be interrupted by one or more —(CO)—, —SO— or —SO$_2$— groups that are the same or different in the ring, and optionally one or more double bonds can be contained in the ring, or for a $C_3$-$C_{10}$-cycloalkyl, aryl, $C_3$-$C_{10}$-heterocycloalkyl or heteroaryl that is substituted with the group —O—(CH$_2$)$_n$—O—, wherein the terminal oxygen atoms of the —O—(CH$_2$)$_n$—O— group are linked to the same or a directly adjacent $C_3$-$C_{10}$-cycloalkyl ring-, aryl ring-, $C_3$-$C_{10}$-heterocycloalky ring- or heteroaryl ring-carbon atom,
K stands for halogen, hydroxy or the group —O—$R^3$, or COR$^4$, or for $C_3$-$C_{10}$-cycloalkyl, $C_3$-$C_{10}$-heterocycloalkyl, aryl or heteroaryl that optionally is substituted in one or more places, in the same way or differently, with L, wherein the $C_3$-$C_{10}$-heterocycloalkyl and/or the heteroaryl itself is interrupted by at least one of the following atoms nitrogen, oxygen and/or sulfur in the ring, and $C_3$-$C_{10}$-cycloalkyl and/or $C_3$-$C_{10}$-heterocycloalkyl optionally can be interrupted by one or more —(CO)—, —SO— or —SO$_2$— groups that are the same or different in the ring, and optionally one or more double bonds can be contained in the ring,
L stands for $C_1$-$C_6$-alkyl or the group —COR$^4$, —OR$^3$, or —NR$^5$R$^6$,
$R^2$ stands for $C_1$-$C_6$-alkyl, $C_3$-$C_{10}$-cycloalkyl, aryl, or heteroaryl that optionally is substituted in one or more places, in the same way or differently, with M,
$R^3$ stands for $C_1$-$C_6$-alkyl, aryl or —(CH$_2$)$_n$-aryl that optionally is substituted in one or more places, in the same way or differently, with the group —NR$^5$R$^6$,
$R^4$ stands for hydrogen, hydroxy, $C_1$-$C_6$-alkyl or $C_1$-$C_6$-alkoxy,
M stands for cyano, halogen, hydroxy, nitro or for $C_1$-$C_6$-alkyl, $C_2$-$C_6$-alkenyl, or $C_2$-$C_6$-alkinyl that optionally is substituted in one or more places, in the same way or differently, with amino, cyano, halogen, hydroxy, nitro, or $C_1$-$C_6$-alkoxy, or for the group —O-$R^3$, —COR$^4$, or —CO—N—$R^7$,
$R^5$ and $R^6$, independently of one another, stand for hydrogen, $C_1$-$C_6$-alkyl or for the group —COR$^4$,
$R^7$ stands for hydrogen or NH$_2$, and n stands for 1 to 4,
with the stipulation that if
$R^1$ stands for methyl, then $R^2$ cannot simultaneously stand for methyl, —CH$_2$—O—CH$_3$, phenyl, chlorophenyl, or benzofuranyl, —CF$_3$, or furanyl that is substituted with hydroxy and/or methoxy, or if
$R^1$ stands for —CH$_2$—O—CH$_3$, then $R^2$ cannot simultaneously stand for methyl, or if
$R^1$ stands for —CH═CH-phenyl, then $R^2$ cannot simultaneously stand for phenyl, or if
$R^1$ stands for —CH═CH-chlorophenyl, then $R^2$ cannot simultaneously stand for phenyl or chlorophenyl, or if
$R^1$ stands for —CH═CH-methoxyphenyl, then $R^2$ cannot simultaneously stand for phenyl or methoxyphenyl, or if
$R^1$ stands for phenyl, then $R^2$ cannot simultaneously stand for —CF$_3$, methyl, methoxyphenyl or phenyl, or if R¹ stands for methoxyphenyl, then R² cannot simultaneously stand for —CF₃, or if
R¹ stands for methylphenyl, then R² cannot simultaneously stand for —CF₃, or if
R¹ stands for chlorophenyl, then R² cannot simultaneously stand for chlorophenyl or —CF₃, or if
R¹ stands for dichlorophenyl, then R² cannot simultaneously stand for trimethoxyphenyl, or if
R¹ stands for bromophenyl, then R² cannot simultaneously stand for trimethoxyphenyl, or if
R¹ stands for alkyl, alkenyl, aryl, aralkyl, cycloalkyl, for a phenyl-substituted alkyl or p-methoxyphenyl, then R² cannot simultaneously also stand for alkyl, alkenyl, aryl, a heterocyclic radical or cycloalkyl, or if
R¹ stands for a lower alkyl radical, alkoxy, or aryloxy, then R² cannot simultaneously stand for a lower alkyl radical,
with the overriding stipulation that if
R¹ stands for alkyl, alkenyl, aryl, aralkyl, or cycloalkyl, or for a phenyl-substituted alkyl or p-methoxyphenyl, then R² can also simultaneously stand for alkyl, alkenyl, aryl, aralkyl, cyano, a heterocyclic radical or cycloalkyl,
R¹ stands for a lower alkyl radical, alkoxy, or a primary, secondary or tertiary amino group, then R² can also simultaneously stand for a lower alkyl radical.

15. A pharmaceutical composition comprising a pharmaceutically acceptable carrier and at least one compound of formula I

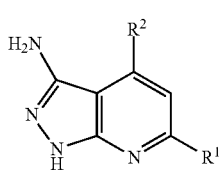

(I)

in which
R¹ stands for C₁-C₆-alkyl, C₂-C₆-alkenyl, C₂-C₆-alkinyl, C₃-C₁₀-cycloalkyl, C₃-C₁₀-heterocycloalkyl, or aryl that optionally is substituted in one or more places, in the same way or differently, with K, wherein the C₃-C₁₀-heterocycloalkyl and/or the heteroaryl itself is interrupted by at least one of the following atoms nitrogen, oxygen and/or sulfur in the ring, and the C₃-C₁₀-heterocycloalkyl and/or heteroaryl can be linked only via a carbon ring atom with the pyrazolopyridine, and C₃-C₁₀-cycloalkyl and/or C₃-C₁₀-heterocycloalkyl optionally can be interrupted by one or more —(CO)—, —SO— or —SO₂— groups that are the same or different in the ring, and optionally one or more double bonds can be contained in the ring, or for a C₃-C₁₀-cycloalkyl, aryl, C₃-C₁₀-heterocycloalkyl or heteroaryl that is substituted with the group —O—(CH₂)ₙ—O—, wherein the terminal oxygen atoms of the —O—(CH₂)ₙ—O— group are linked to the same or a directly adjacent C₃-C₁₀-cycloalkyl ring-, aryl ring-, C₃-C₁₀-heterocycloalky ring- or heteroaryl ring-carbon atom,
K stands for halogen, hydroxy or the group —O—R³, COR⁴ or —NR⁵R⁶, or for C₃-C₁₀-cycloalkyl, C₃-C₁₀-heterocycloalkyl, aryl or heteroaryl that optionally is substituted in one or more places, in the same way or differently, with L, wherein the C₃-C₁₀-heterocycloalkyl and/or the heteroaryl itself is interrupted by at least one of the following atoms nitrogen, oxygen and/or sulfur in the ring, and C₃-C₁₀-cycloalkyl and/or C₃-C₁₀-heterocycloalkyl optionally can be interrupted by one or more —(CO)—, —SO— or —SO₂— groups that are the same or different in the ring, and optionally one or more double bonds can be contained in the ring,
L stands for C₁-C₆-alkyl or the group —COR⁴, —OR³, or —NR⁵R⁶,
R² stands for C₁-C₆-alkyl, C₃-C₁₀-cycloalkyl, aryl, or heteroaryl that optionally is substituted in one or more places, in the same way or differently, with M,
R³ stands for C₁-C₆-alkyl, aryl or —(CH₂)ₙ-aryl that optionally is substituted in one or more places, in the same way or differently, with the group —NR⁵R⁶,
R⁴ stands for hydrogen, hydroxy, C₁-C₆-alkyl or C₁-C₆-alkoxy,
M stands for cyano, halogen, hydroxy, nitro or for C₁-C₆-alkyl, C₂-C₆-alkenyl, or C₂-C₆-alkinyl that optionally is substituted in one or more places, in the same way or differently, with amino, cyano, halogen, hydroxy, nitro, or C₁-C₆-alkoxy, or for the group —O—R³, —COR⁴, or —CO—N—R⁷,
R⁵ and R⁶, independently of one another, stand for hydrogen, C₁-C₆-alkyl or for the group —COR⁴,
R⁷ stands for hydrogen or NH₂, and
n stands for 1 to 4,
with the stipulation that if
R¹ stands for methyl, then R² cannot simultaneously stand for methyl, —CH₂—O—CH₃, phenyl, chlorophenyl, or benzofuranyl, —CF₃, or furanyl that is substituted with hydroxy and/or methoxy, or if
R¹ stands for —CH₂—O—CH₃, then R² cannot simultaneously stand for methyl, or if
R¹ stands for —CH═CH-phenyl, then R² cannot simultaneously stand for phenyl, or if
R¹ stands for —CH═CH-chlorophenyl, then R² cannot simultaneously stand for phenyl or chlorophenyl, or if
R¹ stands for —CH═CH-methoxyphenyl, then R² cannot simultaneously stand for phenyl or methoxyphenyl, or if
R¹ stands for phenyl, then R² cannot simultaneously stand for —CF₃, methyl, methoxyphenyl or phenyl, or if
R¹ stands for methoxyphenyl, then R² cannot simultaneously stand for —CF₃, or if
R¹ stands for methylphenyl, then R² cannot simultaneously stand for —CF₃, or if
R¹ stands for chlorophenyl, then R² cannot simultaneously stand for chlorophenyl or —CF₃, or if
R¹ stands for dichlorophenyl, then R² cannot simultaneously stand for trimethoxyphenyl, or if
R¹ stands for bromophenyl, then R² cannot simultaneously stand for trimethoxyphenyl, or if
R¹ stands for alkyl, alkenyl, aryl, aralkyl, cycloalkyl, for a phenyl-substituted alkyl or p-methoxyphenyl, then R² cannot simultaneously also stand for alkyl, alkenyl, aryl, a heterocyclic radical or cycloalkyl, or if
R¹ stands for a lower alkyl radical, alkoxy, or aryloxy, then R² cannot simultaneously stand for a lower alkyl radical,
with the overriding stipulation that if
R¹ stands for alkyl, alkenyl, aryl, aralkyl, or cycloalkyl, or for a phenyl-substituted alkyl or p-methoxyphenyl, then R² can also simultaneously stand for alkyl, alkenyl, aryl, aralkyl, cyano, a heterocyclic radical or cycloalkyl,
R¹ stands for a lower alkyl radical, alkoxy, or a primary, secondary or tertiary amino group, then R² can also simultaneously stand for a lower alkyl radical.

* * * * *

UNITED STATES PATENT AND TRADEMARK OFFICE
CERTIFICATE OF CORRECTION

PATENT NO.      : 7,977,325 B2
APPLICATION NO. : 11/302307
DATED           : July 12, 2011
INVENTOR(S)     : Schwede et al.

It is certified that error appears in the above-identified patent and that said Letters Patent is hereby corrected as shown below:

Column 107, line 12, reads "1. Compounds of general formula (I)" should read
--1. A compound of formula (I)--

Column 108, line 33, reads "2. A compounds according to claim 1, in which" should read
--2. A compound according to claim 1, in which--

Column 109, line 13, reads "3. Compounds according to claim 2, in which" should read
--3. A compound according to claim 2, in which--

Column 109, line 52, reads "4. Compounds according to claim 3, in which" should read
--4. A compound according to claim 3, in which--

Column 110, line 21, reads "5. Compounds according to claim 1, in which" should read
--5. A compound according to claim 1, in which--

Column 110, line 29, reads "6. Compounds according to claim 4, in which" should read
--6. A compound according to claim 4, in which--

Column 110, line 47, reads "7. Compounds according to claim 6, in which" should read
--7. A compound according to claim 6, in which--

Column 110, line 65, reads "8. Compounds according to claim 7, in which" should read
--8. A compound according to claim 7, in which--

Column 111, line 60, claim 10, reads "heteroaryl that optionally is substituted in one Or more"
should read --heteroaryl that optionally is substituted in one or more--

Column 114, line 34, claim 13, reads "pyrazolo[3,4-pyridin-3-ylamine 6-tert-Butyl-4-(4-" should read
--pyrazolo[3,4b]-pyridin-3-ylamine 6-tert-Butyl-4-(4- --

Signed and Sealed this
Thirtieth Day of October, 2012

David J. Kappos
*Director of the United States Patent and Trademark Office*

CERTIFICATE OF CORRECTION (continued)
U.S. Pat. No. 7,977,325 B2

Column 114, line 35, claim 13, reads "benzyloxyphenyl)-1H-pyrazolo[3,4]pyridine-3-ylamine" should read --benzyloxyphenyl)-1H-pyrazolo[3,4b]pyridine-3-ylamine--

Column 114, line 52, claim 13, reads "tolyl-1H-pyrazolo[3,4b]ppidin-3-ylamine 6-(1,4-Dioxa-" should read --tolyl-1H-pyrazolo[3,4b]pyridin-3-ylamine 6-(1,4-Dioxa- --

Column 114, line 53, claim 13, reads "spiro[4.5]dec-8-yl)-4-(4-phenoxyphenyl)-1H-pyrazolo[3,4]" should read --spiro[4.5]dec-8-yl)-4-(4-phenoxyphenyl)-1H-pyrazolo[3,4b]--

Column 114, line 59, claim 13, reads "pyrazolo[3,4b]pyridine-3-ylarnine 6-[4-(4-Methyl-piperazin-" should read --pyrazolo[3,4b]pyridine-3-ylamine 6-[4-(4-Methyl-piperazin- --

Column 115, line 24, claim 13, reads "2,3dimethoxyphenol 6-Cyclopropyl-4-(3,4-dichlorophe-" should read --2,3-dimethoxyphenol 6-Cyclopropyl-4-(3,4-dichlorophe- --

Column 115, line 35, claim 13, reads "4-diehlorophenyl)-1H-pyrazolo[3,4-b]pyridine-3-ylamine" should read --4-dichlorophenyl)-1H-pyrazolo[3,4-b]pyridine-3-ylamine--